(12) United States Patent
Chapman et al.

(10) Patent No.: US 8,177,072 B2
(45) Date of Patent: May 15, 2012

(54) APPARATUS AND METHOD FOR SEPARATING AND ISOLATING COMPONENTS OF A BIOLOGICAL FLUID

(75) Inventors: John R. Chapman, Sacramento, CA (US); Vijay Kumar, Gold River, CA (US); Brian K. Cinquini, Sacramento, CA (US); Phillip D. Kingsley, Mather, CA (US)

(73) Assignee: ThermoGenesis Corp., Rancho Cordova, CA (US)

( * ) Notice: Subject to any disclaimer, the term of this patent is extended or adjusted under 35 U.S.C. 154(b) by 572 days.

(21) Appl. No.: 12/315,722

(22) Filed: Dec. 4, 2008

(65) Prior Publication Data

US 2010/0140182 A1      Jun. 10, 2010

(51) Int. Cl.
  *B01D 21/26* (2006.01)
(52) U.S. Cl. .................. 210/380.1; 210/360.1; 210/516; 210/782; 210/789; 422/533; 422/548; 422/550; 422/559; 494/4; 494/5; 494/43; 494/67; 494/85; 604/6.01; 604/6.15; 604/218; 604/403
(58) Field of Classification Search .................. 210/787, 210/109, 121, 125, 516, 518, 361, 789, 512.1, 210/512.2, 242.1, 513, 515, 519, 523, 380.1, 210/360.1, 782, 741; 422/533, 548, 550, 422/559; 494/4, 5, 43, 67, 85; 604/6.01, 604/6.15, 218, 403
See application file for complete search history.

(56) References Cited

U.S. PATENT DOCUMENTS

| | | | |
|---|---|---|---|
| 280,820 A | 7/1883 | Hickson | |
| 593,333 A | 11/1897 | Park | |
| 3,587,911 A | 6/1971 | Creith | |
| 3,596,652 A | * 8/1971 | Winkelman | 600/575 |
| 3,741,400 A | 6/1973 | Dick | |
| 3,786,985 A | 1/1974 | Blaivas | |
| 3,799,345 A | 3/1974 | Svantesson | |
| 3,814,248 A | 6/1974 | Lawhead | |
| 3,891,553 A | 6/1975 | Ayres | |
| 3,894,951 A | 7/1975 | Ayres | |
| 3,894,952 A | 7/1975 | Ayres | |
| 3,897,343 A | 7/1975 | Ayres | |
| 3,931,010 A | 1/1976 | Ayres | |

(Continued)

FOREIGN PATENT DOCUMENTS

EP    0295771 A2    12/1988
(Continued)

*Primary Examiner* — Tony G Soohoo
*Assistant Examiner* — David C Mellon
(74) *Attorney, Agent, or Firm* — Dennis A. DeBoo; Audrey A. Millemann; Weintraub Genshlea et al.

(57) ABSTRACT

A device for separating and isolating components of a biological fluid comprising a container for containing the fluid to be processed, a tube cap assembly for closing the container while providing filling and extraction communication therewith, a float assembly disposed within the container for funneling and controlling biological fluid flow into an inverted domed shaped isolation chamber within the float and controlling the biological fluid flow out of the isolation chamber for effecting an encapsulation or a sealed isolation of at least one component or fraction of the biological fluid flow within the isolation chamber during a centrifugation process. The device further comprising a flexible tube for connecting an extraction passageway disposed within the float assembly and an extraction valve of the tube cap assembly for allowing extraction of at least the one component or fraction encapsulated or isolated within the chamber.

18 Claims, 34 Drawing Sheets

U.S. PATENT DOCUMENTS

| | | | |
|---|---|---|---|
| 3,932,277 A | 1/1976 | McDermott |
| 3,945,928 A | 3/1976 | Ayres |
| 3,951,801 A | 4/1976 | Ayres |
| 3,957,654 A | 5/1976 | Ayres |
| 3,960,727 A | 6/1976 | Hochstrasser |
| 3,972,812 A | 8/1976 | Gresl |
| 4,001,122 A | 1/1977 | Griffin |
| 4,057,499 A | 11/1977 | Buono |
| 4,083,788 A | 4/1978 | Ferrara |
| 4,088,582 A | 5/1978 | Murty |
| 4,152,270 A | 5/1979 | Cornell |
| 4,202,769 A | 5/1980 | Greenspan |
| 4,364,832 A | 12/1982 | Ballies |
| 4,416,778 A | 11/1983 | Rogers |
| 4,443,345 A | 4/1984 | Wells |
| 4,816,168 A | 3/1989 | Carrol |
| 4,818,386 A | 4/1989 | Burns |
| 4,853,137 A | 8/1989 | Ersson |
| 4,877,520 A | 10/1989 | Burns |
| 4,957,637 A | 9/1990 | Cornell |
| 5,251,474 A | 10/1993 | Wardlaw |
| 5,314,074 A | 5/1994 | Inbar |
| 5,393,674 A | 2/1995 | Levine |
| 5,397,479 A | 3/1995 | Kass |
| 5,454,958 A | 10/1995 | Fiehler |
| 5,455,009 A | 10/1995 | Vogler |
| 5,456,885 A | 10/1995 | Coleman |
| 5,462,716 A | 10/1995 | Holm |
| 5,494,590 A | 2/1996 | Smith |
| 5,560,830 A | 10/1996 | Coleman |
| 5,577,513 A | 11/1996 | Van Vlasselaer |
| 5,603,845 A | 2/1997 | Holm |
| 5,632,905 A | 5/1997 | Haynes |
| 5,663,051 A | 9/1997 | Van Vlasselaer |
| 5,672,481 A * | 9/1997 | Minshall et al. ............ 435/7.21 |
| 5,707,876 A | 1/1998 | Levine |
| 5,736,033 A | 4/1998 | Coleman |
| 5,792,344 A | 8/1998 | Holm |
| 5,858,253 A | 1/1999 | Holm |
| 5,866,071 A | 2/1999 | Leu |
| 5,889,584 A | 3/1999 | Wardlaw |
| 5,918,622 A | 7/1999 | Perez |
| 5,989,215 A | 11/1999 | Delmotte |
| 6,123,655 A | 9/2000 | Fell |
| 6,146,124 A | 11/2000 | Coelho |
| 6,197,579 B1 | 3/2001 | Van Vlasselaer |
| 6,280,400 B1 | 8/2001 | Niermann |
| 6,398,705 B1 | 6/2002 | Grumberg |
| 6,398,972 B1 | 6/2002 | Blasetti |
| 6,406,671 B1 | 6/2002 | DiCesare |
| 6,471,069 B2 | 10/2002 | Lin |
| 6,497,325 B1 | 12/2002 | DiCesare et al. |
| 6,516,953 B1 | 2/2003 | DiCesare |
| 6,599,274 B1 | 7/2003 | Kucharczyk |
| 6,727,101 B1 | 4/2004 | Sagstetter |
| 6,758,828 B2 | 7/2004 | Hammer et al. |
| 6,835,353 B2 | 12/2004 | Smith |
| 6,905,612 B2 | 6/2005 | Dorian |
| 7,074,577 B2 | 7/2006 | Harbert |
| 7,077,273 B2 | 7/2006 | Ellsworth |
| 7,153,477 B2 | 12/2006 | DiCesare |
| 7,179,391 B2 | 2/2007 | Leach |
| 7,223,346 B2 | 5/2007 | Dorian |
| 7,291,450 B2 | 11/2007 | Sowemimo-Coker |
| 7,329,534 B2 | 2/2008 | Haubert |
| 7,358,095 B2 | 4/2008 | Haubert |
| 7,374,678 B2 | 5/2008 | Leach |
| 7,470,371 B2 | 12/2008 | Dorian |
| 7,553,413 B2 | 6/2009 | Dorian |
| 8,062,534 B2 * | 11/2011 | Higgins et al. ................ 210/787 |
| 2002/0023884 A1 * | 2/2002 | Anderson ..................... 210/787 |
| 2006/0175242 A1 | 8/2006 | Dorian |
| 2006/0175244 A1 | 8/2006 | Dorian |
| 2006/0273049 A1 | 12/2006 | Leach et al. |
| 2007/0075016 A1 | 4/2007 | Leach |
| 2007/0258956 A1 | 11/2007 | Higgins |
| 2008/0164204 A1 * | 7/2008 | Hatamian et al. ............ 210/516 |
| 2008/0217265 A1 | 9/2008 | Leach |
| 2008/0283474 A1 * | 11/2008 | Leach et al. .................. 210/789 |
| 2010/0256595 A1 * | 10/2010 | Leach et al. .................. 604/506 |
| 2011/0014705 A1 * | 1/2011 | Leach et al. .................. 435/379 |
| 2011/0192804 A1 * | 8/2011 | Landrigan et al. ............ 210/741 |

FOREIGN PATENT DOCUMENTS

| | | |
|---|---|---|
| EP | 0295771 A3 | 12/1988 |
| EP | 0311011 A2 | 4/1989 |
| WO | WO 03/099412 A1 | 12/2003 |

* cited by examiner

A method for separating a biological fluid having multiple comingled fractions using a conventional centrifugation device, the steps comprising:

Centrifuging a device containing a biological fluid having multiple comingled fractions for forming a first fraction, a second fraction and a third fraction of the biological fluid;

Isolating the third fraction within an interior isolation chamber of a float of the device during the centrifuging step;

Activating a magnetic stirring bar disposed within the interior isolation chamber of the float for stirring the third fraction after the centrifuging step, and Harvesting the stirred third fraction of the biological fluid from the device.

FIG. 21

APPARATUS AND METHOD FOR SEPARATING AND ISOLATING COMPONENTS OF A BIOLOGICAL FLUID

FIELD OF THE INVENTION

This invention relates generally to devices and methods for separating biological fluids into components having different densities and, in particular, to an apparatus and method for receiving a biological fluid sample, separating components of the biological fluid sample while isolating at least one target component from non-target components of the biological fluid sample based upon fluid component density differences, and extracting at least one isolated target component in preparation for at least one diagnostic or therapeutic application. This invention is particularly useful in the centrifugal separation of blood and bone marrow into components.

BACKGROUND OF THE INVENTION

It is known to separate biological fluids, such as aspirated bone marrow or peripheral blood, into their component parts, fractions, phases, or constituent layers by centrifugation. It is also known to provide mechanical devices comprised of a tube which houses a solid separator which, when actuated by centrifugal force, allows biological fluid to flow through or around the piston based on differing relative densities thereby separating the biological fluid into a one or more component parts above and one or more component parts below the solid separator. For example, when the biological fluid within the tube is blood, the centrifugation process results in a high density layer of red blood cells below the solid separator, a low density layer of plasma above the solid separator, and a buffy coat layer which defines an intermediate density layer or third fraction above the solid separator and below the low density layer of plasma.

One of the earliest solid separators was disclosed in U.S. Pat. No. 3,508,653, issued Apr. 28, 1970 to Coleman. That device was a rubber or other elastomeric cylinder. A major problem with that device was the inability to maintain a seal because it is costly to maintain the precise inner diameter of the test tube when mass produced. A subsequent solid separator development is disclosed in U.S. Pat. No. 3,814,248, issued Jun. 4, 1974 to Lawhead. Next, U.S. Pat. No. 3,779,383, issued Dec. 18, 1973 to Ayres disclosed a device in which the blood introduction end of the tube is opposite to the movable separator end of the tube, and abutting an impenetrable rubber closure. Following Ayres, U.S. Pat. No. 3,931,018, issued Jan. 6, 1976 to North, Jr. disclosed a solid separator for use in separation of blood serum and blood plasma using centrifugal force that must be inserted into the blood collection tube after blood collection.

In a patent to Levine, et al. (U.S. Pat. No. 4,159,896, issued Jul. 3, 1979) a centrifugally motivated solid separator device is disclosed in which a cylindrical float is disposed inside of a tube, which float has an accurately controlled outside diameter so as to fit snugly in the tube bore under static conditions. When used in harvesting blood cells the float is formed with an axial through bore which receives and expands the white cell and platelet layers in the blood sample after centrifugation thereof. The disclosed float was made from a plastic material having a specific gravity that causes it to float in the packed red cells after centrifugation of the blood sample in the tube.

In another patent to Levine, et al, (U.S. Pat. No. 5,393,674, issued Feb. 28, 1995) a clear plastic tube large enough to process 1 ml of blood and equipped with a cylindrical float and filled with an inert gas at low pressure is disclosed. The float contains a through bore, and prior to centrifugation, is held fixably at an initial location by tight contact between the exterior of the float and the interior wall of the tube. Unlike the inventions of Coleman, which contain pistons (or buoys) with no through bore, the Levine float relocates, under centrifugation, to a new position determined by its density relative to the density of the blood fractions as a result of the shrinkage of its diameter due to the longitudinal elongation (and subsequent lateral narrowing) of the float body that results from the substantial gravity gradient that occurs from the top to the bottom of the float. This substantial G force gradient (several thousand Gs) causes the float to elongate and narrow just as a rubber tube elongates and narrows when pulled from both ends. This space between the exterior of the float and the interior of the tube that develops during centrifugation provides the freedom of movement of the float consequent with the motion of the blood components to their new location determined by their density relative to the float. Levine does not posit, but it is assumed that some of the redistributing blood components also travel through the bore during centrifugation but since the top and bottom of the through bore are not closed, any cells and platelets that wind up there following centrifugation are easily infiltrated by the red cells and plasma during normal post centrifugation handling. Designed predominately as a diagnostic tool that proceeds through the visual examination of the cells that at least temporarily occupy the through bore right after centrifugation, Levine also discloses the possibility of extracting these cells with a syringe needle for additional diagnostic examination. This method of extraction necessarily is inefficient as a means of cell recovery as the intruding needle necessarily relocates the target cells above and below the through bore as it is inserted.

Hence, these known mechanical devices are generally capable of separating biological fluids into component parts or fractions; however, these devices are not very precise thereby resulting in inefficient separation of the biological fluid into component parts or fractions because of the substantial comingling of the separated fractions. Additionally, these known mechanical devices fail to provide a simple or efficient method to extract a fraction other than the top fraction of the sample leading to low recoveries, especially of the clinically important buffy coat fraction.

It is also known to provide more complicated mechanical devices in an attempt to alleviate the above known problems. For example, the patent to Leach, et al. (U.S. Pat. No. 7,374,678, issued May 20, 2008) in a first embodiment, discloses a device for separating a sample, such as blood, into a plurality of fractions. The device is comprised of a plunger (or second piston) which, prior to centrifugation, is retained proximate a top end of a closed ended distortable tube during centrifugation and a first piston (or buoy) which is tightly fitted near the bottom of the closed ended distortable tube such that under centrifugation with a sample of blood, the tube wall longitudinally compresses and bows outward thereby allowing the buoy to move in a direction of the top of the tube lifted by a layer of red blood cells of higher density than the piston that has flowed downward between the buoy and the interior of the tube wall. After centrifugation, the tube wall returns to its original dimension and traps this first piston at a new location coinciding with the interface position of a top plasma fraction and a bottom red blood fraction of the separated sample. On or near a collection face of this first piston (or buoy) is a third fraction which includes "a small, yet concentrated, amount of red blood cells, white blood cells, platelets, and a substantial portion of a buffy coat of the blood sample." The device then employs a plunger (or second piston) which is manually pushed down into the tube from a location proximate the top end of the tube. The plunger (or second piston) includes a valve which allows the plasma to pass through the plunger to while the plunger is lowered to a predetermined depth above the first piston set by a depth gauge which locates the plunger a distance away from the collection face of the piston thereby defining a third fraction between a bottom face of the plunger (or second piston) and the collection face of the first piston. The extraction of the third fraction is accomplished via a vacuum created on a tube extending between a collection valve disposed in the top of the tube and a bore extending from the top of the plunger and the bottom of the plunger.

Accordingly, this device relies on the imprecise longitudinal compression and decompression of the tube wall in order to control the flow path between fractions and fails to contain the separated fractions until after centrifugation stops and the tube wall returns to its original dimensions. Furthermore, the extraction of the third fraction requires infiltration of the top plasma fraction. Hence, this recently patented device still fails to alleviate the problem of inefficient separation of the biological fluid into component parts or fractions and the comingling of the separated fractions.

In another embodiment, Leach, et al. discloses that the plunger (or second piston) is rigidly or slideably fitted with the first piston or buoy such that the pair is tightly fitted within the closed ended distortable tube wherein under centrifugation with a sample such of blood, the tube wall bows outward thereby allowing the pair to move in a direction of the top of the tube while lifted by a high density layer of red blood cells flowing downward between the pair and the interior of the tube wall. After centrifugation, the tube wall returns to its original dimension which grips the periphery of the first piston at an interface position of a plasma fraction and a red blood fraction of the separated sample. On or near a collection face of this first piston is "a small, yet concentrated, amount of red blood cells, white blood cells, platelets, and a substantial portion of a buffy coat of the blood sample." The extraction of the intermediate (buffy coat) or third fraction is accomplished "by interconnecting a cannula or bored tube with the connection portion of the buoy cylinder" and connecting an extraction syringe to the cannula for creating a vacuum to draw the intermediate or third fraction from the space between the first and second pistons. This embodiment describes only one centrifugation spin, and fails to alleviate the problem of inefficient separation of the biological fluid into component parts or fractions and the comingling of the separated fractions. Furthermore, the extraction of a fraction other than the top fraction still requires the infiltration of at least one other fraction than the desired fraction to be extracted. Moreover, the device relies on the imprecise longitudinal compression and decompression of the tube wall in order to control the flow path between fractions and fails to contain the separated fractions until centrifugation stops and decompression of the tube wall is concluded.

Another problem associated with both embodiments of Leach, et al. is that the collection face, trough, or sump of the buoy must be shallow to be at a desired density level of the target buffy coat fraction and to preclude even further accumulation of reds cells with the target white cells and platelets to be extracted. Thus, this shallow trough results in having the target white blood cells and platelets, come to rest on the entire large surface area of the first piston on which the white blood cells and platelets tend to stick, which reduces the efficiency of the final collection step. A further problem associated with both embodiments of Leach, et al. is the time consuming and laborious process of fitting and interconnecting multiple parts to the device in order to perform the extraction process.

In general, current processes for separating and extracting fractions out of biological fluids require multiple steps that are both laborious and time consuming and that result in poor recoveries of the target white cells and platelets. Hence, it would be desirable to provide a simplified and more effective process so less time, labor, and training is required to do the procedure and fewer white cells and platelets are lost thereby providing a positive economic impact. A simplified process would also allow it to be performed in an intra-operative setting by an operating room nurse, rather than a remote laboratory setting by a technician so that a patient can be more rapidly treated and the possibility of mixing up samples can be essentially eliminated. Process simplification also has a direct correlation to process reproducibility that is also a problem with the known prior art.

Hence, the known prior art is problematic in a number of areas which include a deficiency in the recovery efficiency of cells of interest (target cells), in the selectivity of separation for reducing contamination or non-target cells from the target cell population, and in the multiple step, laborious, and time consuming extraction process.

Accordingly, there is a need to overcome the significant shortcomings of the known prior-art as delineated hereinabove.

BRIEF SUMMARY OF THE INVENTION

Accordingly, and in one aspect, an embodiment of the invention ameliorates or overcomes one or more of the significant shortcomings of the know prior art by providing a separation and isolation device comprising a float assembly slideably enveloped in an enclosure containing biological fluid for promoting fluid flow into and automatic self sealing of a chamber of the funnel float for isolating at least one component or fraction of a biological fluid being processed.

In another aspect, an embodiment of the invention provides a steep sloped entry way to a self sealing isolation chamber so that components such as cells that are flowing into the isolation chamber are precluded from sticking on the surface area of the sloped entry way.

In another aspect, an embodiment of the invention provides a float comprised of an upstream valve and a downstream valve located in a circulation path of fluid traversing through an isolation chamber of the float sealed by closure of the valves as a function of a first differential pressure on the upstream valve and a second differential pressure on the downstream valve for isolating a target component of a biological fluid within the float.

In another aspect, an embodiment of the invention provides a device for separating and isolating components of a biological fluid with centrifugation, the device comprising: an enclosure for containing a biological fluid having multiple components; a float slideably disposed within the enclosure and having an interior isolation chamber; a first valve means for allowing a flow of biological fluid into the interior isolation chamber of the float as a function of a first pressure differential of biological fluid on the first valve means; and a second valve means for providing a flow of biological fluid out of the interior isolation chamber of the float as a function of a second pressure differential of biological fluid on the second valve means wherein under device centrifugation the first valve means and the second valve means initially allow components of the biological fluid to flow through the interior isolation chamber and subsequently close to seal the interior isolation chamber as the function of the first pressure differential of biological fluid on the first valve means and as the function of the second pressure differential of biological fluid on the second valve means for isolating at least one target component of the biological fluid within the interior isolation chamber of the float.

In another aspect, an embodiment of the invention provides a device for separating and isolating components of a biological fluid with centrifugation, the device comprising: an enclosure comprising an interior circumferential surface defining a chamber for containing a biological fluid having multiple components; a float slideably disposed within the enclosure and partitioning the enclosure into a lower volume zone and an upper volume zone; the float comprising an interior isolation chamber defining an intermediate volume zone and an exterior circumferential surface circumferentially spaced from the interior circumferential surface of the enclosure for defining a circumferential gap therebetween; a first valve means for opening and closing communication of biological fluid from the upper volume zone to the interior isolation chamber within the float; and a second valve means for opening and closing communication of biological fluid from the interior isolation chamber within the float to the lower volume zone of the container wherein under centrifugation the first valve means and the second valve means control at least one closed loop circulation of biological fluid into the interior isolation chamber from the upper volume zone, out of the interior isolation chamber into the lower volume zone, out of the lower volume zone and through the circumferential gap to the upper volume zone, and back into the interior isolation chamber as a function of a first pressure differential of biological fluid on the first valve means and as a function of a second pressure differential of biological fluid on the second valve means for isolating at least one target component of the multiple component biological fluid within the interior isolation chamber of the float.

In another aspect, an embodiment of the invention provides a method for separating a biological fluid having multiple comingled fractions using a conventional centrifuge device, the steps comprising: centrifuging a device containing a biological fluid having multiple comingled fractions for forming a first fraction, a second fraction and a third fraction of the biological fluid; and utilizing a valve means for controlling entry and exit of the biological fluid through an interior isolation chamber of a float of the device for isolating the third fraction within the interior isolation chamber of the float during the centrifuging step. Additionally, and in one embodiment, the above method further comprises a step of activating a magnetic stirring bar disposed within the interior isolation chamber of the float for stirring the third fraction after the centrifuging step. Furthermore, and in one embodiment, the above method further comprises a step of harvesting the stirred third fraction of the biological fluid from the device by using an aperture in open communication with the interior isolation chamber of the float. Moreover, and in one embodiment, the above method further comprises a step of coupling at least one weight to the float for selectively tuning the density of the float to about 1.02 grams/cubic centimeter to about 1.08 grams/cubic centimeter prior to the centrifuging step.

In a particular aspect, an embodiment of the invention provides a device for separating and isolating components of a biological fluid with centrifugation, the device comprising: a container comprising a closed bottom end, an open top end, and a container sidewall extending between the closed bottom end and the open top end, the sidewall having an inner circumferential surface defining a containing chamber extending along a central longitudinal axis of the container; a cap for selectively closing the open top end of the container for defining an enclosure for containing a biological fluid having multiple components; a float assembly slideably disposed within the container and partitioning the container into a lower volume zone and an upper volume zone; the float assembly comprising: a lower cylindrical portion including an inverted hemispherically shaped interior surface surmounted by an interior ceiling surface for defining an inverted domed shaped chamber for isolating a target component of the biological fluid; an upper cylindrical portion surmounting the lower cylindrical portion and including a conically shaped upper surface defining a funnel shaped cavity converging towards the lower cylindrical portion of the float for receiving, directing, and promoting biological fluid flow from the upper volume zone toward the inverted domed shaped chamber; an open ended entrance passageway disposed within the float for providing open fluid communication between the funnel shaped cavity and the inverted domed shaped chamber; an open ended exit passageway disposed within the float for providing open communication between the inverted domed shaped chamber and the lower volume zone; a first valve means for selectively opening and closing the open ended entrance passageway as a function of a first pressure differential on the first valve means for controlling fluid flow from the funnel shaped cavity to the inverted dome shaped chamber and precluding fluid back flow through the first valve means from the inverted dome shaped chamber to the funnel shaped cavity; a second valve means for selectively opening and closing the open ended exit passageway as a function of a second pressure differential on the second valve means for controlling fluid flow out of the inverted dome shaped chamber to the lower volume zone of the container and precluding fluid back flow through the second valve means from the lower volume zone to the inverted domed shaped chamber, and wherein under centrifugation the first valve means and the second valve means initially allow components of the biological fluid to flow through the inverted domed shaped chamber and subsequently close to seal the inverted domed shaped chamber as the function of the first pressure differential on the first valve means and as the function of the second pressure differential on the second valve means for isolating the target component of the biological fluid within the inverted domed shaped chamber of the float.

Accordingly, it should be apparent that numerous modifications and adaptations may be resorted to without departing from the scope and fair meaning of the claims as set forth hereinbelow following the detailed description of the invention.

DETAILED DESCRIPTION OF THE INVENTION

Figure 1:
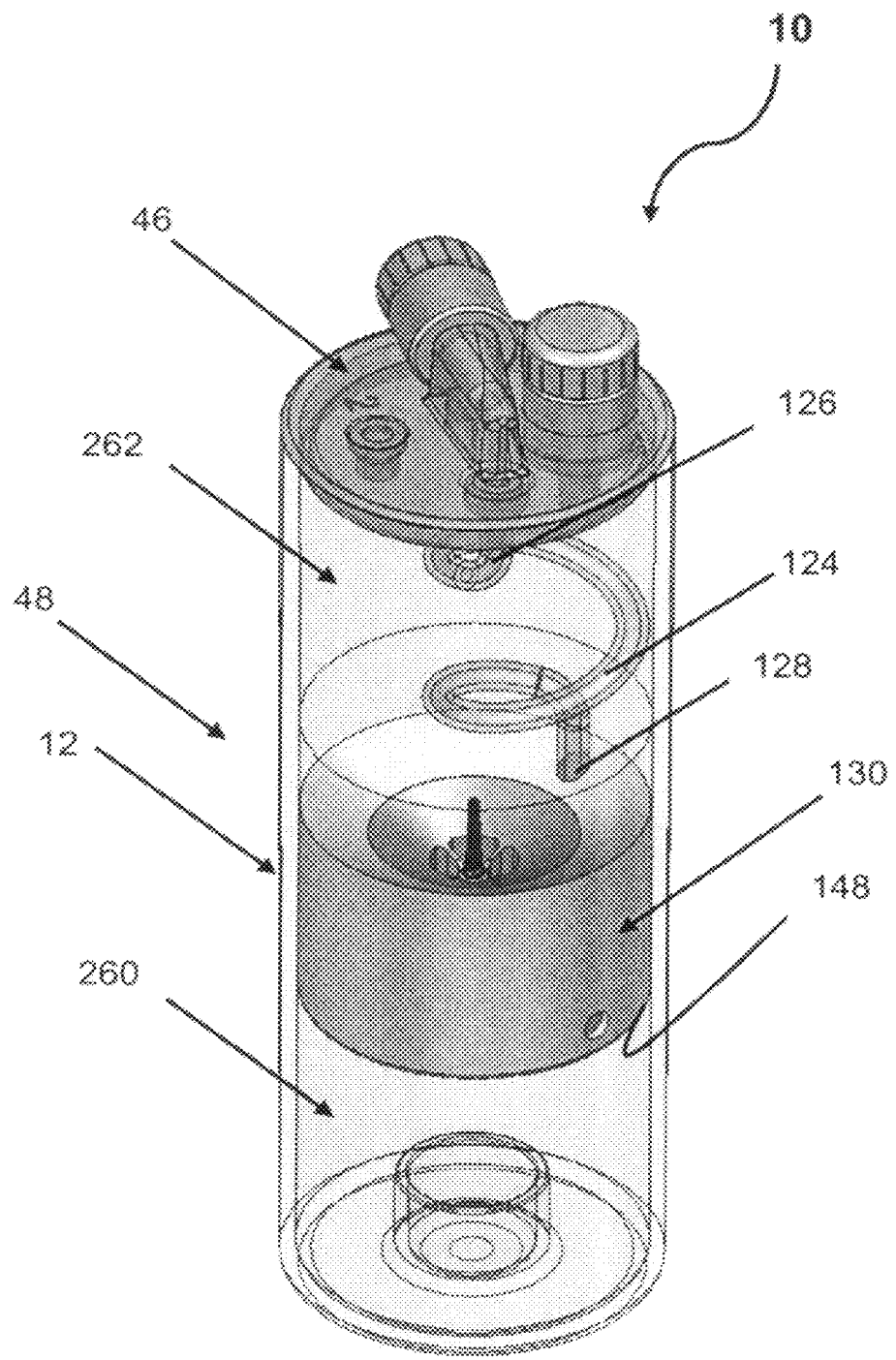
FIG. 1 is a perspective view of an embodiment of a device for separating and isolating components of a biological fluid.

Considering the drawings, wherein like reference numerals denote like parts throughout the various drawing figures, reference numeral 10 is directed to an embodiment of a device for separating and isolating components of a biological fluid and reference numeral 310 is directed to another embodiment of the device for separating and isolating components of a biological fluid.

Referring now to FIG. 1, and in one embodiment, the device 10 is comprised of a main centrifuge tube or container 12, a tube cap assembly 46 for selectively closing the container 12 for defining an enclosure 48 for receiving and containing a biological fluid having multiple components, a float assembly 130 partitioning the enclosure into a first or lower volume zone 260 below the float assembly 130 and a second or upper volume zone 262 above the float assembly 130, and a flexible tube 124 operatively coupled between the float assembly 130 and the tube cap assembly 46 for traveling up or down with the float assembly 130 by coiling or elongating respectively.

Main Centrifuge Tube 12

Figure 2:
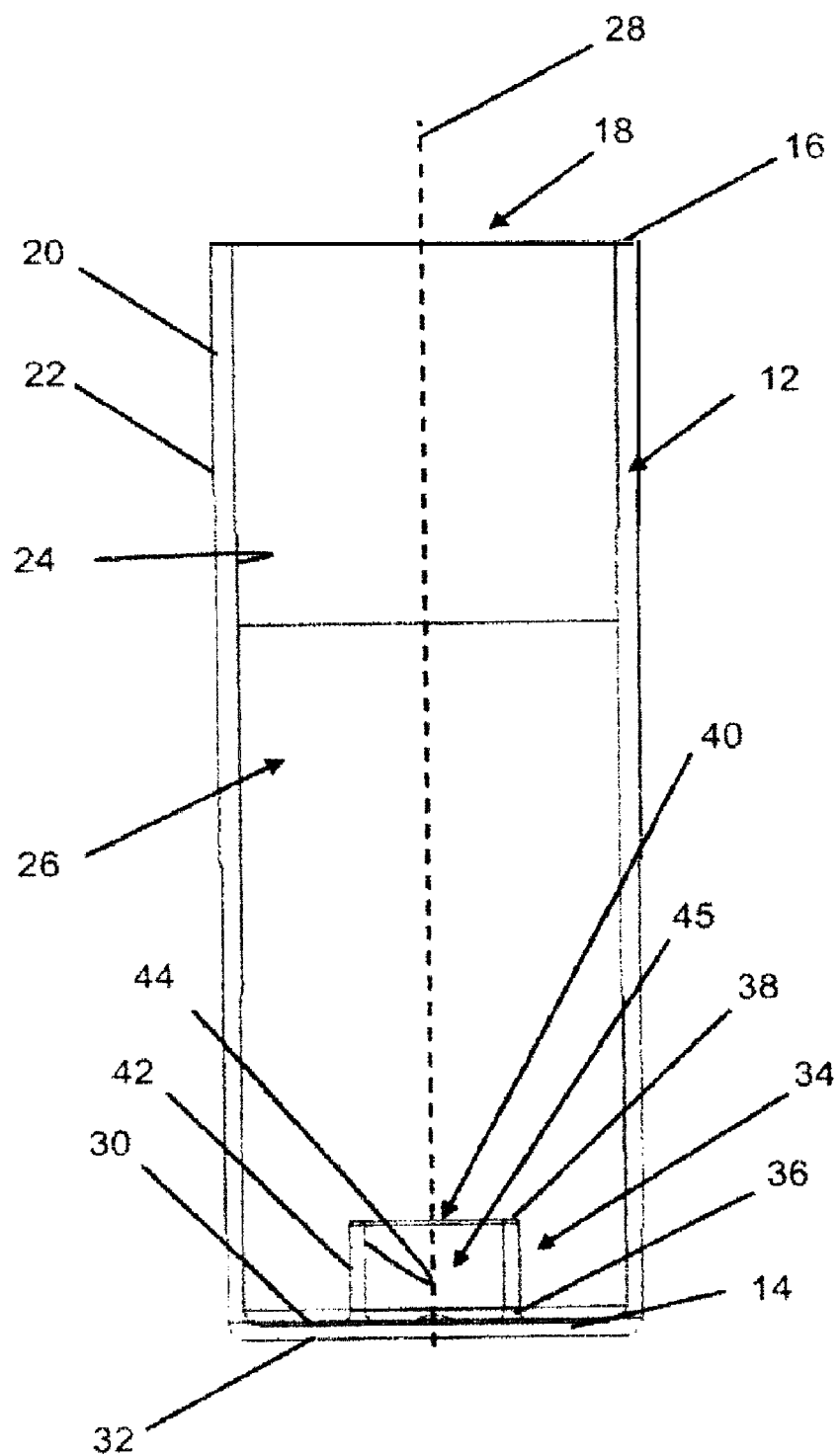
FIG. 2 is a sectional view of an embodiment of a main centrifuge tube of the device.

More specifically, and referring to FIGS. 1 and 2, the main centrifuge tube or container 12 comprises a closed bottom end 14, a substantially flat annular top edge 16 defining an open top end 18, and a cylindrical sidewall 20 extending between the closed bottom end 14 and the annular top edge 16. The cylindrical sidewall 20 includes an outer cylindrical surface 22 and an inner circumferential or cylindrical surface 24 which defines a cylindrically shaped containing chamber 26 extending along a central longitudinal axis 28 of the tube 12 which is also the central longitudinal axis of the device 10.

In one embodiment, the closed bottom end 14 is substantially formed as a disk shaped member having an interior surface 30 and an exterior surface 32. The interior surface 30 includes an inner radiused edge transitioning into the inner cylindrical surface 24 of the cylindrical sidewall 20. Similarly, the exterior face 32 includes an outer radiused edge transitioning into the outer cylindrical surface 22 of the cylindrical sidewall 20. Additionally, the closed bottom end 14 may be selectively closeable or integrally formed with the cylindrical sidewall 20.

Furthermore, the tube is preferably constructed of, but not limited to, a material which is both biocompatible and stable for gamma irradiation. In one embodiment, the tube 12 is constructed of, but not limited to, a polycarbonate or polystyrene material.

Standoff Member 34

Still referring to FIGS. 1 and 2, the tube 12 further comprises an open ended hollow cylindrical standoff member 34 coaxially disposed within the main centrifuge tube 12 and comprised of a circular bottom edge 36 coupled to or integrally formed with the closed bottom end 14, a circular top edge 38 defining an open top end 40, and a cylindrical sidewall 42 extending between the circular bottom edge 36 and the circular top edge 38. The cylindrical sidewall 42 includes an interior surface 44 defining a cylindrically shaped receiving chamber 45 concentrically disposed with the central longitudinal axis 28 of the main centrifuge tube 12. In one embodiment, the standoff member 34 has an outer diameter and a height which are both substantially less than a respective outer diameter and height of the main centrifuge tube 12. The function of the standoff member 34 will be further delineated hereinbelow. Moreover, and in one embodiment, the standoff member 34 is constructed of, but not limited to, the same material as the main centrifuge tube 12.

Tube Cap Assembly 48

Figure 3:
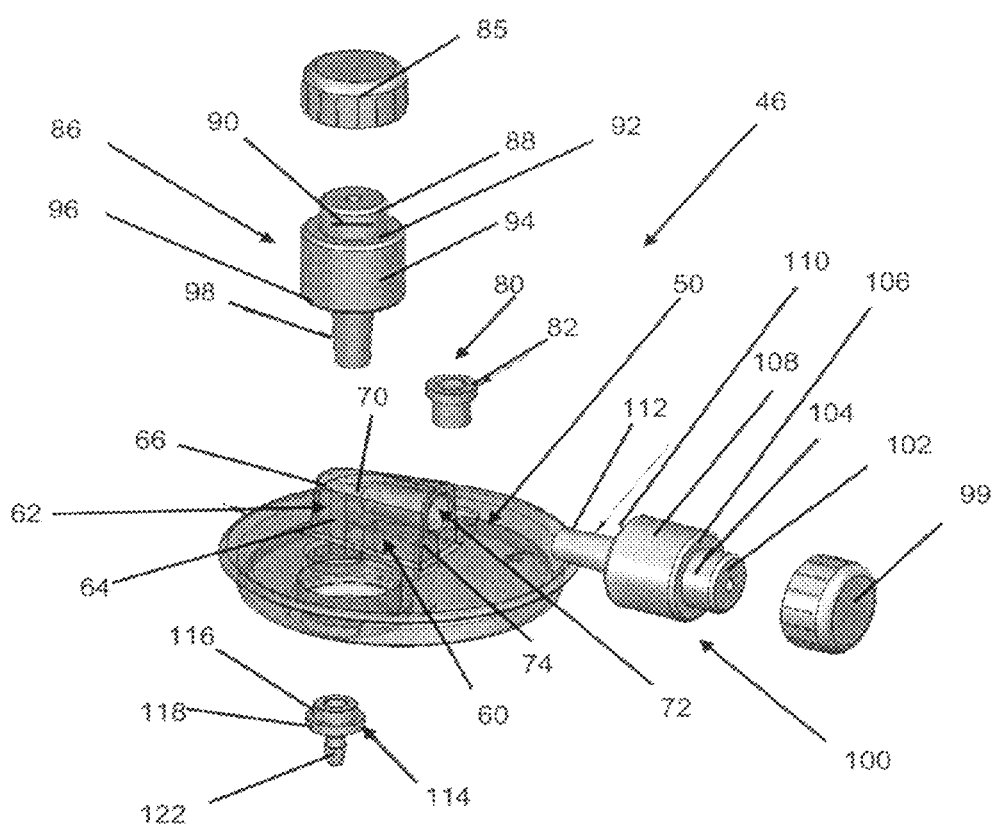
FIG. 3 is an exploded parts view of an embodiment of a cap and valve assembly of the device.

Referring to FIG. 3, and in one embodiment, the device 10 is further comprised of the tube cap assembly 48 which comprises a tube cap 50, a hydrophobic air filter 80, an inlet valve 86, an outlet or extraction valve 100, and a barb fitting 114.

Tube Cap 50

Figure 4:
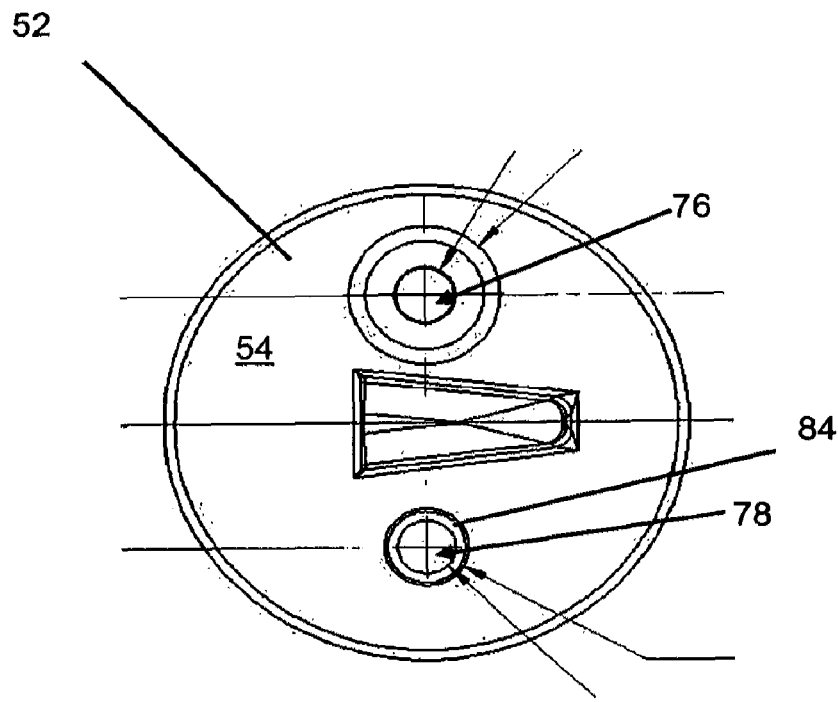
FIG. 4 is a top plan view of the cap illustrated in FIG. 3.
Figure 5:
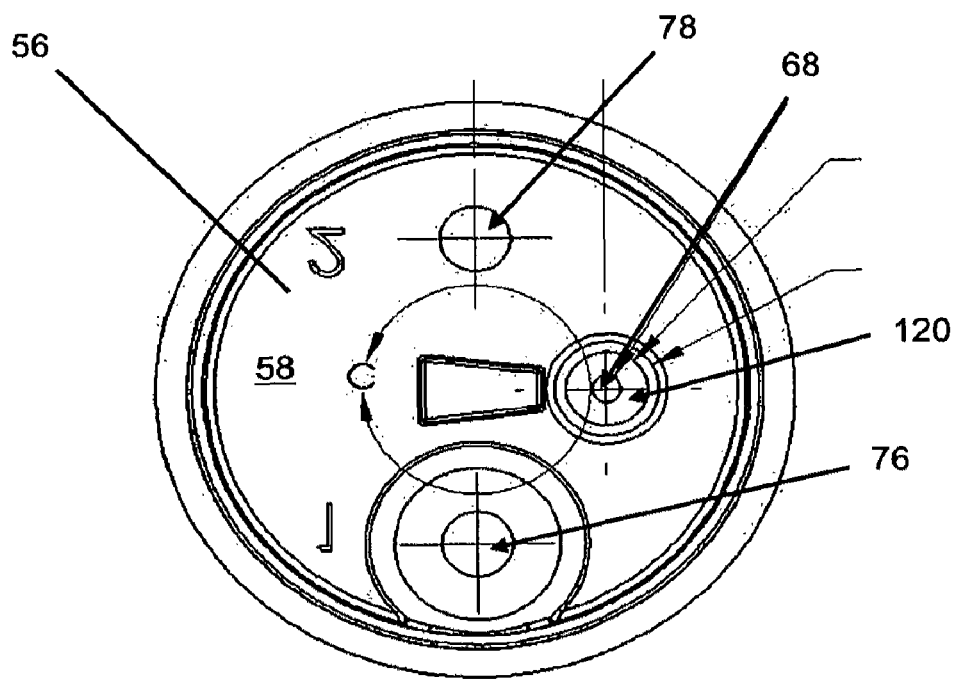
FIG. 5 is a bottom plan view of the cap illustrated in FIG. 3.

Referring now to FIGS. 3 through 5, the tube cap 50 is comprised of an upper annular portion 52 extending from an upper surface 54 of the tube cap 50 to a lower annular portion 56 having a lesser diameter than upper annular portion 52 and terminating to a lower surface 58 of the tube cap 50. The upper annular portion 52 extends over and abuts annular top edge 16 of cylindrical sidewall 20 while the lower annular portion 56 extends into and forms an interference fit with inner cylindrical surface 24 of cylindrical sidewall 20 for providing a coupling between the tube cap 50 and the main centrifuge tube 12 such that the tube cap 50 fits over and is maintained in place in open top end 18. In one embodiment, the tube cap 50 is medically bonded to the main centrifuge tube 12.

The tube cap 50 is also preferably constructed of, but not limited to, a material which is both biocompatible and stable for gamma irradiation. In one embodiment, the tube cap 50 is constructed of, but not limited to, a polycarbonate material.

Continuing to refer to FIGS. 3 through 5, the tub cap 50 is further comprised of a passageway housing 60 attached to or integrally formed with the upper annular portion 52 of the tube cap 50. The passageway housing 60 upwardly extends from the upper surface 54 of the tube cap 50 and includes an L-shaped passageway 62 having a first passageway branch 64 extending between a passageway branch bend 66 and a housing inlet port 68 recessed and disposed in the lower surface 58 of the tub cap 50. In turn, a second passageway branch 70 of the L-shaped extraction passageway 62 extends between the passageway branch bend 66 and a housing outlet port 72 disposed in a housing sidewall 74 of the passageway housing 60. The second passageway branch 70 includes a taper extending away from the housing outlet port 72 and terminating prior to reaching branch bend 66.

The tub cap 50 is preferably constructed of, but not limited to, a material which is both biocompatible and stable for gamma irradiation. In one embodiment, the tub cap 50 is constructed of, but not limited to, a polycarbonate or polystyrene material.

Moreover, the tub cap 50 further includes an inlet valve aperture 76 disposed through the tube cap 50 proximate one side of the passageway housing 60 and an air filter aperture 78 disposed through the tube cap 50 proximate the other side of the passageway housing 60.

Air Filter 80, Inlet Valve 86, Extraction Valve 100, Barb Fitting 114

Still referring to FIGS. 3 through 5, the tube cap assembly 48 comprises the hydrophobic air filter 80 disposed in the air filter aperture 78 and comprised of a flange 82 that abuts a recessed ledge 84 disposed in upper annular portion 52 of the tube cap 50 at a location circumscribing the air filter aperture 78.

The hydrophobic air filter 80 is also preferably constructed of, but not limited to, a material which is both biocompatible and stable for gamma irradiation. In one embodiment, the hydrophobic air filter 80 is constructed of, but not limited to, a polypropylene material with a PTFE filter material. One example of the hydrophobic air filter 80 is commercially available as part number X5009 from Qosina.

Additionally, the tube cap assembly 48 comprises the inlet valve 86 which includes a conventional male luer lock head 88 having external threads 90. The head 88 transitions into a shoulder 92 of a cylindrical body 94 which terminates to an underside 96 which, in turn, transitions into to a lower tapered end 98. The lower tapered end 98 of the inlet valve 86 is disposed through the inlet valve aperture 76 until the underside 96 of inlet valve 86 abuts the upper surface 54 of the tube cap 50.

Furthermore, the tube cap assembly 48 comprises the outlet or extraction valve 100 which, in one embodiment, includes a conventional male luer lock head 102 having external threads 104. The head 102 transitions into a shoulder 106 of a cylindrical body 108 which terminates to an underside 110 which, in turn, transitions into to a lower tapered end 112. The lower tapered end 112 of the extraction valve 100 is disposed through the housing outlet port 72 until the underside 110 of the extraction valve 100 abuts the housing sidewall 74 of the passageway housing 60.

The inlet valve 86 and the outlet or extraction valve 100 are also both preferably constructed of, but not limited to, a material which is both biocompatible and stable for gamma irradiation. In one embodiment, both the inlet valve 86 and the outlet or extraction valve 100 are constructed of, but not limited to, a polycarbonate material with a silicone rubber insert material. One example of the inlet valve 86 and the outlet or extraction valve 100 is commercially available as part number 245501024 from Halkey-Roberts.

Moreover, the tube cap assembly comprises the barb fitting 114 which, in one embodiment, includes a short cylindrical portion 116 disposed in the housing inlet port 68, a flange 118 transitioning from the short cylindrical portion 116 and abutting a recessed ledge 120 disposed in lower annular portion 56 at a location circumscribing the housing inlet port 68, and a barbed end 122 transitioning from the flange 118 and operatively coupled to an upper end 126 of the coiled tube 124 as shown in FIG. 1. In turn, the coiled tube 124 includes a lower end 128 coupled to the float assembly 130 as will be further delineated hereinbelow.

The barb fitting 114 is also preferably constructed of, but not limited to, a material which is both biocompatible and stable for gamma irradiation. In one embodiment, the barb fitting 114 is constructed of, but not limited to, an ABS material. One example of the barb fitting 114 is commercially available as part number BDMR210-81 from Value Plastics, Inc.

Float Assembly 130

Figure 6:
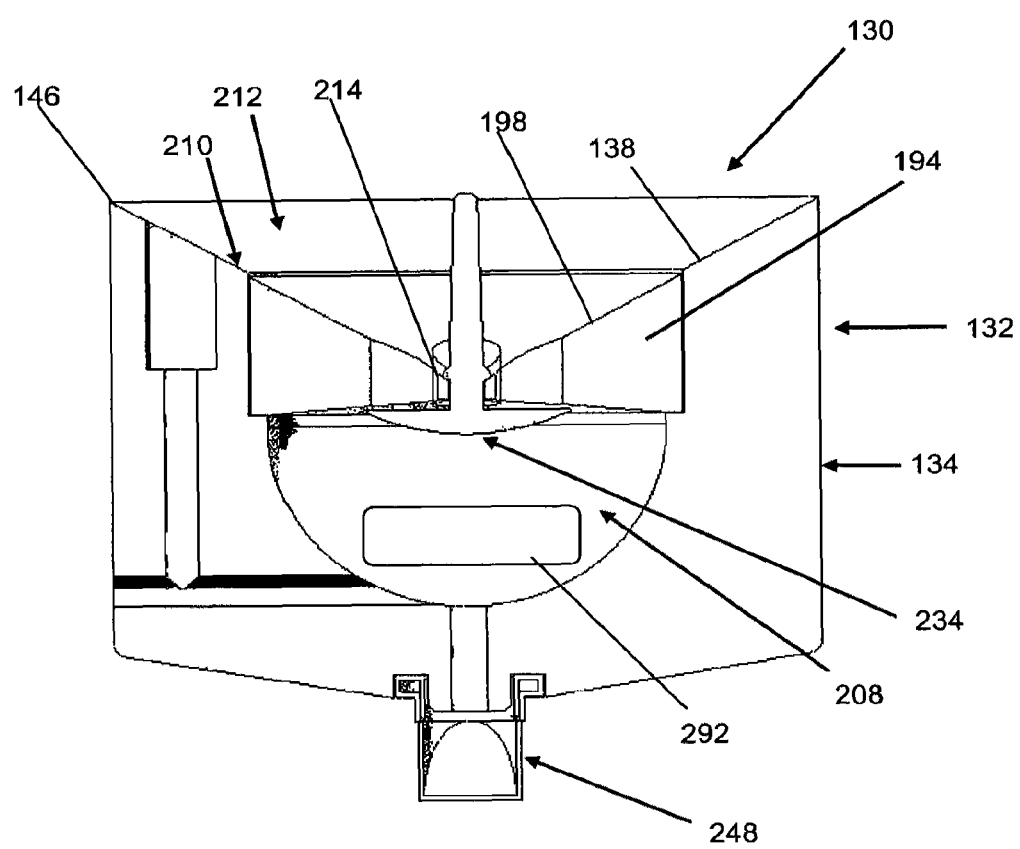
FIG. 6 is a sectional view of an embodiment of a funnel float assembly of the device illustrated in FIG. 1.

Referring now to FIGS. 1 and 6, and as noted hereinabove, the device 10 comprises float assembly 130 which can be defined as a dual density subsurface funnel and isolation float assembly 130 which is slideably disposed within the container 12 and which partitions the container 12 into the first or lower volume zone 260 below the float assembly 130, the second or upper volume zone 262 above the float assembly 130, and an isolation or third volume zone defined by an isolation chamber 208 within the float assembly 130 as further delineated hereinbelow.

In one embodiment, the float assembly 130 is comprised of: a funnel and isolation float 132 comprised of a float body 134 and a float cap 194; a first check valve means in the form of an umbrella valve 234; and a second check valve means in the form of a duckbill valve 248. The funnel float 132 can be manufactured as multiple elements or as a single, unitary element.

Float body 134

Figure 7:
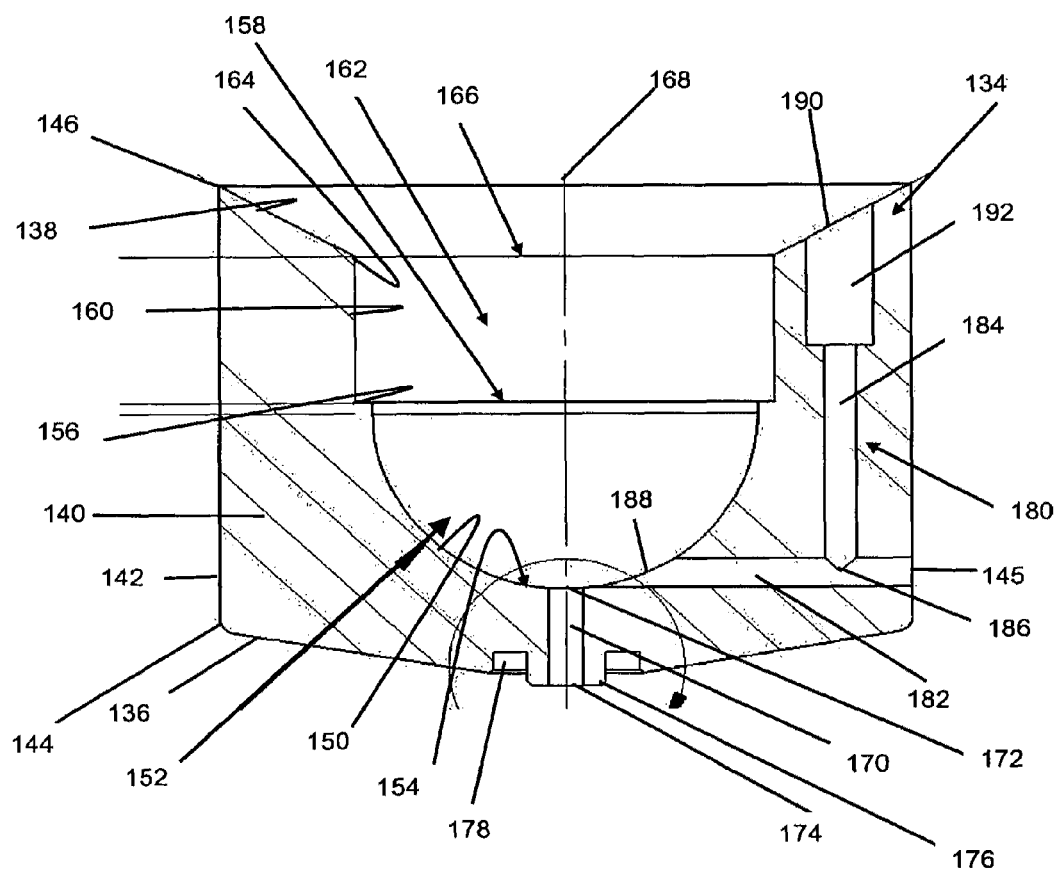
FIG. 7 is a sectional view of an embodiment of a float body of the funnel float assembly illustrated in FIG. 6.

More specifically, and referring to FIGS. 6 and 7, the float body 134 comprises a circular bottom surface 136, a frustum shaped upper top surface 138, and a float sidewall 140 extending between the circular bottom surface 136 and the frustum shaped upper top surface 138. The circular bottom surface 136 can be substantially flat or taper toward a central longitudinal axis 168 of the float body 134.

The float sidewall 140 includes an outer circumferential or cylindrical surface 142 extending between a circular outer periphery 144 of the circular bottom surface 136 and a circular outer edge 146 of the upper frustum shaped top surface 138. The outer circumferential surface 142 of the float sidewall 140 defines a diameter that is less than a diameter defined by the inner circumferential surface 24 of the main centrifuge tube 12 for defining a circumferential gap 148 between the outer circumferential surface 142 of the float sidewall 140 and the inner circumferential surface 24 of the tube 12.

Additionally, the float sidewall 140 includes an inner hemispherical surface 150 defining an inverted domed shaped or hemispherical shaped cavity 152 extending from a radiused bottom section 154 of the hemispherical surface 150 to an upper annular ledge 156 defining and annular opening 158 of the inverted domed shaped cavity 152. The upper annular ledge 156 transitions into an inner cylindrical surface 160 defining an open ended cylindrically shaped cavity 162 surmounting the inverted domed shaped cavity 152 such that the annular opening 158 also defines a lower opening of the cylindrically shaped cavity 162. In turn, the inner cylindrical surface 160 extends from the annular ledge 156 to a circular inner edge 164 of the frustum shaped upper top surface 138. The circular inner edge 164 circumscribes and defines an annular opening 166 between the cylindrically shaped cavity 162 and the frustum shaped upper top surface 138 such that the opening 166 defines an upper opening of the cylindrically shaped cavity 162 and a lower opening of the frustum shaped upper top surface 138.

Furthermore, the float body 134 is preferably constructed of, but not limited to, a material which is both biocompatible and stable for gamma irradiation. In one embodiment, the float body 134 is constructed of, but not limited to, a polystyrene or polycarbonate type of material.

Exit Passageway 170 and Extraction Passageway 180

Figure 8:
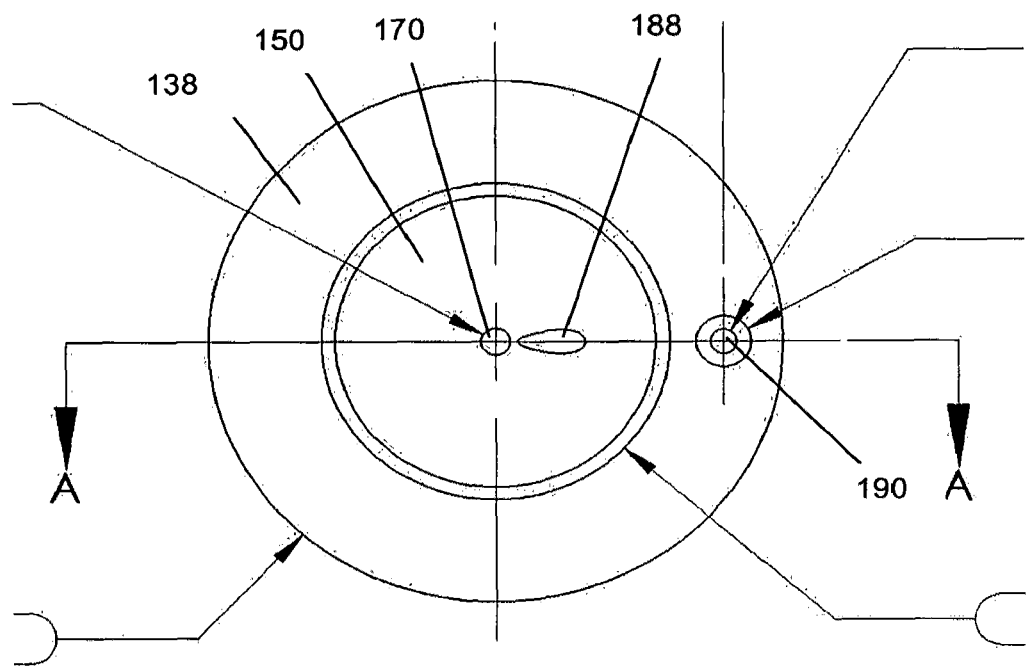
FIG. 8 is a top plan view of the float body illustrated in FIG. 7.
Figure 9:
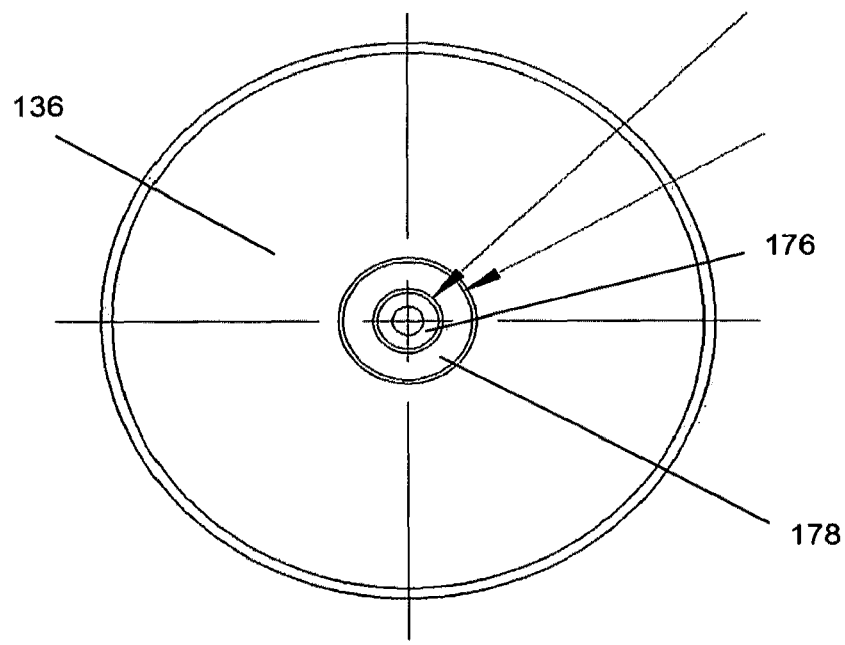
FIG. 9 is a bottom plan view of the float body illustrated in FIG. 7.

Referring to FIGS. 7 through 9, the float body 134 further comprises an exit passageway 170 extending between an first circular exit port 172 disposed in the radiused bottom section 154 of the inner hemispherical surface 150 of the float body 134 and a second circular exit port 174 disposed in the bottom surface 136 of the float body 134 for providing open fluid communication between the inverted domed shaped cavity 152 and the first or lower volume zone 260 below the float assembly 130. Additionally, and in one embodiment, the first and second circular exit ports have a common axis defined by the central longitudinal axis 168 of the float body 134. Furthermore, the second circular exit port 174 is circumscribed by an annular shoulder 176 which steps down and into an annular recessed area 178 disposed through the bottom surface 136 of the float body 134.

Still referring to FIGS. 7 through 9, the float body 134 further comprises an L-shaped extraction passageway 180 defined by a first branch 182, a second branch 184, and a branch bend 186 therebetween. The first branch 182 is formed by providing a bore through both the outer circumferential surface 142 and the float sidewall 140 at an angle substantially perpendicular to the central longitudinal axis 168 of the funnel float body 134 wherein the outer circumferential surface 142 is plugged thereafter with plug 145. The second branch 184 is formed by providing a bore through both the frustum shaped upper top surface 138 and the float sidewall 140 which terminates in the first branch 182 at bend 186 and which is at an angle substantially parallel to the central longitudinal axis 168 of the funnel float body 134. The L-shaped extraction passageway 180 is in open fluid communication with and extends between a tear drop shaped port 188 disposed in the inner hemispherical surface 150 and a circular shaped port 190 disposed in the frustum shaped upper top surface 138. An upper portion 192 of the second branch 184 has an increased diameter proximate the circular shaped port 190 for receiving the lower end 128 of the coiled tube 124 which has its upper end 126 coupled to the barbed end 122 of the barb fitting 114 for providing open fluid communication between the inverted domed shaped cavity 152 and the extraction valve 100.

Float Cap 194

Referring now to FIGS. 10 through 13, the funnel and isolation float 132 is further comprised of the float cap 194 which comprises a circular bottom surface 196, a frustum shaped lower top surface 198, and a float cap circumferential sidewall 200 extending between the circular bottom surface 196 and the frustum shaped lower top surface 198.

The circumferential sidewall 200 includes an outer circumferential or cylindrical surface 202 which extends between a circular outer periphery 204 of the circular bottom surface 196 and a circular outer edge 206 of the frustum shaped lower top surface 198.

The float cap 194 is complementally shaped and sized to fit within the cylindrically shaped cavity 162 of the float body 134 for closing the annular opening 158 of the inverted domed shaped cavity 152 for defining an inverted dome shaped isolation chamber 208 as illustrated in FIG. 6.

Figure 10:
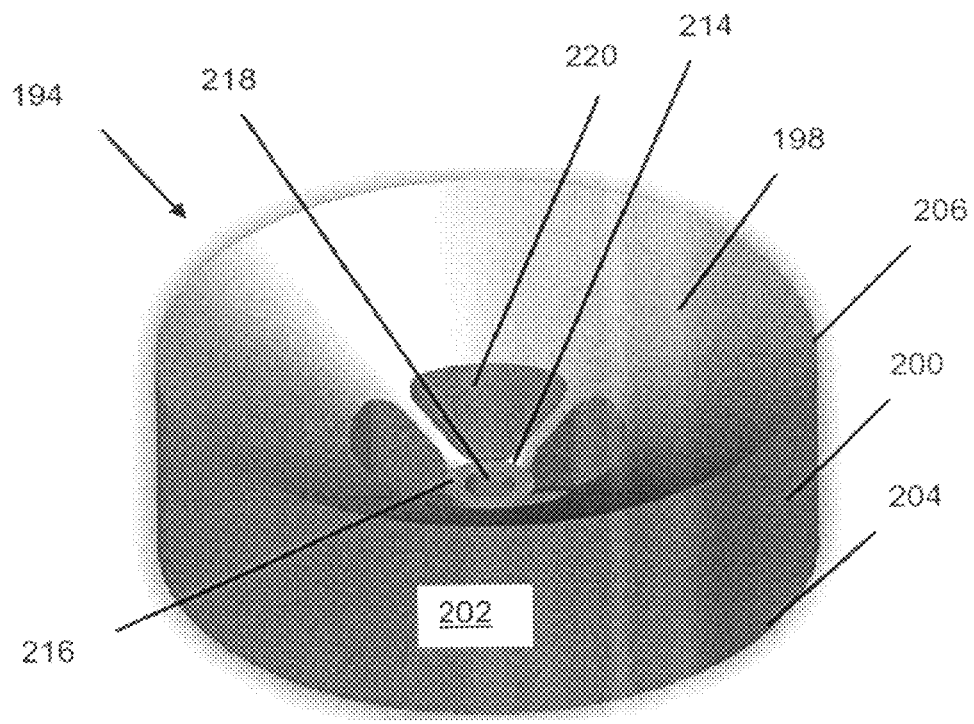
FIG. 10 is a perspective view of an embodiment of a funnel float cap of the funnel float assembly illustrated in FIG. 6.

Additionally, and referring to FIGS. 6 and 10, the frustum shaped lower top surface 198 of the float cap 194 provides a lower continuation of the frustum shaped upper top surface 138 of the float body 134 for defining a conical or funnel shaped surface 210 of the funnel and isolation float 132 which, in turn, defines a conical or funnel shaped cavity 212. In one embodiment, the frustum shaped upper top surface 138 and lower top surface 198 are continuous with one another such that the funnel shaped surface 210 uniformly tapers from the circular outer edge 146 of the frustum shaped upper top surface 138 to a lower annular edge 214 of the frustum shaped lower top surface 198. In another embodiment, the lower top surface 198 may have an accelerated tapering.

The funnel shaped surface 210 inwardly tapers from the circular outer edge 146 of the frustum shaped upper top surface 138 to the lower annular edge 214 of the frustum shaped lower top surface 198 where the funnel shaped surface 210 transitions into a funnel tube portion 216 of the float cap 194. The funnel tube portion 216 defines a central open ended cylindrical opening 218 which extends through a central area of the float cap 194. In turn, at least one funnel fluid passageway 220 is disposed through the funnel float cap 194 between a funnel port 222 (FIG. 11) disposed in the frustum shaped lower top surface 198 and an entrance port 224 (FIG. 12) disposed in the bottom surface 196 of the float cap at location adjacent the funnel tube portion 216 thereby providing open communication between the funnel shaped cavity 212 and the inverted dome shaped isolation chamber 208. In one embodiment, there are four funnel fluid passageways 220 connected between respective ports 222, 224 and equally spaced apart at ninety degree intervals around funnel tube portion 216.

Figure 11:
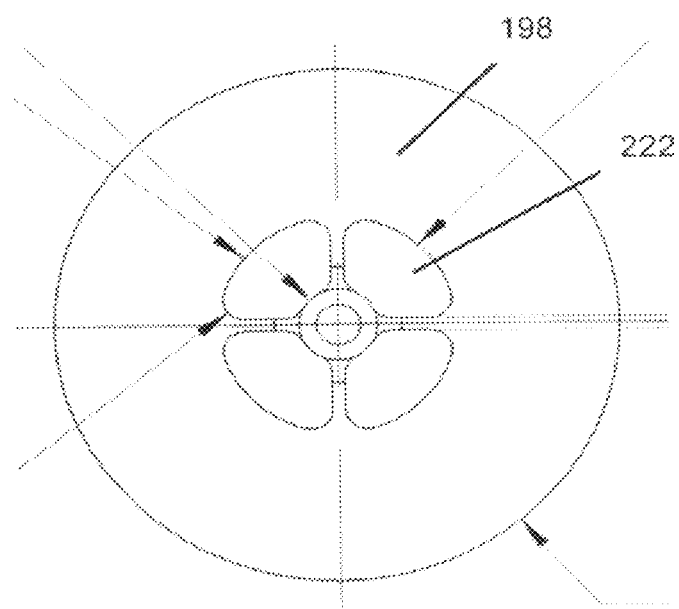
FIG. 11 is a top plan view of the funnel float cap illustrated in FIG. 10.

Additionally, and in one embodiment, the funnel fluid passageways 220 are generally triangular in shape with a concave apex having rounded edges located proximate the funnel tube portion 216 and a convex base having rounded edges located distal from the funnel tube portion 216 as illustrated in FIG. 11. Furthermore, and in one embodiment, the funnel shaped surface 210 has a preferred declivity of about thirty degrees from a plane perpendicular to a central axis 226 (FIG. 13) of the float cap 194. Thus, this provides the funnel face with about a one hundred twenty degree opening.

Figure 12:
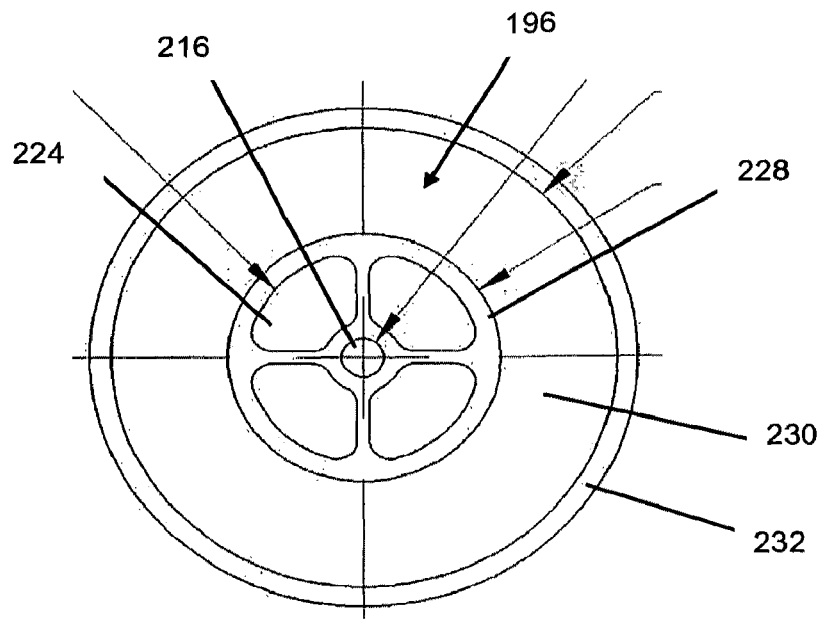
FIG. 12 is a bottom plan view of the funnel float cap illustrated in FIG. 10.
Figure 13:
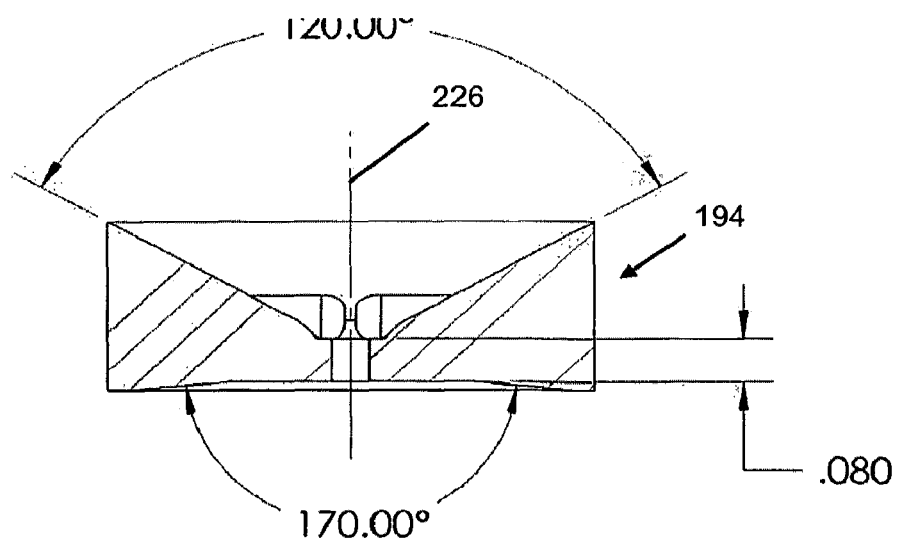
FIG. 13 is a sectional view of the funnel float cap illustrated in FIG. 10.

Furthermore, and referring to FIGS. 12 and 13, one embodiment of the circular bottom surface 196 of float cap 194 is comprised of: a substantially flat surface 228 circumscribing the central open ended cylindrical opening 218 and the plurality of funnel fluid passageways 220, an annular portion 230 transitioning from the surface 228 and having an declivity of about five degrees from a plane perpendicular to the central axis 226 of the funnel cap 134, and a substantially flat annular bottom edge surface 232 transitioning from annular portion 230.

Moreover, the float cap 194 is preferably constructed of, but not limited to, a material which is both biocompatible and stable for gamma irradiation. In one embodiment, the float cap 194 is constructed of, but not limited to, a polystyrene type of material.

Umbrella Valve 234

Figure 14:
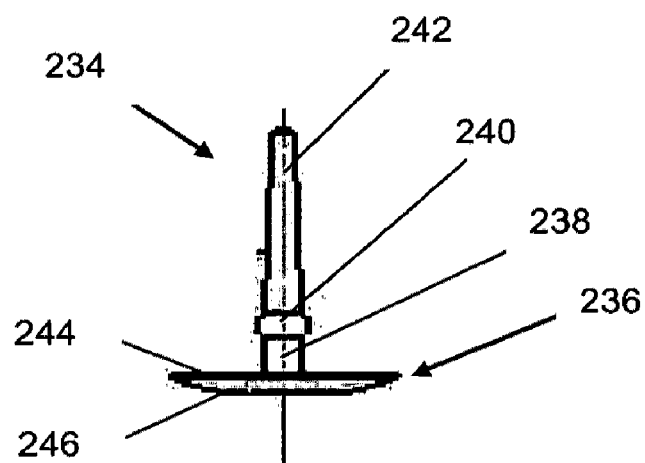
FIG. 14 is a perspective view of an embodiment of an umbrella valve.

Referring to FIGS. 6 and 14, and one embodiment, the float assembly 130 further comprises a first one way valve or check valve in the form of an elastic umbrella valve 234 which is used to selectively open and close the funnel fluid passageways 220 based on a pressure differential of biological fluid on the umbrella valve 234 thereby controlling fluid flow from the funnel shaped cavity 212 to the inverted dome shaped isolation chamber 208 while precluding fluid from flowing back out of the inverted dome shaped isolation chamber 208 to the funnel shaped cavity 212 via the umbrella valve 234. Thus, the umbrella valve 234 provides a unidirectional flow of biological fluid from the second or upper volume zone 262 above the float to the third volume zone or isolation zone defined by inverted dome shaped isolation chamber 208 as a function of the pressure differential of biological fluid on the umbrella valve 234.

More specifically, and in one embodiment, the umbrella valve 234 is comprised of a generally circular canopy or dome 236 which, in an unstressed position, extends generally perpendicularly to a centrally located stem 238. The stem 238 includes a bulbous portion 240 beyond which is a tapered shaft portion 242. In one embodiment, the entire umbrella valve 234 is a one piece, integral construction.

Referring to FIGS. 6, 10, 12, and 14, the umbrella valve 234 is mounted to the float cap 194 by securing the stem 238 through the central open ended cylindrical opening 218 disposed through the float cap 194. This is accomplished by sizing the length of stem 238 between the canopy 236 and the bulbous portion 240 greater than the length of the cylindrical opening 218 and sizing the diameter of the bulbous portion greater than the diameter of the cylindrical opening 218 such that when the tapered shaft portion 242 of the stem 238 is inserted into the cylindrical opening 218 from the bottom surface 196 of the float cap 194 and pulled or stretched away from the frustum shaped lower top surface 198 of the float cap 194 the elastic bulbous portion 240 passes through the central open ended cylindrical opening 218 and resumes its normal shape adjacent the frustum shaped lower top surface 198 of the float cap 194 thereby acting as an anchor for holding the umbrella valve 234 in place. After anchoring the umbrella valve 234 in place, the tapered shaft portion 242 may be trimmed while retaining the bulbous portion 240.

Additionally, the generally circular canopy or dome 236 includes a flat underside contact surface 244 when in the unstressed position. Thus, when the centrally located stem 238 is stretched an axial force is exerted on the canopy or dome 236 such that the underside 244 is drawn into a normal tight, sealing contact against the substantially flat surface 228 of the bottom surface 196 of the float cap 194 for sealing the funnel fluid passageways 220.

With this construction, the elastic umbrella valve 234 provides a one way valve which controls fluid flow into the inverted dome shaped isolation chamber 208 and precludes fluid flow out of the inverted dome shaped isolation chamber 208 via the elastic umbrella valve 234. In particular, the elastic umbrella valve 234 opens under a predetermined pressure differential or cracking pressure or, in other words, when the pressure in the funnel fluid passageways 220 is greater than below or on an outer surface 246 of the canopy or dome 236 by a predetermined or known cracking pressure of the umbrella valve 234. Hence, when there is a positive pressure differential defined by a pressure at the funnel fluid passageways 220 being greater than the pressure on the outer surface 246 of the canopy or dome 236 by an amount which is greater than the cracking pressure then the pressure differential causes the flexible canopy or dome 236 to invert or flex downwardly, away from the bottom surface 196 of the float cap 194 thereby permitting the biological fluid to pass into the inverted dome shaped isolation chamber 208. After the pressure differential resides to a point less than the cracking or opening pressure, the resilient canopy or dome 236 resumes its sealing position under the funnel fluid passageways 220 thereby precluding any further biological fluid from entering the inverted dome shaped isolation chamber 208.

In one embodiment, the umbrella valve 234 is preferably constructed of, but not limited to, a material which is both biocompatible and stable for gamma irradiation. In one embodiment, the umbrella valve 234 is constructed of, but not limited to, a silicone type of material; however, any sufficiently flexible and resilient material may be employed as long as the material is compatible with the biological fluid being processed and preferably, biocompatible and stable for gamma irradiation. One example of the umbrella valve 234 is commercially available as part number 2510-102 from Vernay.

Duckbill Valve 248

Figure 15:
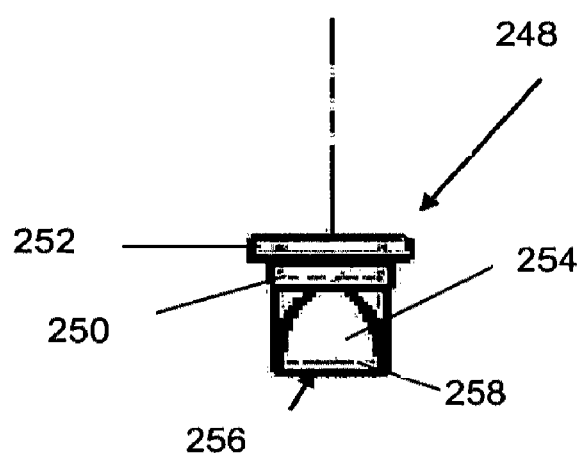
FIG. 15 is a perspective view of an embodiment of a duckbill valve.

Still referring to FIGS. 6, 7, and 15, and one embodiment, the float assembly 130 further comprises a second one way valve or check valve in the form of an elastic duckbill valve 248 which is used to selectively open and close the exit passageway 170 extending between the first circular exit port 172 and the second circular exit port 174 based on a pressure differential of biological fluid on the duckbill valve 248 thereby controlling fluid flow from the inverted dome shaped isolation chamber 208 to the first or lower volume zone 260 while precluding fluid from flowing back into the inverted dome shaped isolation chamber 208 from the first or lower volume zone 260 via the duckbill valve 248. Thus, the duckbill valve 248 provides a unidirectional flow of biological fluid from the isolation zone within the float to the first or lower volume zone 260 as a function of the pressure differential of biological fluid on the duckbill valve 248.

In one embodiment, the duckbill valve 248 is comprised of an open ended hollow cylindrical portion 250 coupled to the exit passageway 170 and transitioning from a radially outwardly projecting annular flange portion 252 to a hollow V-shaped or converging portion 254 which terminates to an elongated outlet slit 256 defined by a pair of resilient sealing lips 258. The resilient sealing lips 258 are formed to move apart to open the slit 256 for fluid to flow in one direction through a fluid passageway axially extending through the duckbill valve 248.

The resilient sealing lips 258 normally maintain the slit 256 in the closed position. When fluid pressure within the hollow V-shaped or converging portion at a location above the sealing lips 258 is greater than a fluid pressure below the resilient sealing lips 258 by a predefined cracking pressure of the duckbill valve 248 then the resilient sealing lips 258 spreading and the slit 256 open thereby permitting fluid to flow downwardly through the exit passageway or aperture 170 and through the axially extending fluid passageway of the duckbill valve 248. The outlet slit 256 closes when the fluid pressure below or on the outer surfaces of the resilient sealing lips 258 is higher than the fluid pressure above the resilient sealing lips 258 by more than the cracking pressure of the duckbill valve 248 thereby preventing the backflow of fluid through the duckbill valve. Additionally, if fluid flow stops or reverses direction, the back-pressure exerted by the fluid upon the outer surfaces of the resilient sealing lips 258 forces the lips into sealing engagement against one another, closing outlet slit 256 and preventing fluid backflow.

As assembled, the annular flange portion 252 of the duckbill valve is seated within the annular recessed area 178 disposed through the bottom surface 136 of the float body 134 while the hollow cylindrical portion 250 fits over the annular shoulder 176 such that the exit passageway 170 is in open communication with the axially extending fluid passageway of the duckbill valve 248 and such that a press type fit or coupling is provide between the duckbill valve 248 and annular shoulder 176 of the float body 134 to maintain a seal between the duckbill valve 248 and the float body 134.

In one embodiment, the duckbill valve 248 is preferably constructed of, but not limited to, a material which is both biocompatible and stable for gamma irradiation and is constructed of, but not limited to, a silicone type of material; however, any sufficiently flexible and resilient material may be employed as long as the material is compatible with the biological fluid being processed and preferably, biodegradable and stable for gamma irradiation. One example of this embodiment of the duckbill valve is commercially available as part number DU 054.001-154.01 from MiniValve International.

Use and Operation

Figure 16:
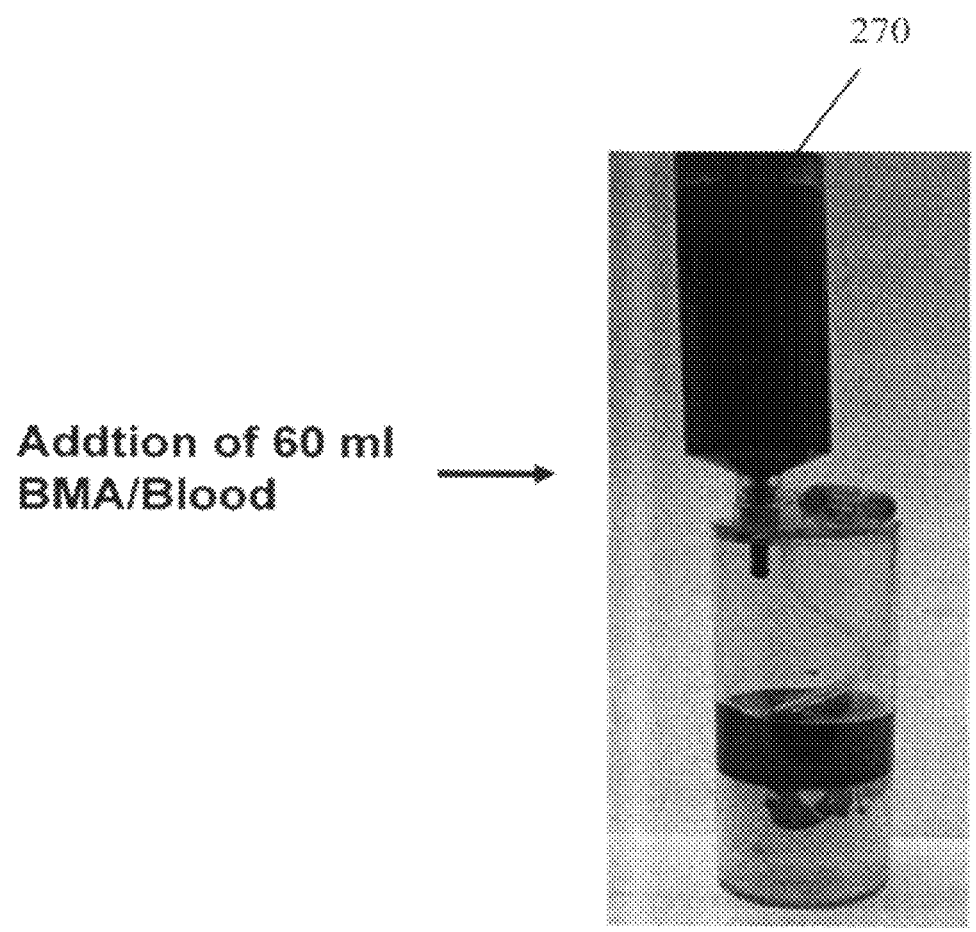
FIG. 16 is a perspective view of the device being filled with a biological fluid.

In use and operation, and referring to the drawings, the device 10 initially receives a multiple component biological fluid sample (e.g., peripheral blood, bone marrow aspirate, blood components, cord blood, apheresis blood products, lipo-aspirate, semen, urine, milk, ascites fluid, exudate or cerebrospinal fluids) by performing the steps of removing the cap 85 from the male luer lock head 88 of the inlet valve 86, coupling a conventional needleless syringe 270 or other dispensing device containing the biological fluid sample to the male luer lock head 88 of the inlet valve 86, injecting or dispensing the biological fluid sample into the device 10 from the conventional syringe 270 or other dispensing device (FIG. 16), decoupling the conventional syringe 270 or other dispensing device from the male luer lock head 88 of the inlet valve 86, and reattaching cap 85. When supplying the device 10 with biological fluid, the air filter allows air to escape from the enclosure 48.

Figure 17:
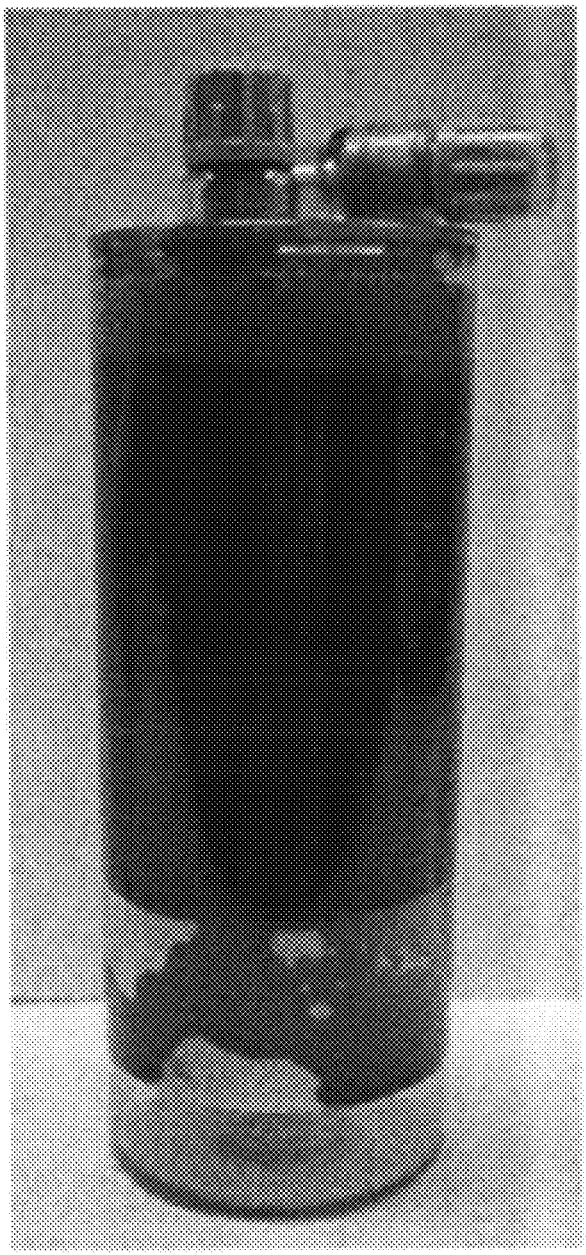
FIG. 17 is a perspective view of the device after being filled with the biological fluid and before centrifugation.

The received biological fluid sample fills the second or upper volume zone 262 above the inverted dome shaped isolation chamber 208 including the funnel shaped cavity 212 and flows to the first or lower volume zone 260 below the float assembly 130 via the circumferential gap 148 disposed between the outer circumferential surface 142 of the float sidewall 140 and the inner circumferential surface 24 of the tube 12 as illustrated in FIG. 17. The biological fluid sample is initially precluded from entering or passing through the inverted dome shaped isolation chamber 208 by the normally closed umbrella valve 234 and the normally closed duckbill valve 248. Additionally, the circular top edge 38 of the standoff member 34 abuts the circular bottom surface 136 of the float body 134 of the float assembly 130 for providing an initial lift off the float assembly 130 from the interior surface 30 of the closed bottom end 14 of the tube 12 for precluding a vacuum seal from forming therebetween while also protecting the elastic duckbill valve 248 in the cylindrically shaped receiving chamber 46 of the standoff member 34 under initial conditions.

Once the biological fluid sample has been received within the enclosure 48 defined by the tube 12 and tube cap 50, the device 10 is placed in a conventional centrifugation device 280 which is operated for one or more predetermined durations at one or more predetermined speeds. In one embodiment, and for a biological fluid sample exemplified by blood, the conventional centrifugation device 280 is operated for about 12 to about 15 minutes at about 3,200 RPM. Of course, one or more time durations and one or more speeds can be empirically determined for a specific biological fluid to be processed by the device 10 and may vary from one biological fluid to another.

Upon initial centrifugation of the device 10, the biological fluid in the funnel shaped cavity 212 increasingly applies a pressure on the umbrella valve 234 which results in a pressure differential on the umbrella valve 234 becoming greater than the cracking pressure of the umbrella valve 234 thereby allowing fluid to flow through one or more of the funnel fluid passageways 220 and into the inverted dome shaped isolation chamber 208 which begins to fill and apply a second pressure on the duckbill valve 248 which results in a pressure differential on the duckbill valve 248 being greater than the cracking pressure of the duckbill valve 248 thereby allowing biological fluid to initially flow out of the inverted dome shaped isolation chamber 208 via exit passageway 170. At first, the biological fluid quickly flows through the inverted dome shaped isolation chamber 208 and when the sample is blood the hematocrit is initially not concentrated. With both the umbrella valve 234 and duckbill valve 248 in an open position, the building of the column of biological fluid in the first or lower volume zone 260 or below the float assembly 130 continues. As this column of the biological fluid builds, the device 10 provides a unique circulation process or density feedback process which will be clearly delineated by using peripheral blood as an example of the biological fluid being processed.

Accordingly, and as the biological fluid such as peripheral blood stratify based on density and the components build the column, the cells that are just below the bottom surface 136 of the float body 134 also continue to stratify such that the cell density above the level of the duckbill valve 248 is less than the cell density below the level of the duckbill valve 248 by an amount which provides a pressure differential which is less than the cracking pressure of the duckbill valve 248 thereby resulting in the closure of the duckbill valve 248 such that over time the reds cells accumulate at the bottom section 154 of the inverted dome shaped isolation chamber 208 and become packed and thus, there are packed cells at the bottom section 154 of the chamber which have a greater density than the cells right below the level of the duckbill valve 248 because at the same time that the density of red cells is increasing at the bottom section 154 the density right below the duckbill valve 248 is decreasing because greater density cells are also migrating toward the bottom end 14 of the tube 12. Thus, as this density increases a pressure differential builds to surpass the cracking pressure of the duckbill valve 248 which then opens thereby allowing the red cells to flow through the exit passageway 170 and displace the biological fluid in the first or lower zone 260 which, in turn, pushes fluid up or causes a surge of fluid up through the circumferential gap 148 between the outer circumferential surface 142 of the float sidewall 140 and the inner circumferential surface 24 of the tube 12. This upward fluid flow has the effect of carrying the lighter components of the biological fluid including the white blood cells and platelets from the first or lower volume zone 260 of the tube 12 back up to the second or upper volume zone 262 of the tube 12 wherein these lighter components are heavier than the plasma in the second or upper volume zone 262 that they got circulated into so the white blood cells and platelets or buffy coat included therein fall back down through the funnel shaped cavity 212, past the umbrella valve 234, and collect in the inverted dome shaped isolation chamber 208. This cell circulation process or density feedback process continues on towards an equilibrium where the pressure differential or the density differential of the cells above and below duckbill valve 248 is less than the cracking pressure of the duckbill valve 248 resulting in the duckbill valve 248 having a final closure and similarly the density differential of the cells above and below umbrella valve 234 is less than the cracking pressure of the umbrella valve 234 resulting in the umbrella valve 234 having a final closure thereby concluding the unique cell circulation process or density feedback process of the device 10.

Hence, this cell circulation process or density feedback process allows multiple chances at capturing the white cells or other target components of interest in the inverted dome shaped isolation chamber 208 thereby providing higher recovery rates as compared to know prior art devices.

Figure 18:
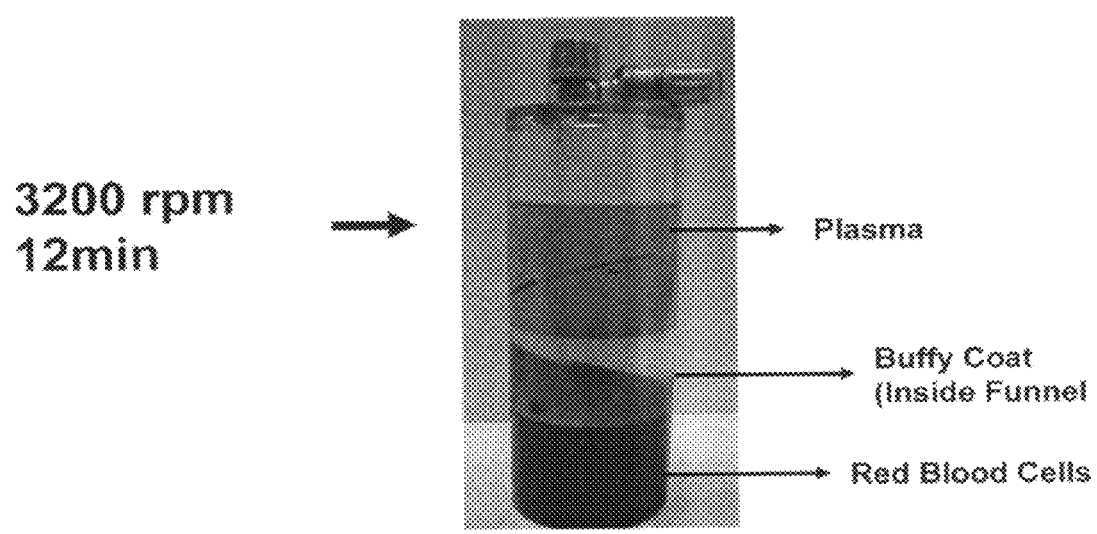
FIG. 18 is a perspective view of the device after a centrifugation process.
Figure 20:
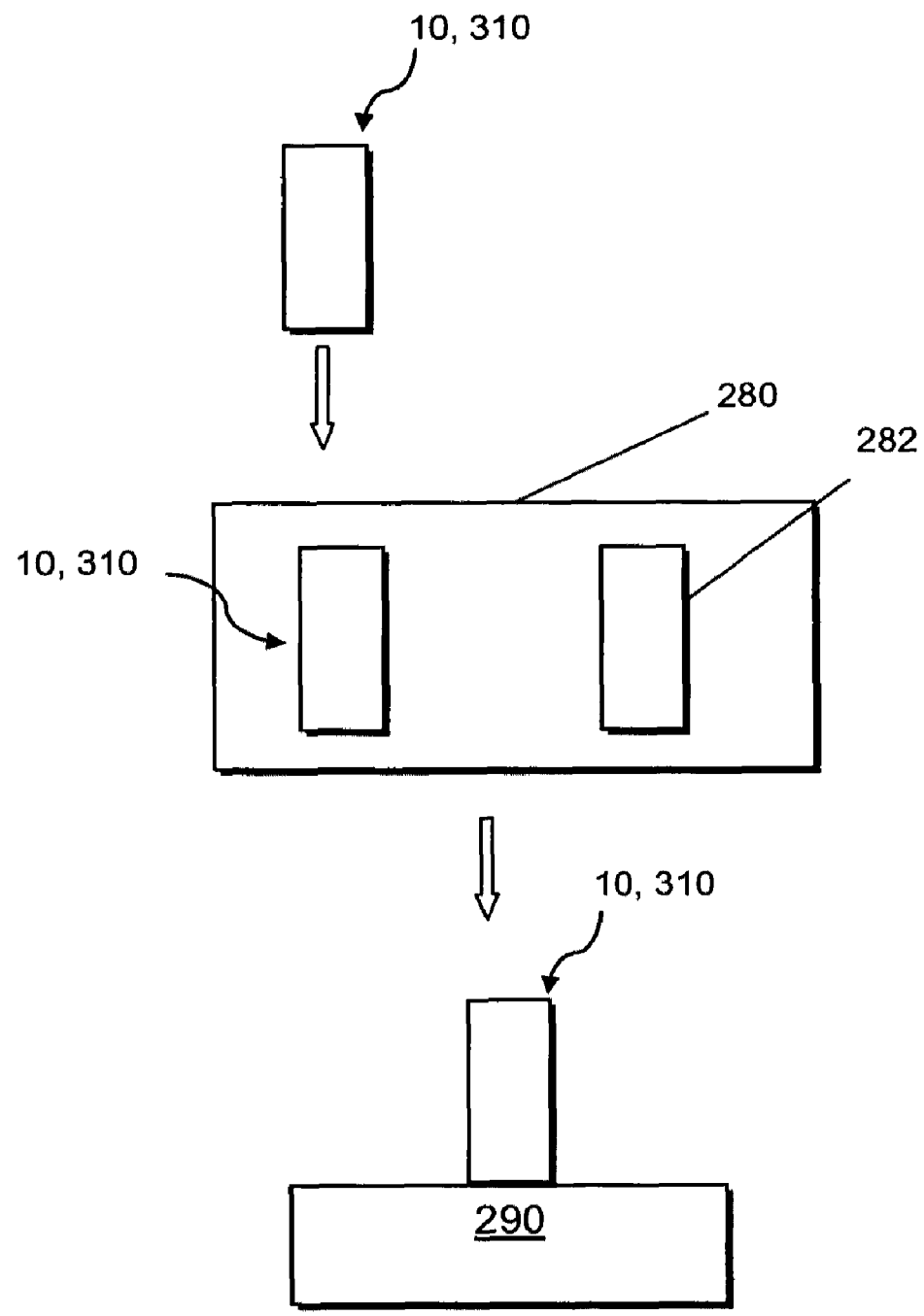
FIG. 20 is a block diagram of a conventional centrifuge and stirrer being employed with the device.

Following the centrifugation step, the device 10 containing the separated and isolated biological fluid components is removed from the centrifugation device 280 (FIG. 18) and placed on a conventional magnetic stirrer 290 as diagrammatically shown in FIG. 20. The stirrer is then energized for activating or coacting with a magnetic stirring bar 292 located inside the inverted dome shaped isolation chamber 208 for stirring at least one isolated target component within the isolation chamber 208 for increasing a recovery rate of a subsequent harvesting step. In one embodiment, at least the one isolated target component or fraction is stirred for about twenty seconds. Of course, stirring times may vary from one biological fluid to another and a specific stirring time for a specific biological fluid can be empirically determined.

Figure 19:
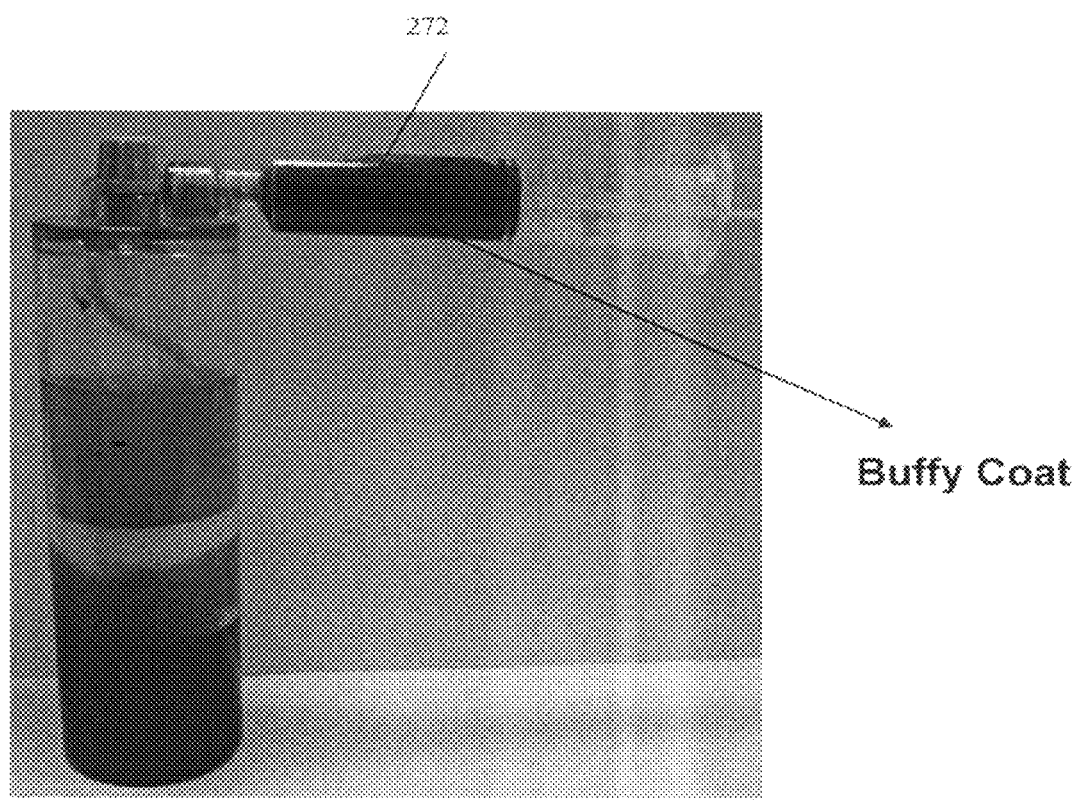
FIG. 19 is a perspective view of an isolated target component being harvested from the device.

Following the stirring step, the harvesting step of at least the one isolated target component or fraction is performed and is comprised of the steps of removing the cap 99 from the male luer lock head 102 of the extraction valve 100, coupling a conventional syringe 272 or other extraction device to the male luer lock head 102 of the extraction valve 100, aspirating at least the one isolated target component or fraction from the inverted dome shaped isolation chamber 208 by providing a vacuum from the syringe 103 to the tear drop shaped port 188 disposed in the radiused bottom section 154 of the inner hemispherical surface 150 and aspirating at least the one isolated target component or fraction from the inverted dome shaped isolation chamber 208 and through the tear drop shaped port 188 and into and through the exit L-shaped extraction passageway 180 disposed in the float body 134, the coiled tube 124, the barb fitting 114, the L-shaped housing passageway 62, the extraction valve 100, and finally into the conventional syringe 272 (FIG. 19).

After the harvesting step is completed, the conventional syringe 103 is decoupled from the male luer lock head 102 of the extraction valve 100 in preparation for at least one diagnostic or therapeutic application of at least the one target component or fraction. When harvesting at least the one target component or fraction, the air filter allows air into the enclosure 48. Additionally, when the cracking pressure of the umbrella valve is reached during a harvesting step, plasma flows into the inverted dome shaped isolation chamber 208 to displace the removed volume of at least the one target component or fraction.

It should be noted that a counter weight device 282 may be used in the conventional centrifugation device 280 to offset the weight of the device 10 containing biological fluid as required.

Furthermore, device 10 should be assembled in an environment to minimize the risk of particulate matter in the fluid path and when used for clinical applications, the device 10 must be sterilized and the fluid path should be non-pyrogenic.

Device 310

Figure 22:
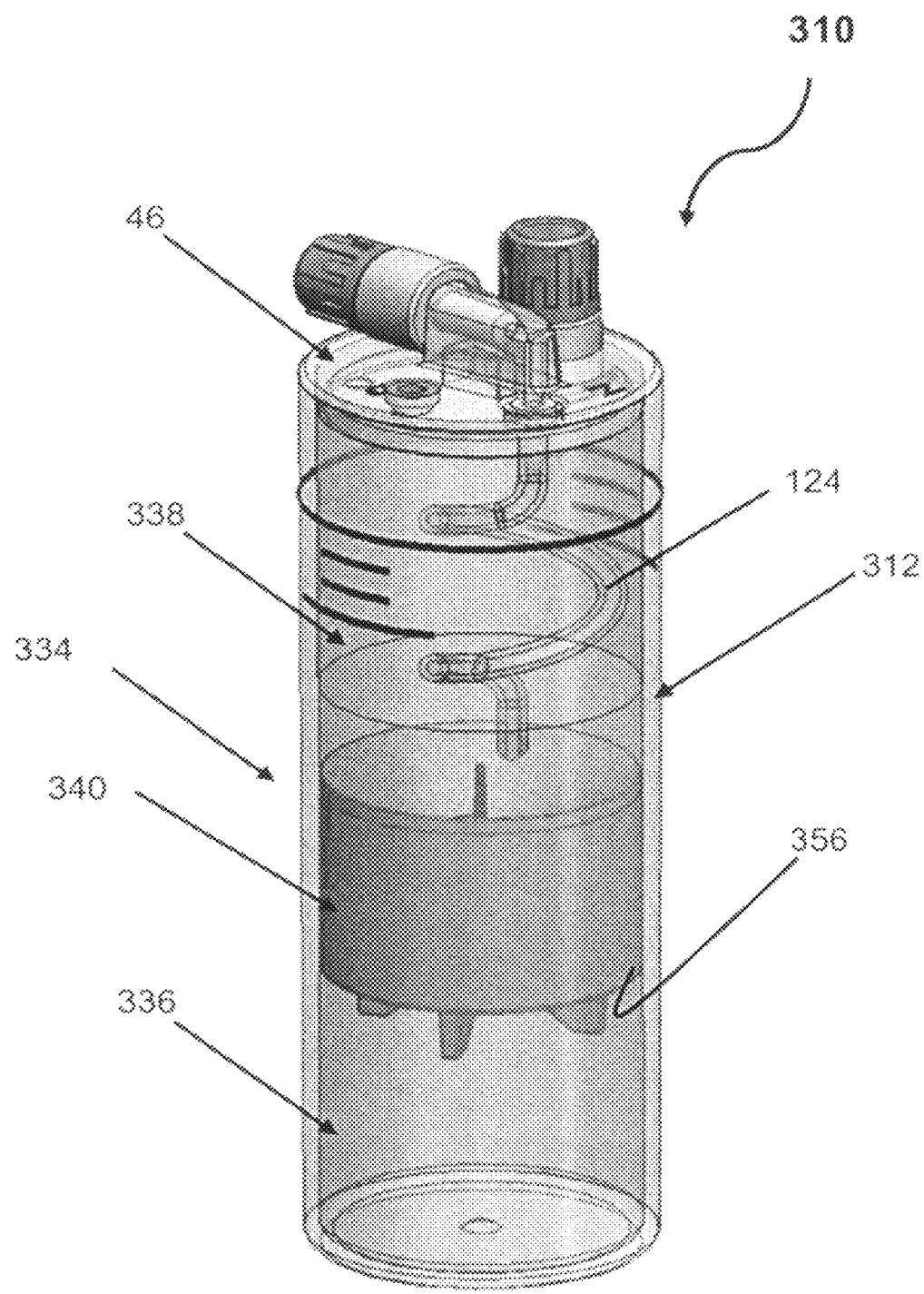
FIG. 22 is a perspective view of another embodiment of the device for separating and isolating components of a biological fluid.
Figure 23:
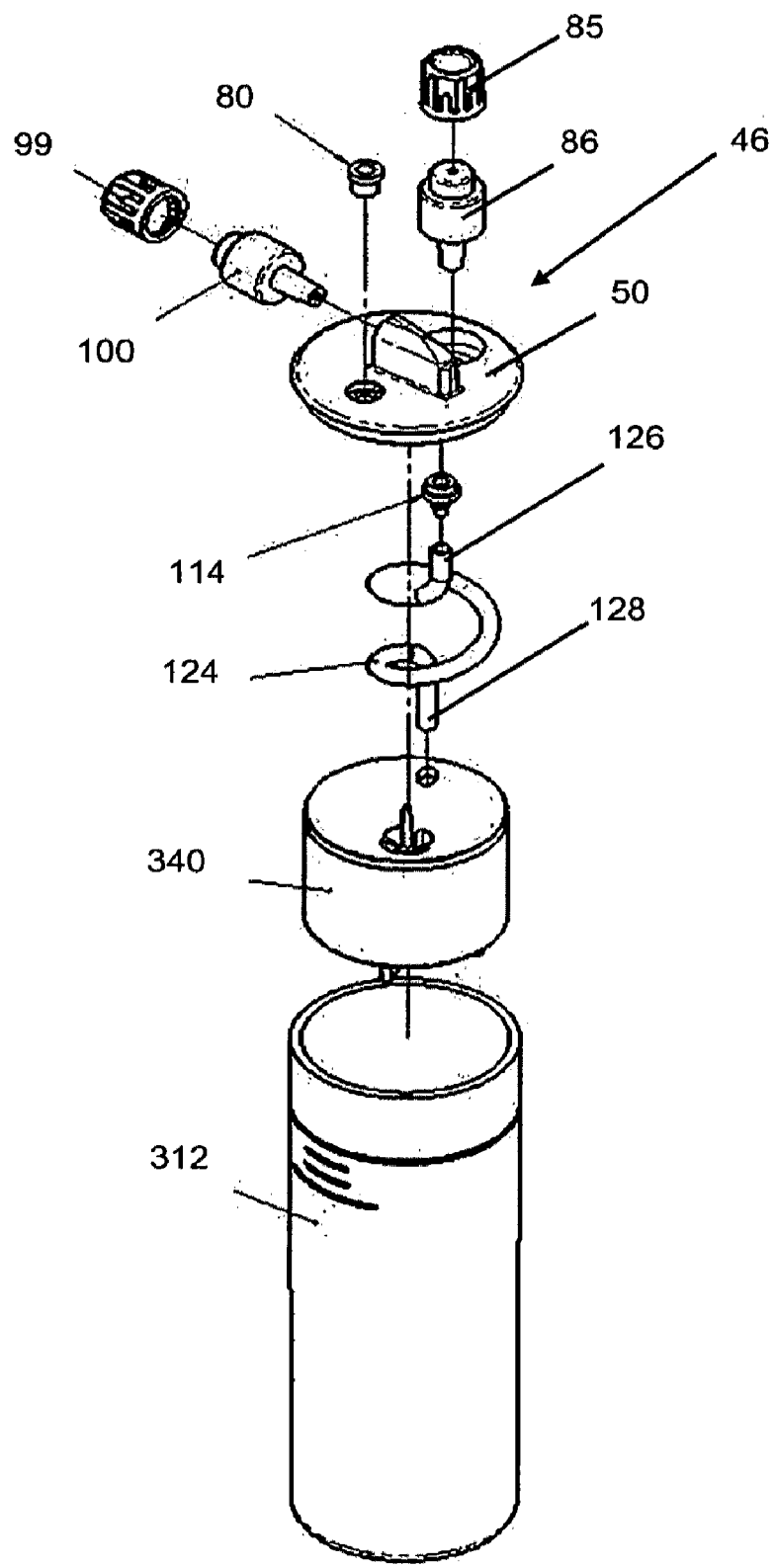
FIG. 23 is an exploded parts perspective view of the device illustrated in FIG. 22.

Referring now to FIGS. 22 and 23, and in one embodiment, the device 310 is comprised of a main centrifuge tube or container 312; the tube cap assembly 46 (also detailed in FIGS. 3 through 5) for selectively closing the container 312 for defining an enclosure 334 for receiving and containing a biological fluid having multiple components; a dual density subsurface funnel and isolation float assembly 340 which is slideably disposed within the container 312 and which partitions the enclosure 334 into a first or lower volume zone 336 below the float assembly 340, a second or upper volume zone 338 above the float assembly 340, and an isolation or third volume zone defined by an isolation chamber 378 within the float assembly 340 as further delineated hereinbelow; and the flexible tube 124 (also detailed in FIG. 1) operatively coupled between the float assembly 340 and the tube cap assembly 46 for traveling up or down with the float assembly 340 by coiling or elongating respectively.

Main Centrifuge Tube 312

Figure 24:
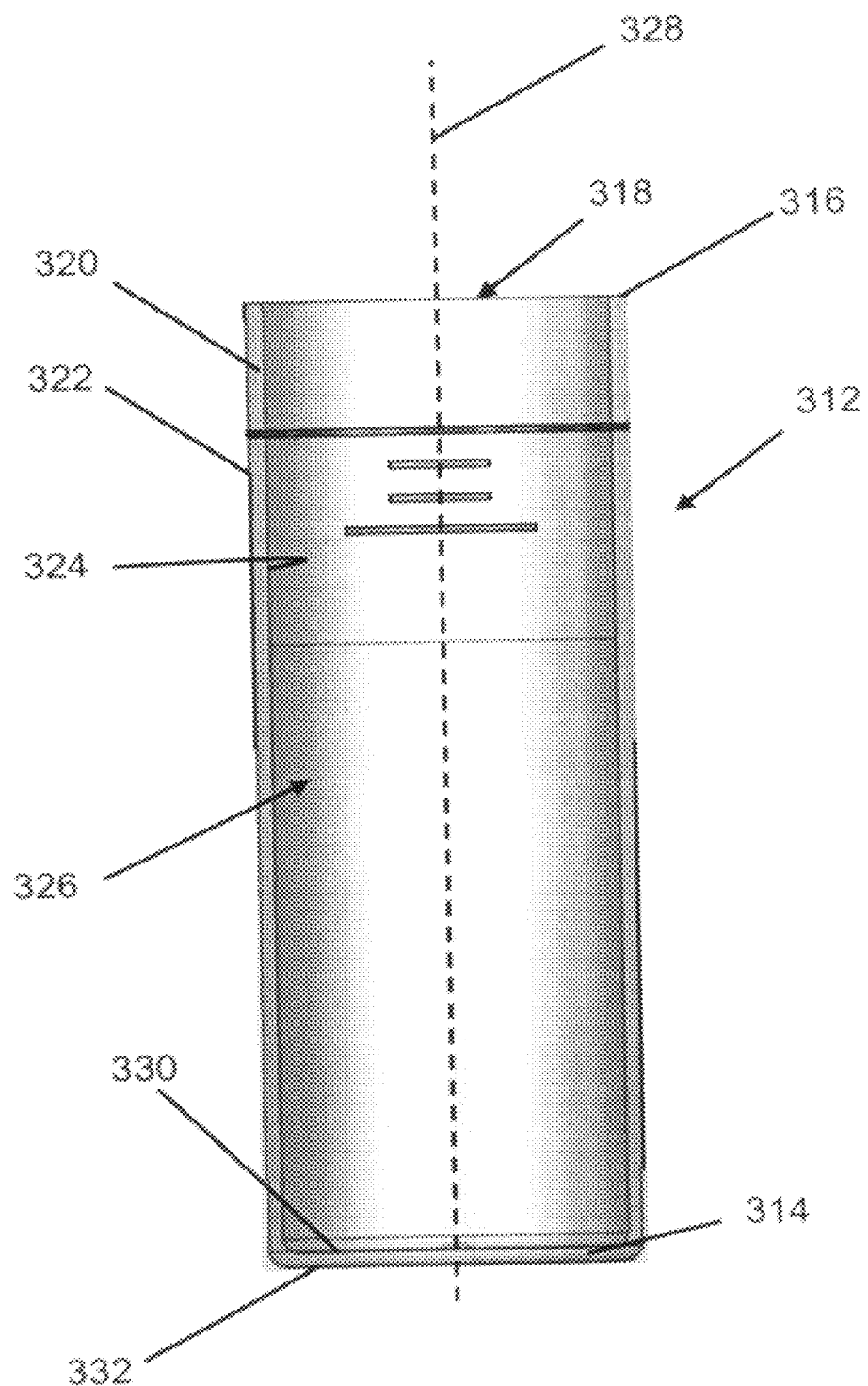
FIG. 24 is a sectional view of another embodiment of a main centrifuge tube.

More specifically, and referring to FIG. 24, the device 310 is comprised of the main centrifuge tube or container 312 which comprises a closed substantially flat annular bottom end 314, a substantially flat annular top edge 316 defining an open top end 318, and a cylindrical sidewall 320 extending between the closed bottom end 314 and the annular top edge 316. The cylindrical sidewall 320 includes an outer cylindrical surface 322 and an inner circumferential or cylindrical surface 324 which defines a cylindrically shaped containing chamber 326 extending along a central longitudinal axis 328 of the tube 312 which is also the central longitudinal axis of the device 310.

In one embodiment, the closed bottom end 314 is substantially formed as a disk shaped member having an interior surface 330 and an exterior surface 332. The interior surface 330 includes an inner radiused edge transitioning into the inner cylindrical surface 324 of the cylindrical sidewall 320. Similarly, the exterior face 332 includes an outer radiused edge transitioning into the outer cylindrical surface 322 of the cylindrical sidewall 320.

Additionally, the closed bottom end 314 may be selectively closeable or integrally formed with the cylindrical sidewall 320.

Furthermore, the tube is preferably constructed of, but not limited to, a material which is both biocompatible and stable for gamma irradiation. In one embodiment, the tube 312 is constructed of, but not limited to, a polycarbonate or polystyrene material.

Tube Cap Assembly 48

Referring to FIGS. 22 and 23, and back to FIGS. 3 through 5, the device 310 is further comprised of the tube cap assembly 48 which is as delineated in detail hereinabove and which will not be repeated so as to not burden the record.

Float Assembly 340

Figure 25:
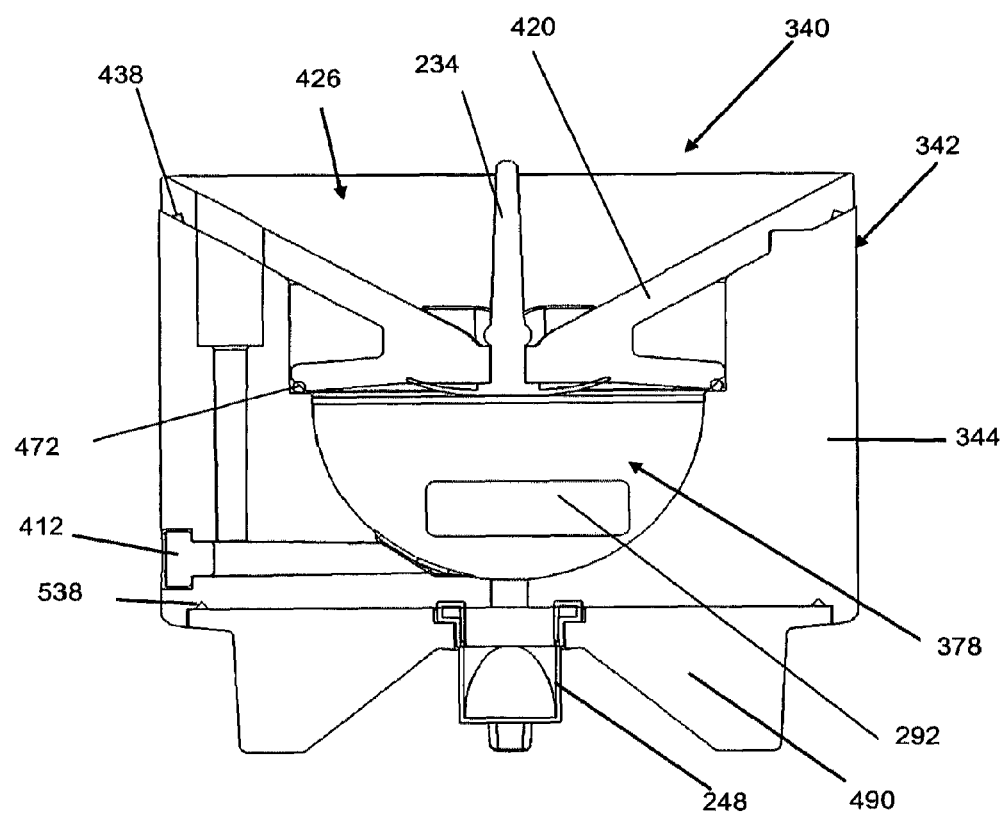
FIG. 25 is a sectional view of another embodiment of a funnel float assembly.
Figure 26:
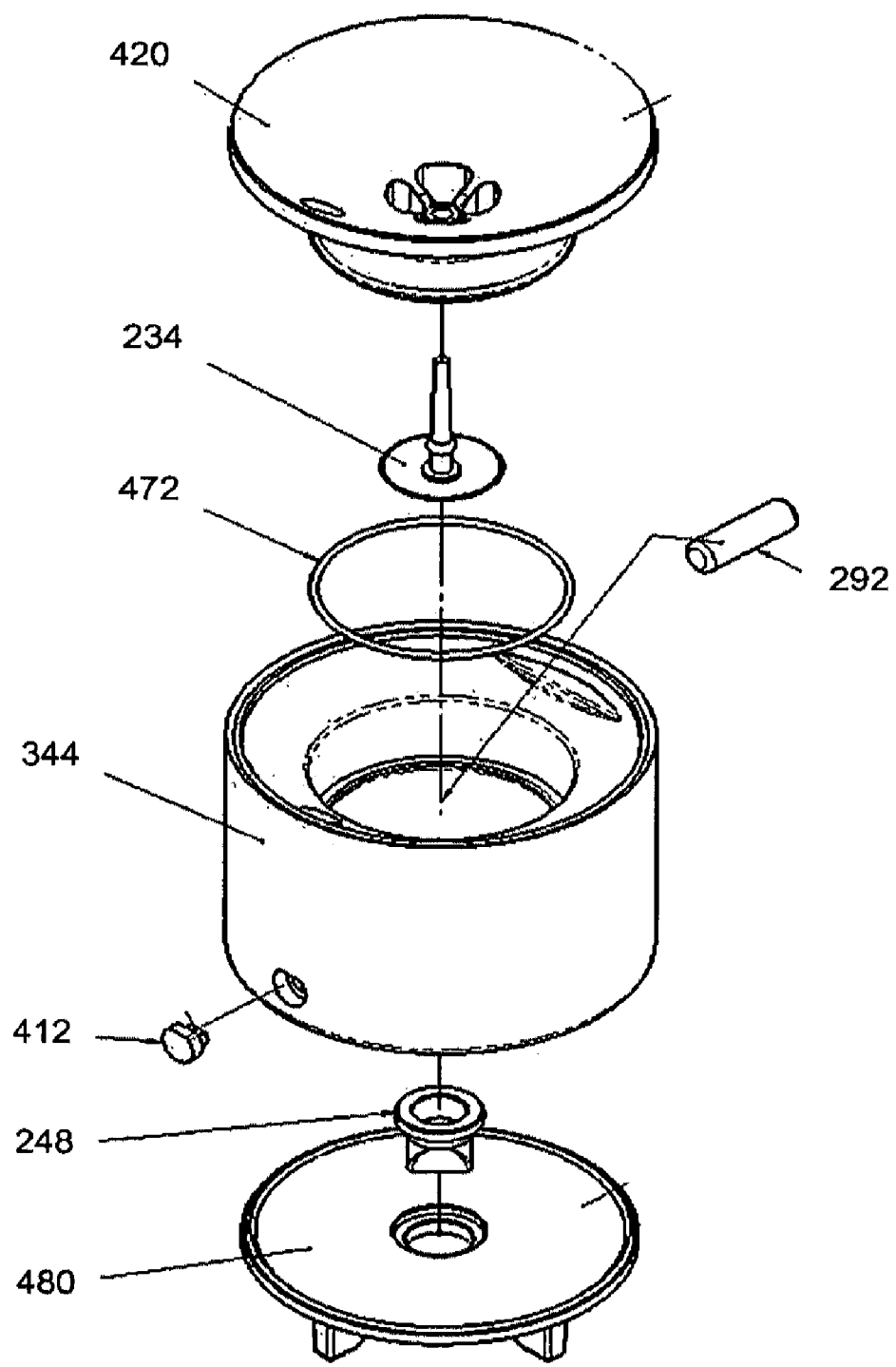
FIG. 26 is an exploded parts view of the funnel float assembly illustrated in FIG. 25.

Referring now to FIGS. 25 and 26, and as noted hereinabove, the device 310 is further comprised of the float assembly 340 which comprises a funnel and isolation float 342 comprised of a float body 344, a funnel float cap 420, and a bottom float cap 480 or 500. Because the funnel and isolation float 342 should be made with precision, it is preferable to make the funnel and isolation float 342 in subcomponents comprised of the float body 344, funnel float cap 420, and the bottom float cap 480 or 500 to facilitate precision injection molding and it is also preferable that the subcomponents be assembled using sonic welding devices or other reliable means.

The float assembly 340 further comprises the first check valve means which, in one embodiment, is in the form of the umbrella valve 234 detailed in FIG. 14; and the second check valve means which, in one embodiment, is in the form of the duckbill valve 248 detailed in FIG. 15.

Float body 342

Figure 27:
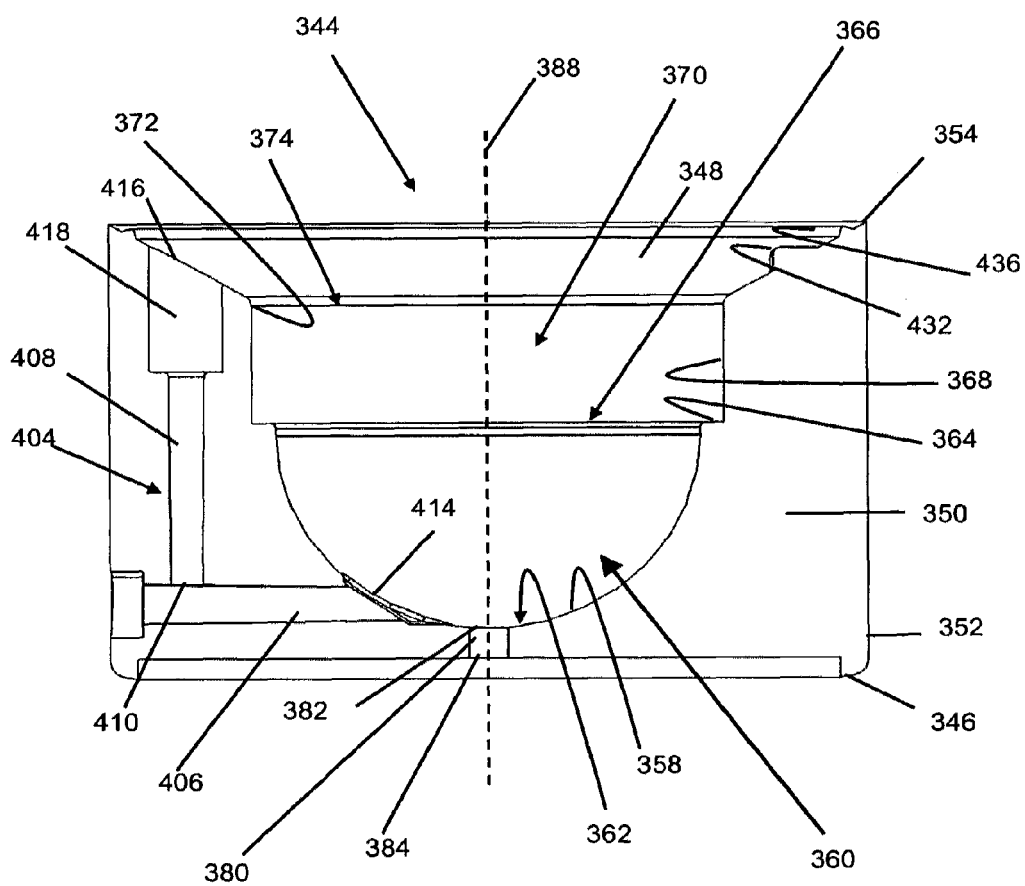
FIG. 27 is a sectional view of an embodiment of a float body of the funnel float assembly illustrated in FIG. 25.

More specifically, and referring to FIGS. 25 through 27, the float body 344 comprises an annular bottom edge 346, a frustum shaped top surface 348, and a float body sidewall 350 extending between the annular bottom edge 346 and the frustum shaped upper top surface 350.

The float body sidewall 350 includes an outer circumferential or cylindrical surface 352 extending between the annular bottom edge 346 and a circular outer periphery 354 of the frustum shaped top surface 348. The outer circumferential surface 352 of the float body sidewall 350 defines a diameter that is less than a diameter defined by the inner circumferential surface 324 of the main centrifuge tube 312 for defining a circumferential gap 356 between the outer circumferential surface 352 of the float body sidewall 350 and the inner circumferential surface 324 of the tube 312.

Additionally, the float body sidewall 350 includes an inner hemispherical surface 358 defining an inverted domed shaped or hemispherical shaped cavity 360 extending from a radiused bottom section 362 of the hemispherical surface 358 to an upper annular ledge 364 defining an annular opening 366 of the inverted domed shaped cavity 360. The upper annular ledge 364 transitions into an inner cylindrical surface 368 defining an open ended cylindrically shaped cavity 370 surmounting the inverted domed shaped cavity 360 such that the annular opening 366 also defines a lower opening of the cylindrically shaped cavity 370. In turn, the inner cylindrical surface 368 extends from the annular ledge 364 to a circular inner edge 372 of the frustum shaped top surface 348. The circular inner edge 372 circumscribes and defines an annular opening 374 between the cylindrically shaped cavity 370 and the frustum shaped top surface 348 such that the opening 374 defines an upper opening of the cylindrically shaped cavity 370 and a lower opening of the frustum shaped top surface 348.

Float body 344 is preferably constructed of, but not limited to, a material which is both biocompatible and stable for gamma irradiation. In one embodiment, the float body 344 is constructed of, but not limited to, a polystyrene or polycarbonate type of material.

Exit Aperture 380

Figure 28:
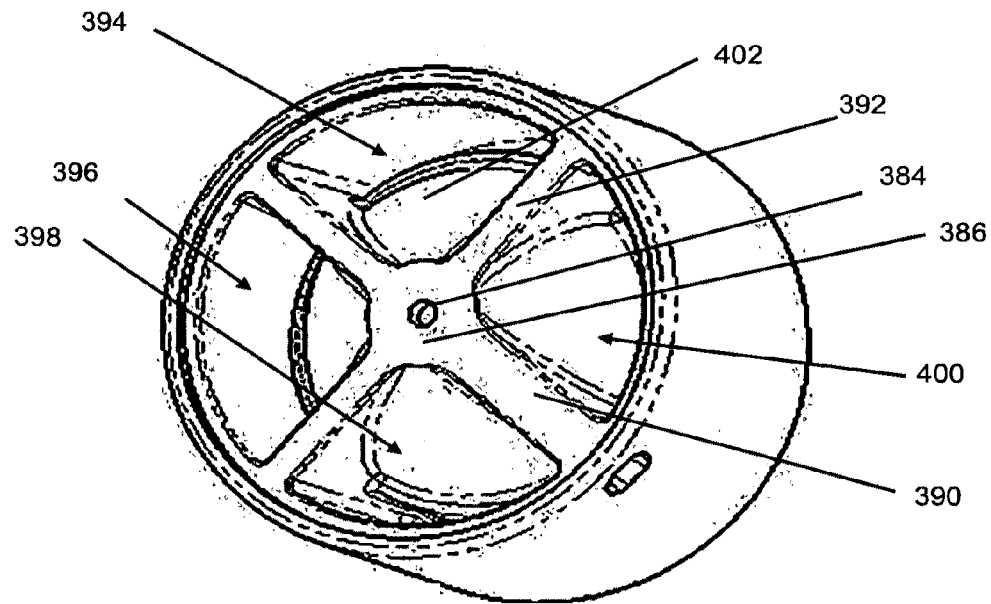
FIG. 28 is a bottom perspective view of the float body illustrated in FIG. 27.

Referring to FIGS. 27 and 28, the float body 344 further comprises an exit aperture or passageway 380 extending between a first circular exit port 382 disposed in the radiused bottom section 362 of the inner hemispherical surface 358 of the float body 344 and a second circular exit port 384 disposed in a bottom surface 386 of the float body 344 for providing open fluid communication between the inverted domed shaped cavity 360 and the first or lower volume zone 336 below the float assembly 340.

Additionally, the first and second circular exit ports 382, 384 have a common axis defined by a central longitudinal axis 388 of the float body 344.

Furthermore, the second circular exit port 384 is disposed in the bottom surface 386 of the float body 344 at a location which is recessed from the annular bottom edge 346 of the float body sidewall 350 and which defines an intersection of two diametrically extending and intersecting cross members 390, 392 defining four spaced apart cavities 394, 396, 398, and 400 in the bottom surface 386 of the float body 344. The four spaced apart cavities 394, 396, 398, and 400 reveal a lower outer surface 402 of the inverted domed shaped cavity 360.

Extraction Aperture 404

Figure 29:
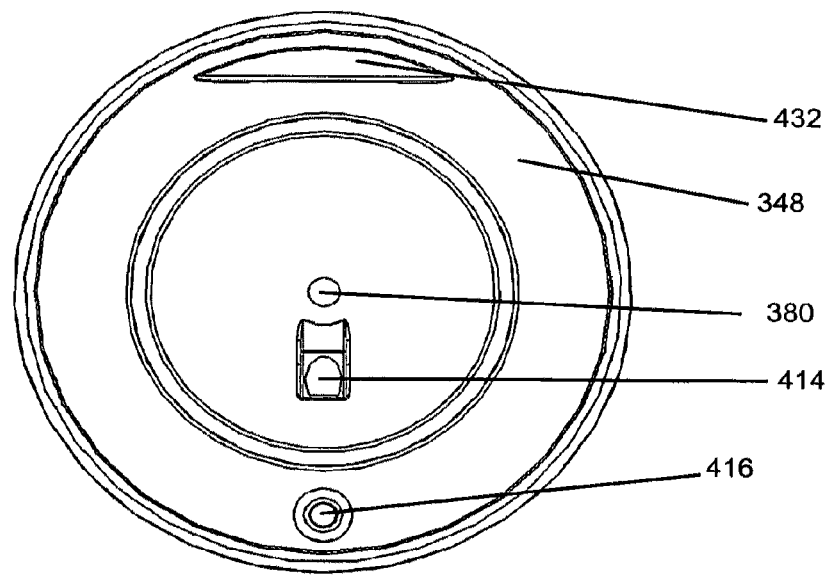
FIG. 29 is a top plan view of the float body illustrated in FIG. 27.

Referring now to FIGS. 27 and 29, the float body 344 further comprises an extraction aperture 404 which, in one embodiment, is an L-shaped extraction passageway 404 defined by a first branch 406, a second branch 408, and a branch bend 410 therebetween. The first branch 406 is formed by providing a bore through the float body sidewall 350 at an angle substantially perpendicular to the central longitudinal axis 388 of the float body 344 wherein a portion of the float body sidewall 350 adjacent the outer circumferential surface 352 is plugged thereafter with plug 412 as illustrated in FIG. 25. The second branch 408 is formed by providing a bore through both the frustum shaped top surface 348 and the float body sidewall 350 which terminates in the first branch 406 at bend 410 and which is at an angle substantially parallel to the central longitudinal axis 388 of the float body 344. The extraction aperture or L-shaped extraction passageway 404 is in open fluid communication with and extends between and an oval shaped port 414 disposed in the inner hemispherical surface 358 and a circular shaped port 416 disposed in the frustum shaped top surface 348. An upper portion 418 of the second branch 408 has an increased diameter proximate the circular shaped port 416 for receiving the lower end 128 of the coiled tube 124 which has its upper end 126 coupled to the barbed end 122 of the barb fitting 114 for providing open fluid communication between the inverted domed shaped cavity 360 and the extraction valve 100.

Funnel Float Cap 420

Referring now to FIGS. 30 through 33, the funnel and isolation float 342 is further comprised of the funnel float cap 420 which comprises a frustoconical or funnel shaped wall 422 transitioning into and mounting a cylindrically shaped neck 460 transitioning into and mounting a disked shaped base 470. The funnel shaped wall 422 includes a frustoconical or funnel shaped upper surface 424 which defines a conical or funnel shaped cavity 426. The funnel shaped wall 422 further includes a frustoconical or funnel shaped lower surface 428 and an outer circumferential or cylindrically shaped peripheral edge 430 extending between the frustoconical or funnel shaped upper and lower surfaces 424, 428.

The disked shaped base 470 is complementally shaped and sized to fit within the cylindrically shaped cavity 370 of the float body 344 and when fitted therein, an elastomeric o-ring 472 is captured between a lower peripheral chamfer 474 of the disk shaped base 470 and the annular ledge 364 for providing a seal therebetween and for closing the annular opening 366 of the inverted domed shaped cavity 360 for defining an inverted dome shaped isolation chamber 378 as illustrated in FIG. 25. Additionally, the funnel shaped lower surface 428 of the funnel shaped wall 422 is complementally shaped and sized to abut against the frustum shaped top surface 348 of the float body 344 when the elastomeric o-ring 472 is sealed against the annular ledge 364.

When the disked shaped base 470 is properly fitted within the cylindrically shaped cavity 370 of the float body 344 as delineated above, an alignment and interlocking means is provided between the funnel float cap 420 and the float body 344. Specifically, and referring to FIGS. 25, 27, and 31, a circular segment 432 protruding from the frustum shaped top surface 348 of the float body 344 is received within a circular segment indentation 434 disposed through the funnel shaped lower surface 428 and into the funnel shaped wall 422 such that the protruding circular segment 432 aligns and interlocks with the circular segment indentation 434. Additionally, the frustum shaped top surface 348 of the float body 344 includes an annular projection 436 which has a triangularly shaped cross sectional area sized to be received within a complementally shaped annular recess 438 (FIG. 25) disposed through the funnel shaped lower surface 428 and into the funnel shaped wall 422 of the funnel float cap 420. Furthermore, the alignment and interlocking means also aligns an opening 440 extending through the funnel shaped wall 422 with the circular shaped port 416 of the extraction aperture or L-shaped extraction passageway 404 such that a portion of the coiled tube 124 proximate the lower end 128 is received therethrough.

Moreover, and referring to FIGS. 30 through 33, the frustoconical or funnel shaped upper surface 424 of the funnel shaped wall 422 inwardly tapers from an upper annular outer edge 442 to a lower annular edge 444 where the funnel shaped upper surface 424 transitions into a funnel tube portion 446 of the funnel float cap 420. The funnel tube portion 446 defines a central open ended cylindrical opening 448 which extends through a central area of the cylindrically shaped neck 460 and the disked shaped base 470 of the funnel float cap 420. In turn, at least one funnel fluid passageway or aperture 450 is disposed through the funnel float cap 420 at location adjacent the funnel tube portion 446 thereby providing open communication between the funnel shaped cavity 426 (FIG. 25) and the inverted dome shaped isolation chamber 378. In one embodiment, there are four funnel fluid passageways 450 which are equally spaced apart at ninety degree intervals around funnel tube portion 446.

Figure 30:
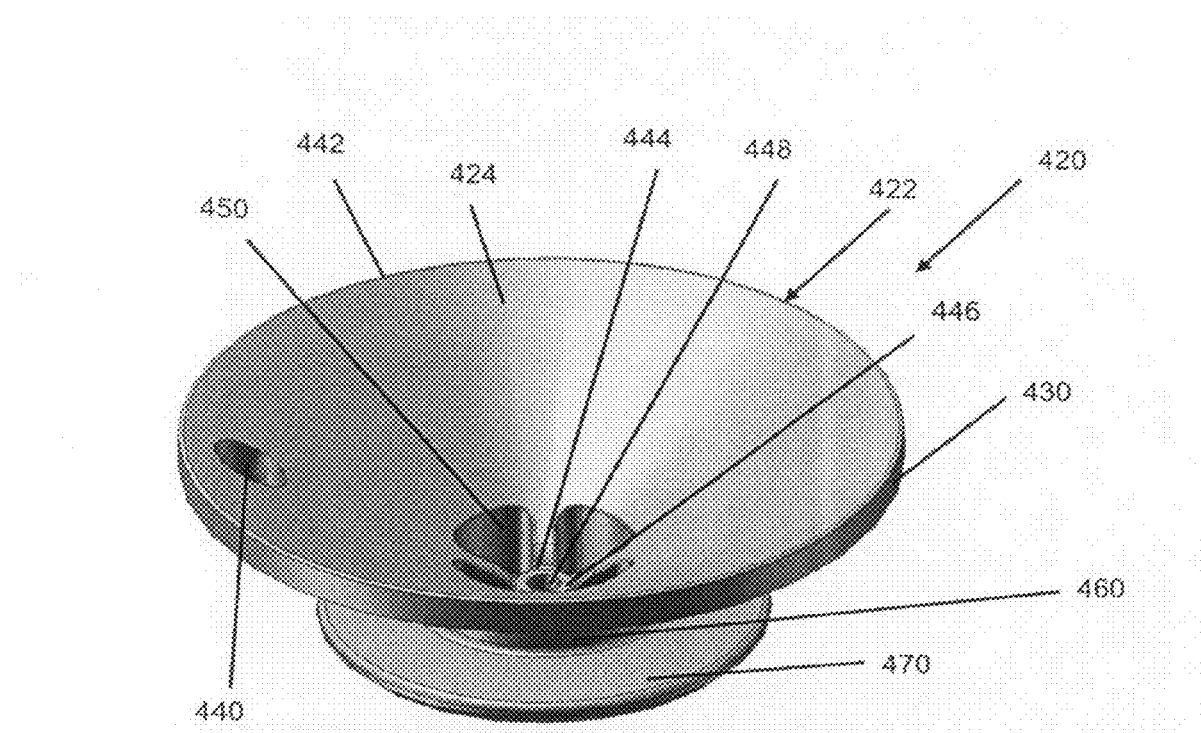
FIG. 30 is a perspective view of an embodiment of a funnel float cap of the funnel float assembly illustrated in FIG. 25.
Figure 31:
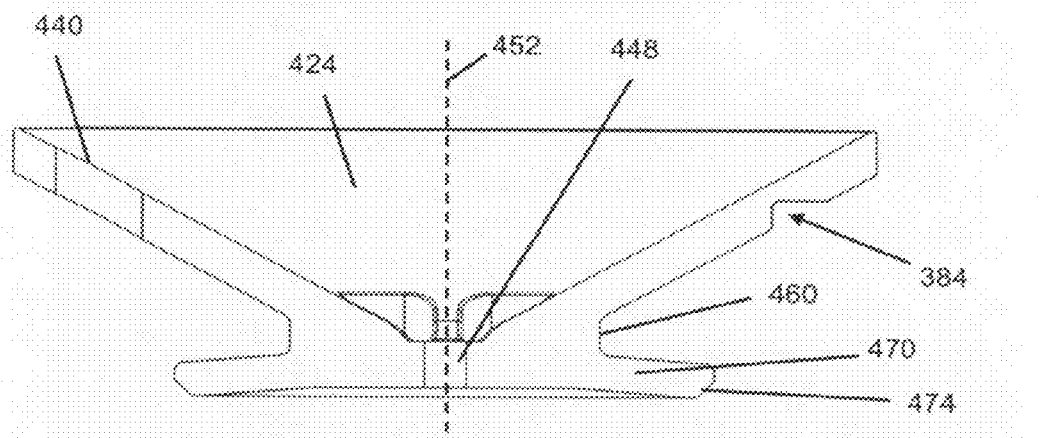
FIG. 31 is a sectional view of the funnel float cap illustrated in FIG. 30.
Figure 32:
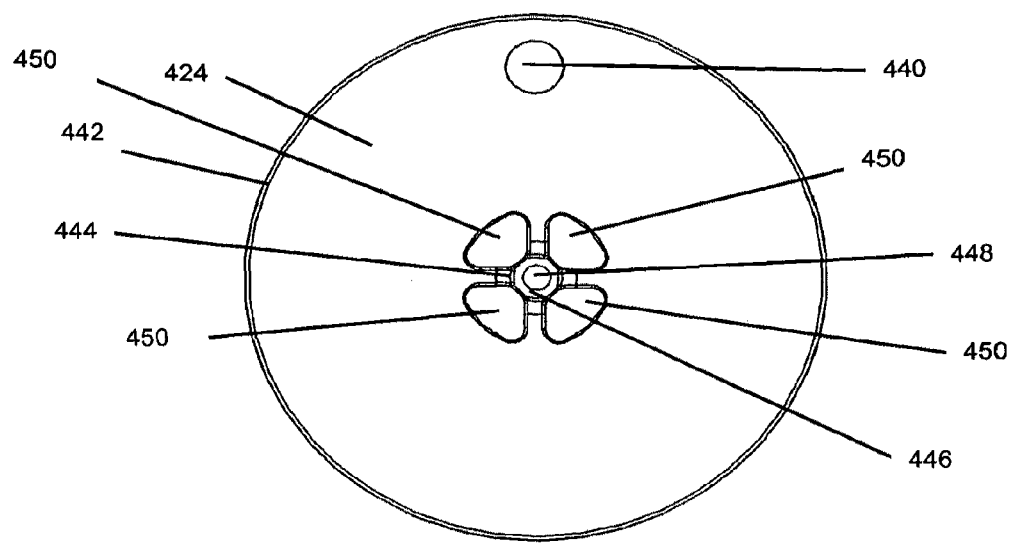
FIG. 32 is a top plan view of the funnel float cap illustrated in FIG. 30.
Figure 33:
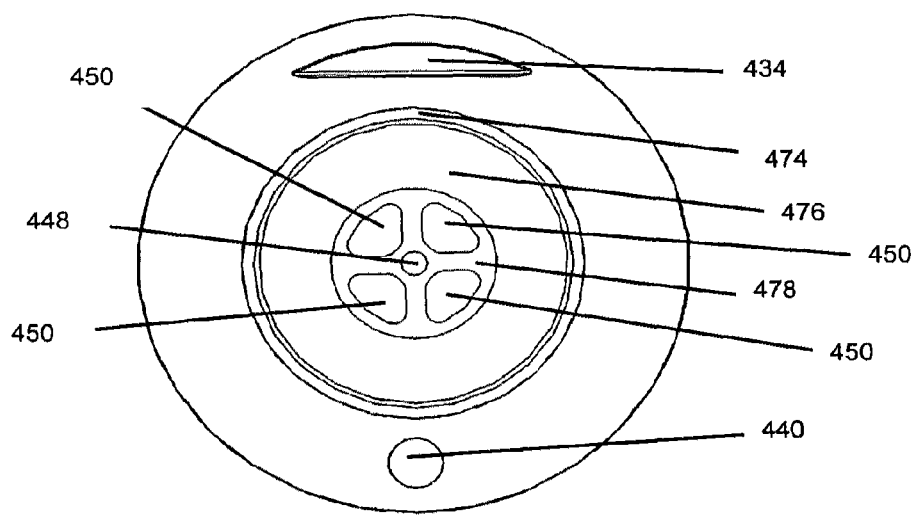
FIG. 33 is a bottom plan view of the funnel float cap illustrated in FIG. 30.

Additionally, and in one embodiment, the funnel fluid passageways or apertures 450 are generally triangular in shape with a concave apex having rounded edges located proximate the funnel tube portion 446 and a convex base having rounded edges located distal from the funnel tube portion 446 as illustrated in FIGS. 30, 32, and 33. Furthermore, and in one embodiment, the funnel shaped upper surface 210 has a declivity of about thirty degrees from a plane perpendicular to a central axis 452 (FIG. 31) of the float cap 420. Thus, this provides the funnel face with about a one hundred twenty degree opening.

Furthermore, and referring to FIGS. 31 and 33, the lower peripheral chamfer 474 transitions into an annular recessed bottom area 476 which, in turn, transitions into a substantially flat bottom surface 478 circumscribing the central open ended cylindrical opening 448 and the plurality of funnel fluid passageways or apertures 450 as illustrated in FIG. 33.

Moreover, the funnel float cap 420 is preferably constructed of, but not limited to, a material which is both biocompatible and stable for gamma irradiation. In one embodiment, the funnel float cap 420 is constructed of, but not limited to, a polystyrene or polycarbonate type of material.

Bottom Cap 480

Figure 34:
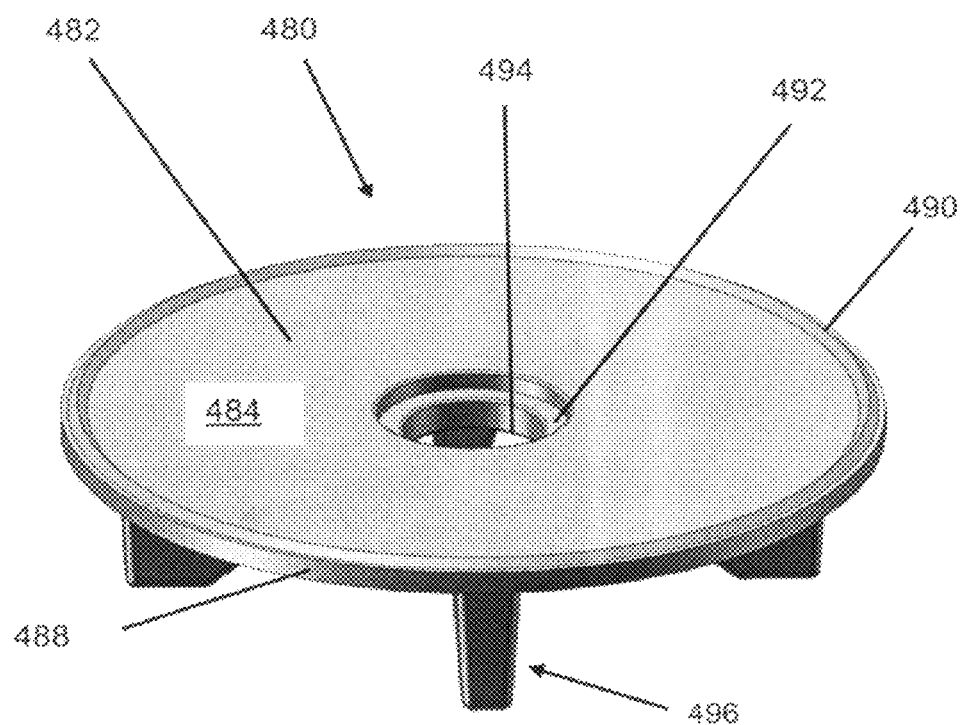
FIG. 34 is a perspective view of a bottom cap of the funnel float assembly illustrated in FIG. 25.
Figure 35:
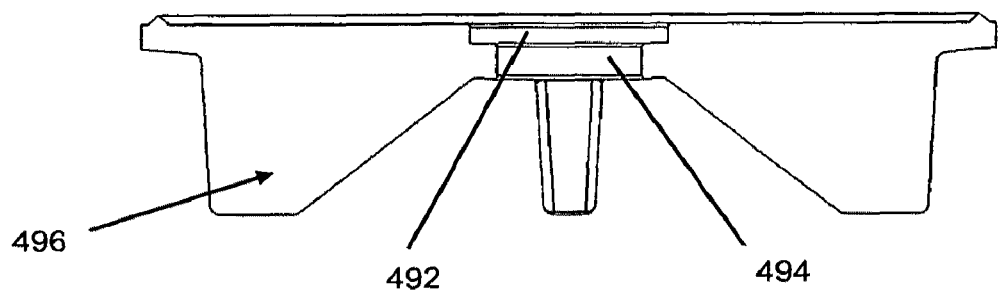
FIG. 35 is a sectional view of the bottom cap illustrated in FIG. 34.
Figure 36:
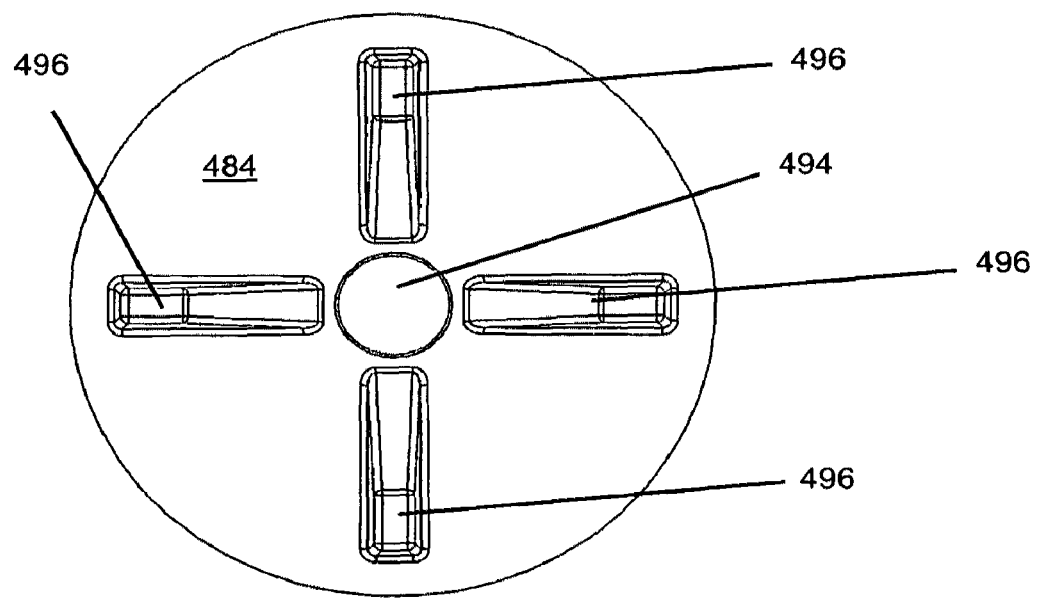
FIG. 36 is a bottom plan view of the bottom cap illustrated in FIG. 33.

Referring now to FIGS. 34 through 36, the funnel and isolation float is further comprised of the bottom float cap 480 which comprises a circular wall 482 comprised of a substantially flat top surface 484, a substantially flat bottom surface 486, and an outer peripheral edge 488 extending therebetween. Additionally, the bottom float cap 480 comprises an annular lip or projection 490 which protrudes from the substantially flat top surface 484 at a location adjacent the outer peripheral edge 488 of the circular wall 482 and which has a triangularly shaped cross sectional area sized to be received within a complementally shaped annular recess 538 (FIG. 25) disposed in the float body 344. Furthermore, the bottom float cap 480 comprises a centrally located annular ledge 492 recessed below the substantially flat top surface 484 of the circular wall 482. The centrally located annular ledge 492 circumscribes a centrally located aperture 494 disposed through the circular wall 482. Moreover, the bottom float cap 480 comprises a plurality of spaced apart fins 496 downwardly projecting from the substantially flat bottom surface of the circular wall 482. In one embodiment, there are four downwardly projecting fins 496 equally spaced apart at ninety degree intervals around the centrally located aperture 494 of the bottom float cap 480. In use and operation, the fins 496 serve to provide an initial lift off the float assembly 340 from the interior surface 330 of the closed bottom end 314 of the tube 312 for precluding a vacuum seal from forming therebetween while also protecting the elastic duckbill valve 248 under initial conditions.

Bottom float cap 480 is preferably constructed of, but not limited to, a material which is both biocompatible and stable for gamma irradiation. In one embodiment, the bottom float cap 480 is constructed of, but not limited to, a polystyrene or polycarbonate type of material.

Bottom Cap 500

Figure 37:
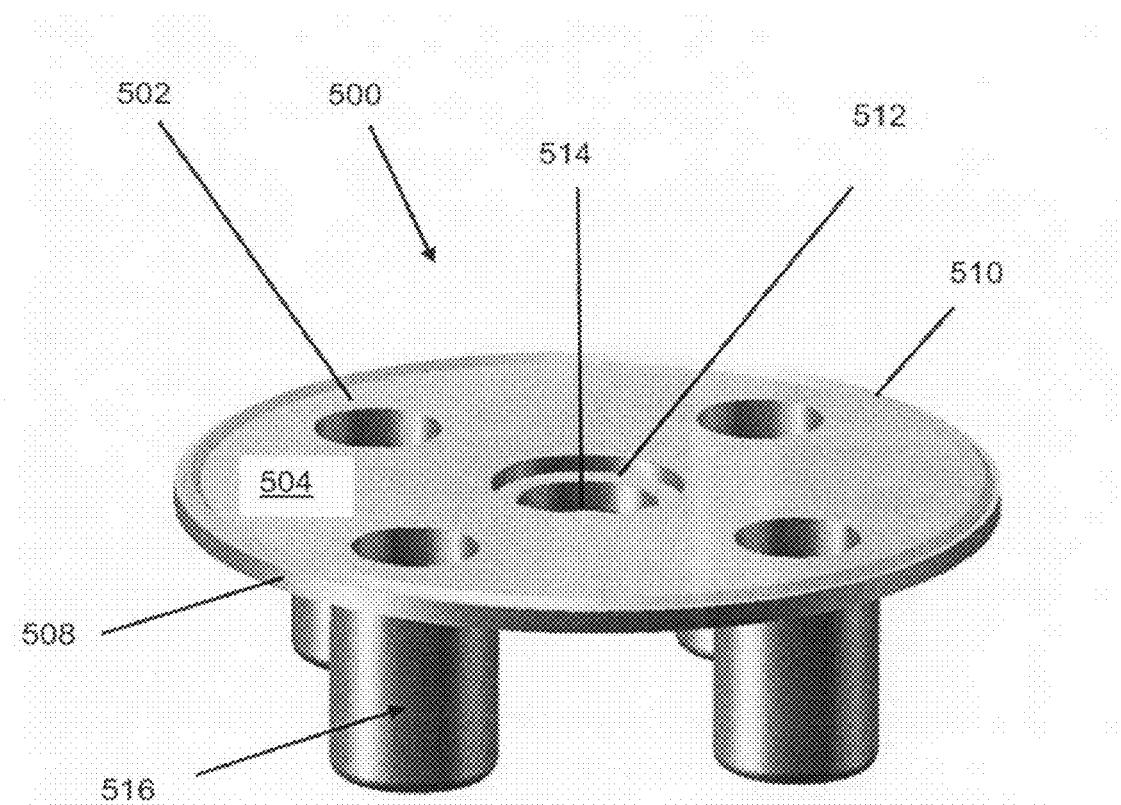
FIG. 37 is a perspective view of another embodiment of a bottom cap for the funnel float assembly illustrated in FIG. 25.
Figure 38:
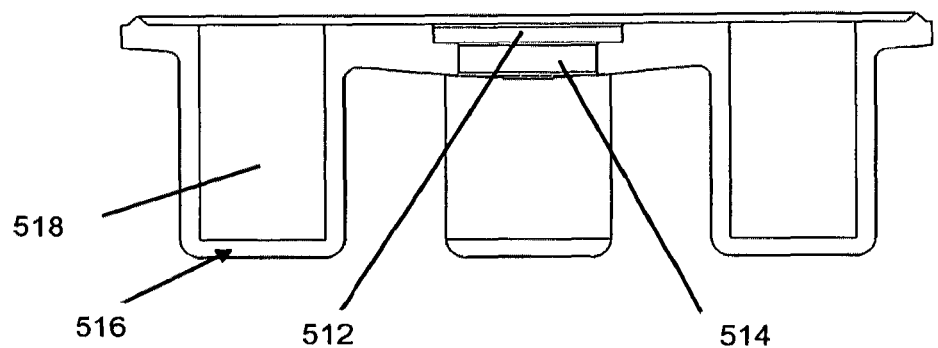
FIG. 38 is a sectional view of the bottom cap illustrated in FIG. 37.
Figure 39:
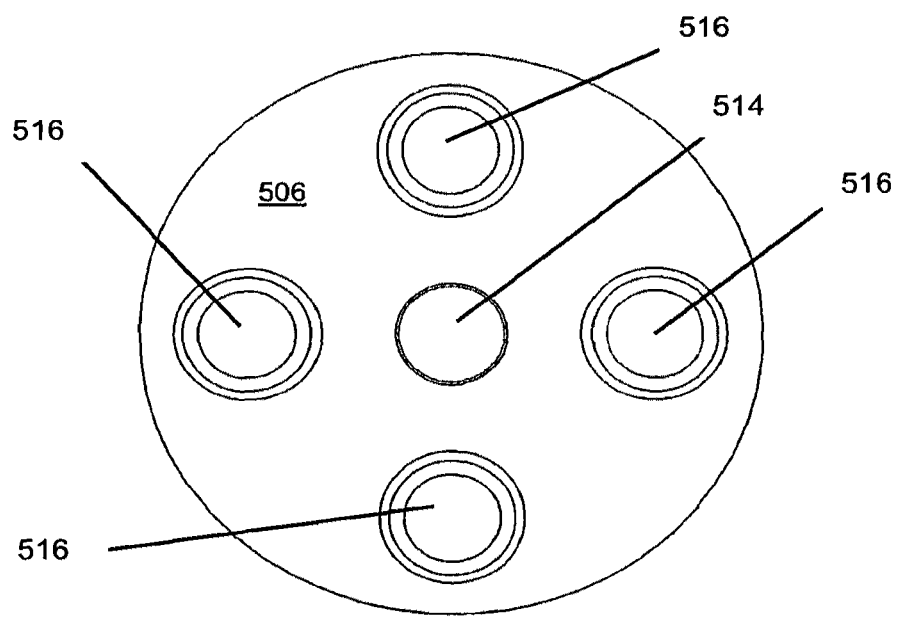
FIG. 39 is a bottom plan view of the bottom cap illustrated in FIG. 37.

Referring to FIGS. 37 through 39, and in another embodiment, the funnel and isolation float 342 is further comprised of the bottom float cap 500 which comprises a circular wall 502 comprised of a substantially flat top surface 504, a substantially flat bottom surface 506, and an outer peripheral edge 508 extending therebetween. Additionally, the bottom float cap 500 comprises an annular lip or projection 510 which protrudes from the substantially flat top surface 504 at a location adjacent the outer peripheral edge 508 of the circular wall 502 and which has a triangularly shaped cross sectional area sized to be received within a complementally shaped annular recess 538 (FIG. 25) disposed in the float body 344. Furthermore, the bottom float cap 500 comprises a centrally located annular ledge 512 recessed below the substantially flat top surface 504 of the circular wall 502. The centrally located annular ledge 512 circumscribes a centrally located aperture 514 disposed through the circular wall 502. Moreover, the bottom float cap 500 comprises a plurality of spaced apart cylindrically shaped legs 516 downwardly projecting from the substantially flat bottom surface 506 of the circular wall 502. In one embodiment, there are four downwardly projecting cylindrically shaped legs 516 equally spaced apart at ninety degree intervals around the centrally located aperture 514 of the bottom float cap 500. Each cylindrically shaped leg 516 includes a blind bore 518 downwardly extending from an open end disposed in the substantially flat top surface 504 of the circular wall 502. In use and operation, the cylindrically shaped legs 516 serve to provide an initial lift off the float assembly 340 from the interior surface 330 of the closed bottom end 314 of the tube 312 for precluding a vacuum seal from forming therebetween while also protecting the elastic duckbill valve 248 under initial conditions. Bottom float cap 500 is preferably constructed of, but not limited to, a material which is both biocompatible and stable for gamma irradiation. In one embodiment, the bottom float cap 500 is constructed of, but not limited to, a polystyrene or polycarbonate type of material.

Figure 40:
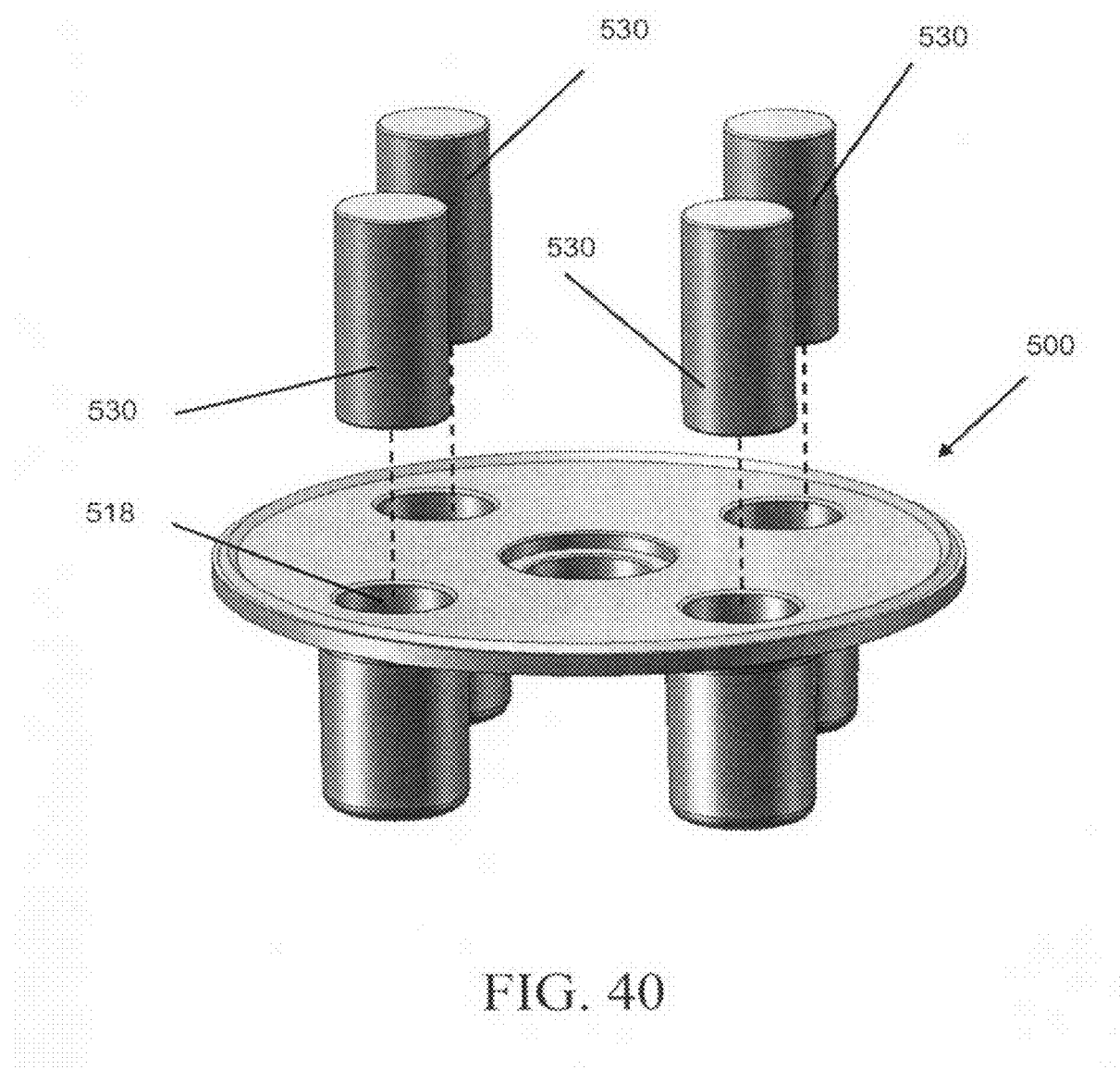
FIG. 40 is an exploded parts perspective view of a plurality of density tuning weights and the bottom cap illustrated in FIG. 37.
Figure 41:
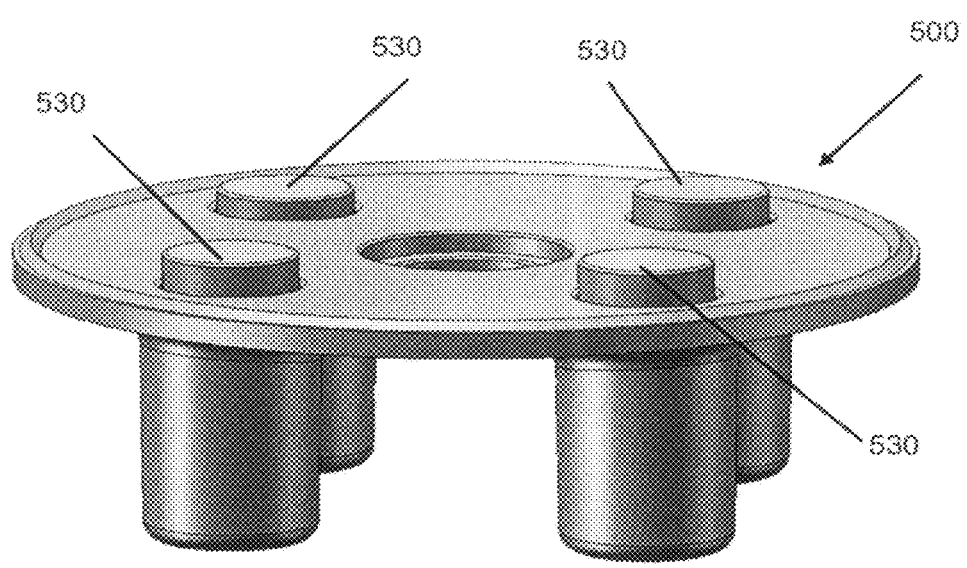
FIG. 41 is a perspective view of the coupling of the plurality of density tuning weights with the bottom cap illustrated in FIG. 37.

In addition, and referring to FIGS. 40 and 41, each empty blind bore 518 can serve as a carrier site for a cylindrically shaped weight 530 that is inserted therein for the purpose of controlling the overall density of the float assembly 340. Thus, one or more the weights 530 can be coupled with the bottom float cap 500 to provide ballast for the purpose of controlling the overall density of the float assembly 340. The preferred materials for the ballast or weights to adjust the specific gravity of the float assembly 340 are metal rods such as stainless steel. For applications of the invention to blood and bone marrow processing to harvest buffy coat, it is desirable to have the float assembly 340 be tuned between the density of plasma and packed red cells and specifically a preferred float assembly density is in the range of 1.02 to 1.08 grams/cubic centimeter and most preferentially in the range of 1.03 to 1.07 grams/cubic centimeter. The specific density used can be optimized for the intended therapeutic or diagnostic use in regard to the cell composition for the device to be produced. The heavier weight will cause an increase in red cell content and increased white blood cell (WBC) recovery.

Figure 42:
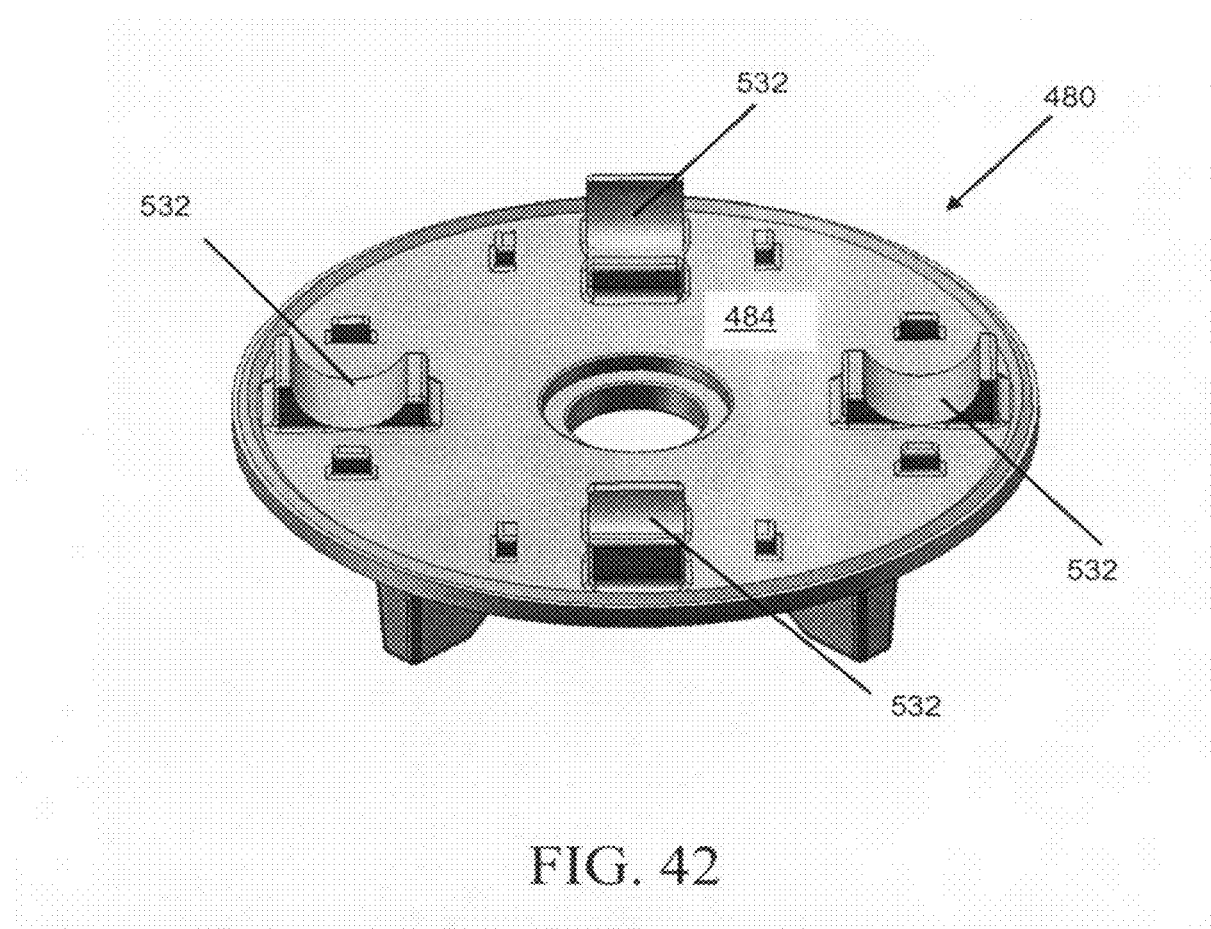
FIG. 42 is a perspective view of the bottom cap illustrated in FIG. 34 with a plurality of weight cradles added thereto.
Figure 43:
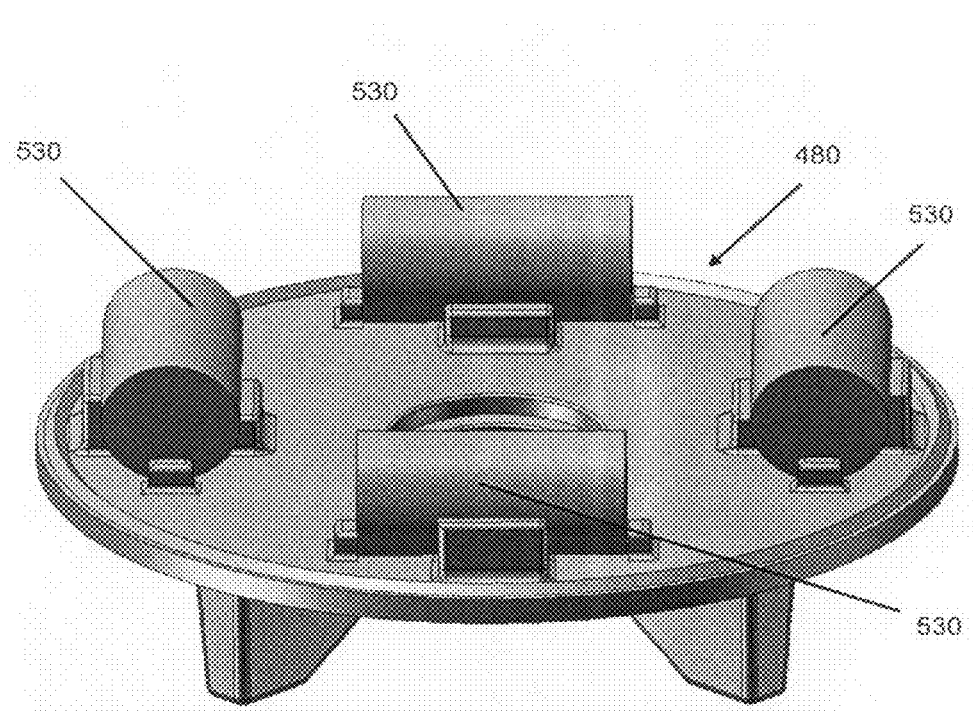
FIG. 43 is a perspective view of the coupling of the plurality of density tuning weights with the bottom cap illustrated in FIG. 42.

Referring to FIGS. 42 and 43, each cylindrically shaped weight 530 can also be carried by each cradle structure 532 formed on the flat top surface 484 of the bottom float cap 480 and received within one of the four spaced apart cavities 394, 396, 398, and 400 in the bottom surface 386 of the float body 344 (FIG. 28) when the bottom float cap 480 is mated with the float body 344. Thus, one or more weights 530 can be coupled to the bottom float cap 480 to provide ballast for the purpose of controlling the overall density of the float assembly 340 as delineated above.

Figure 44:
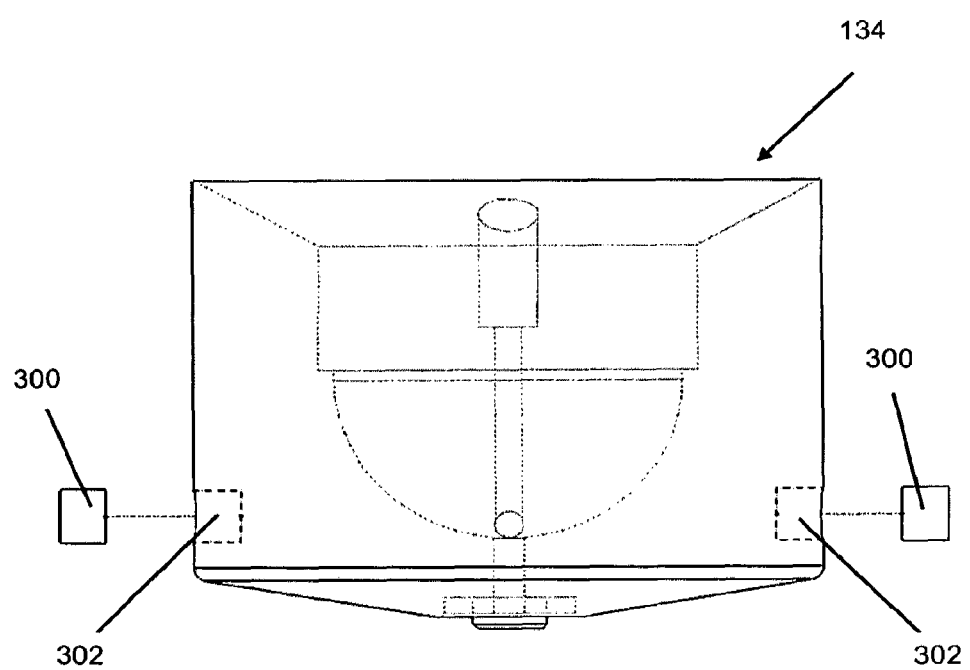
FIG. 44 is an exploded parts perspective view of a plurality of density tuning weights and the float body of the funnel float assembly illustrated in FIG. 6.
Figure 1:
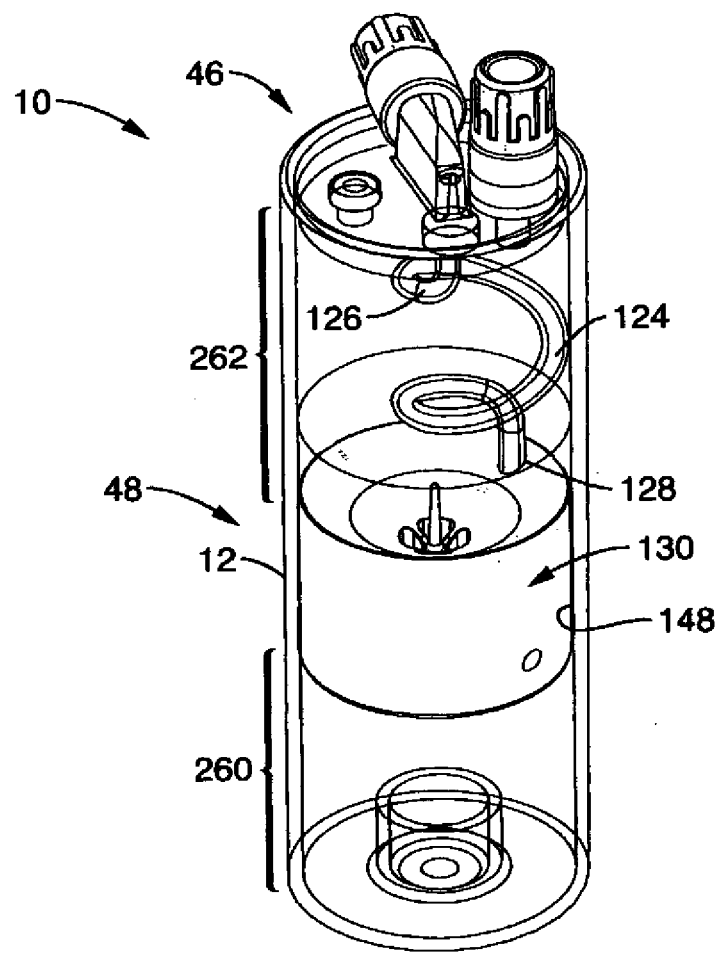
Figure 2:
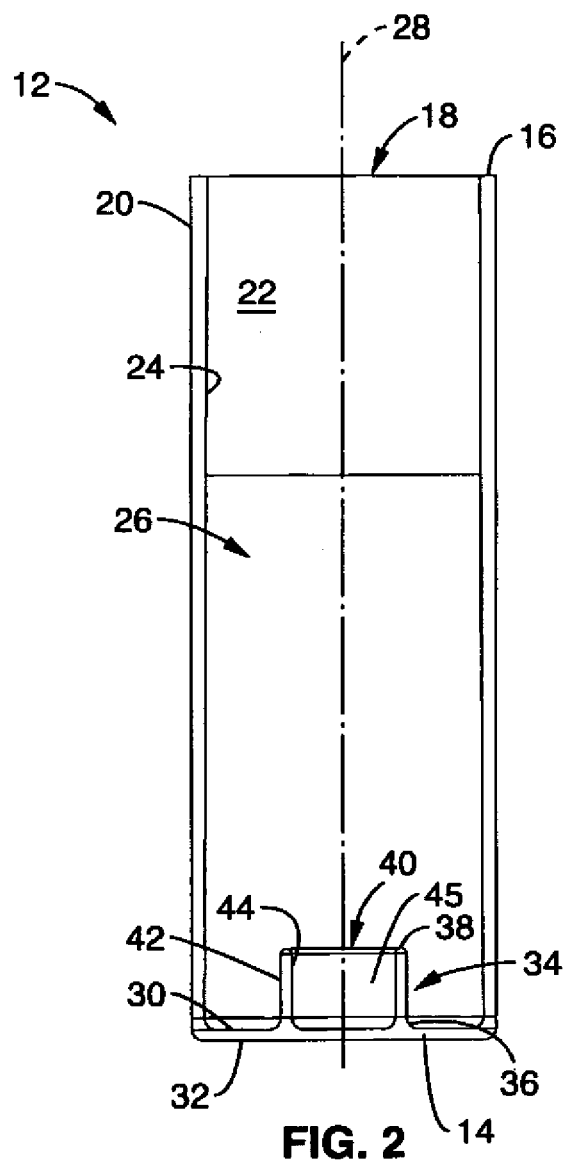
Figure 3:
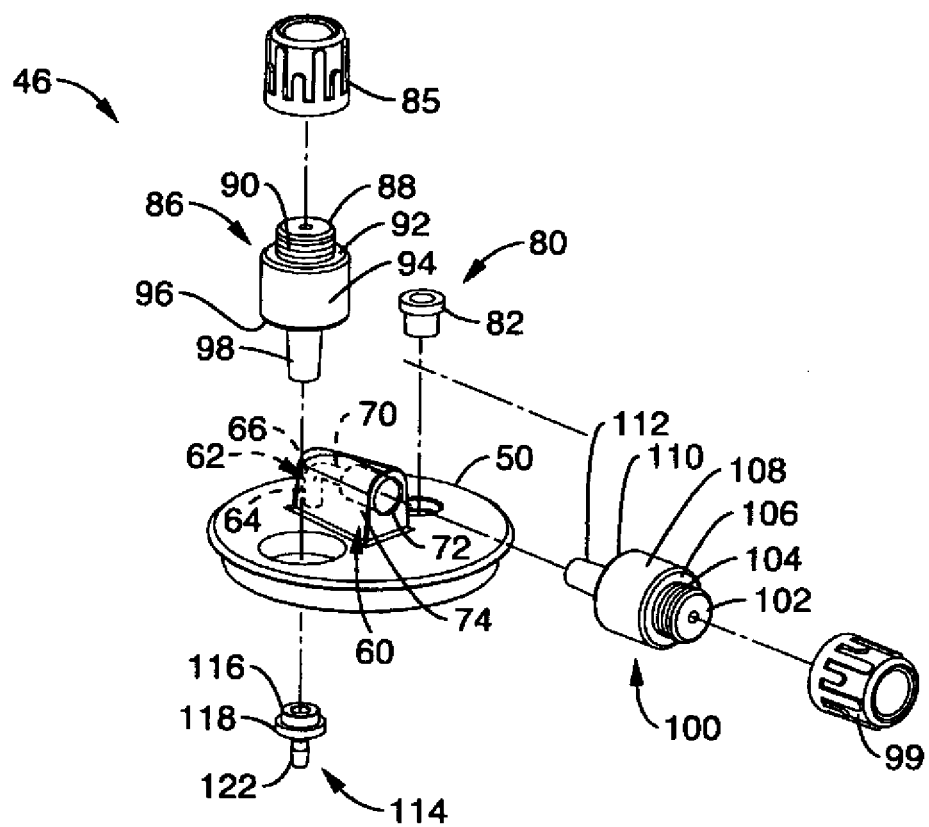
Figure 4:
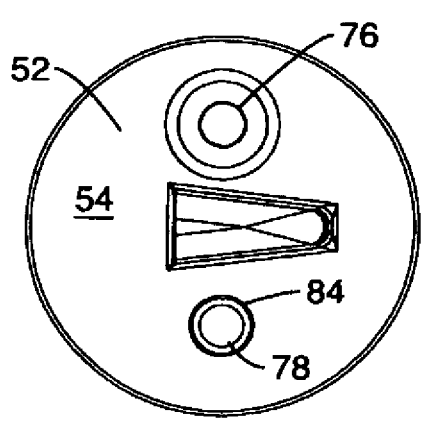
Figure 5:
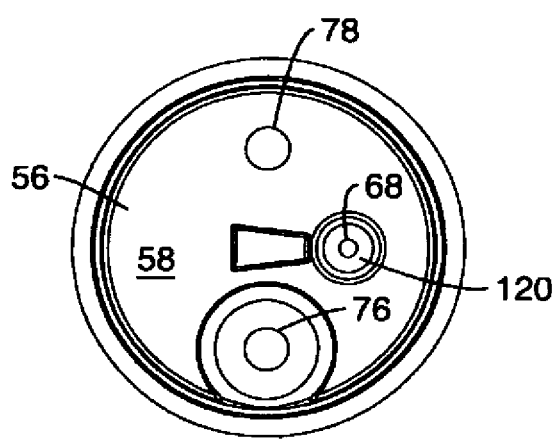
Figure 6:
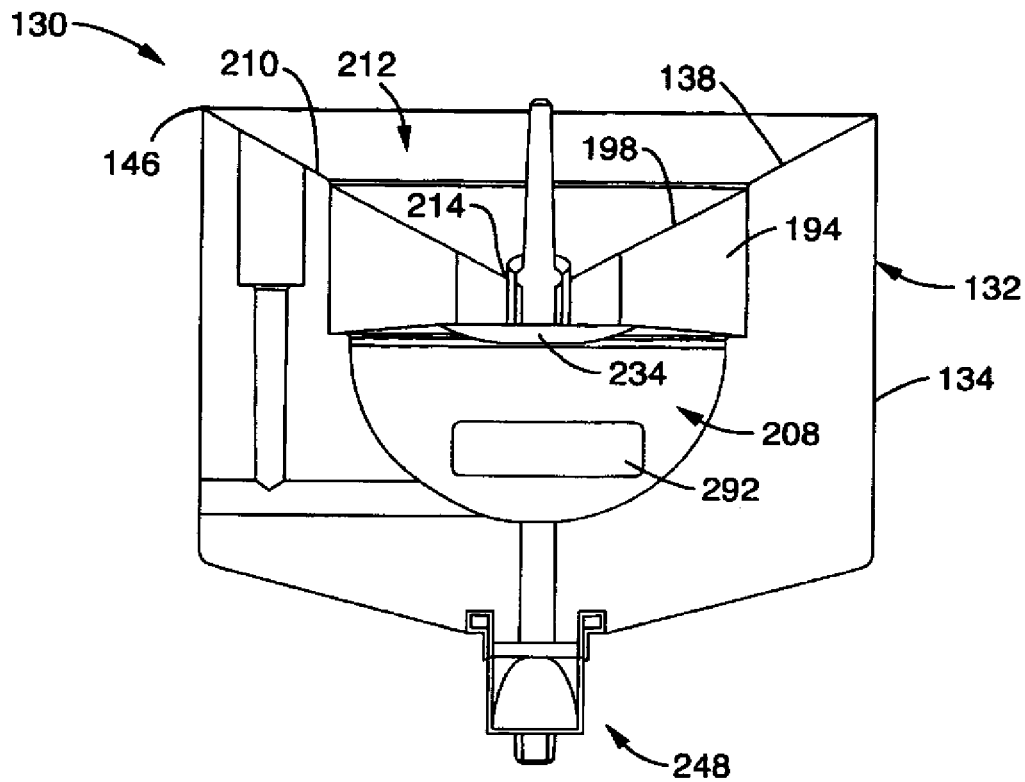
Figure 7:
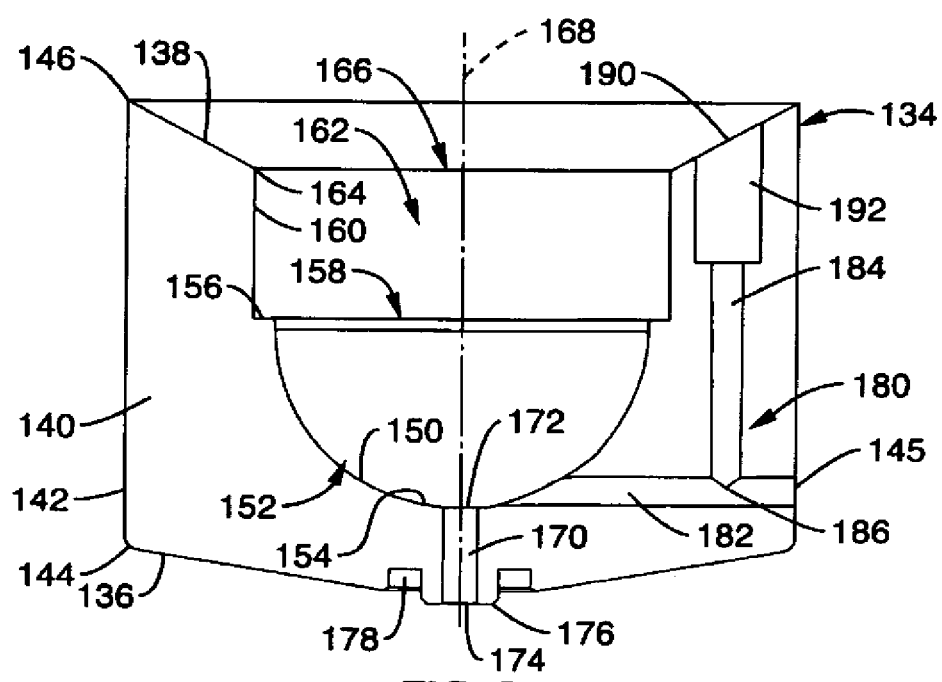
Figure 8:
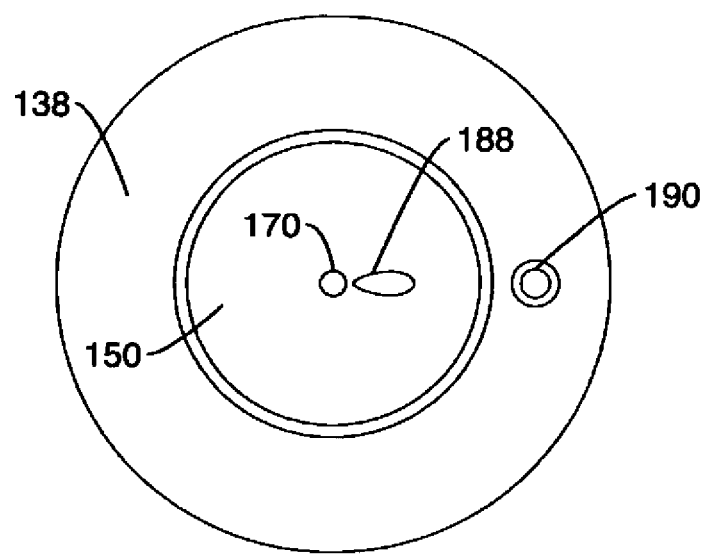
Figure 9:
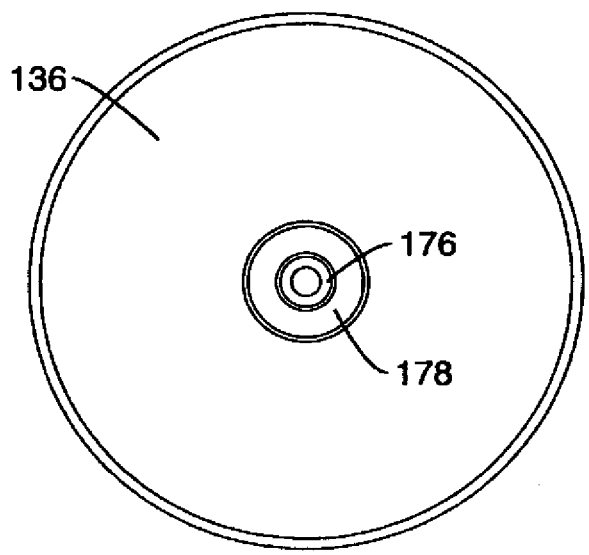
Figure 10:
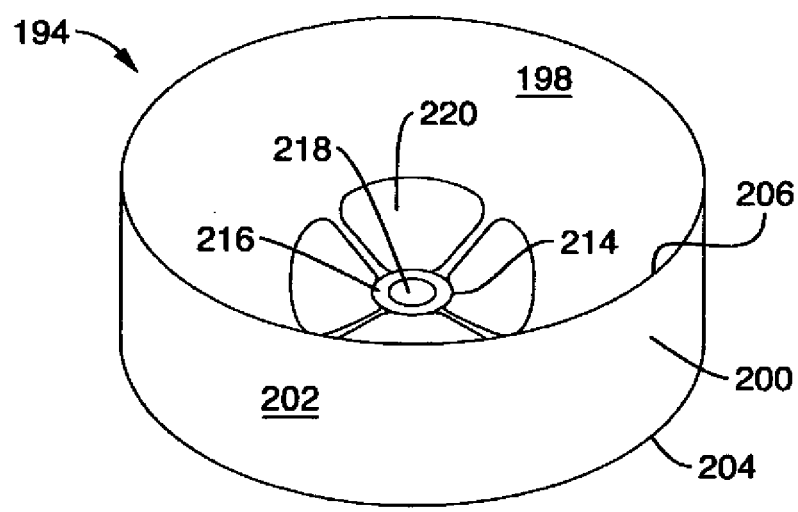
Figure 11:
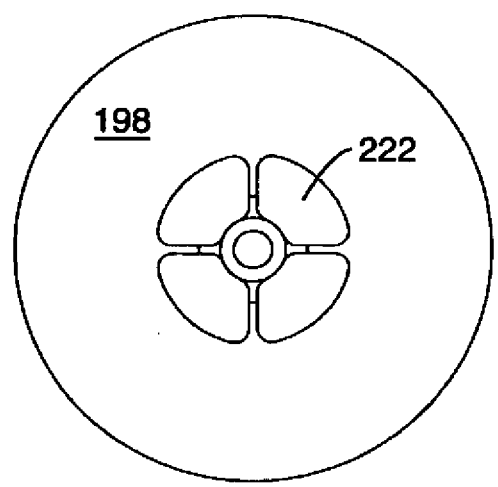
Figure 12:
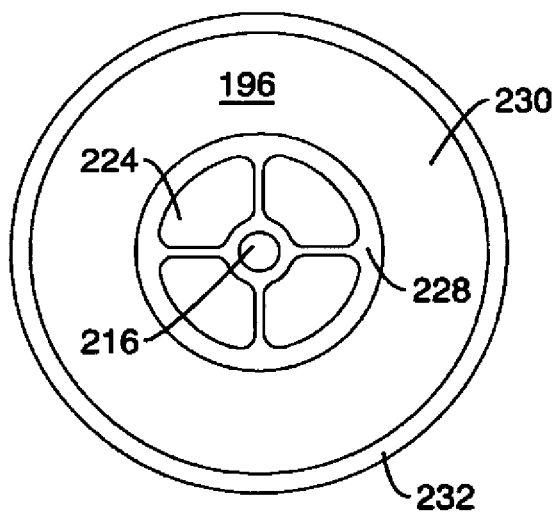
Figure 14:
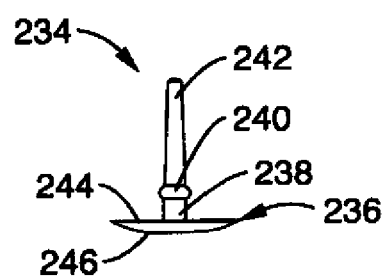
Figure 13:
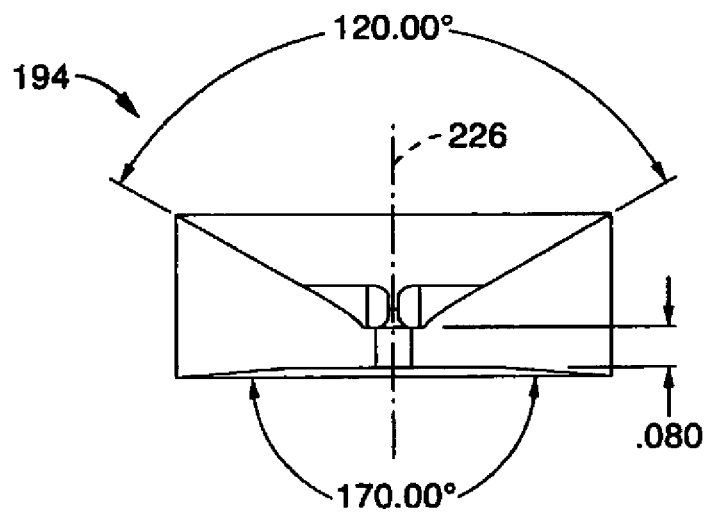
Figure 15:
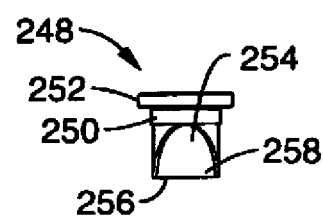
Figure 16:
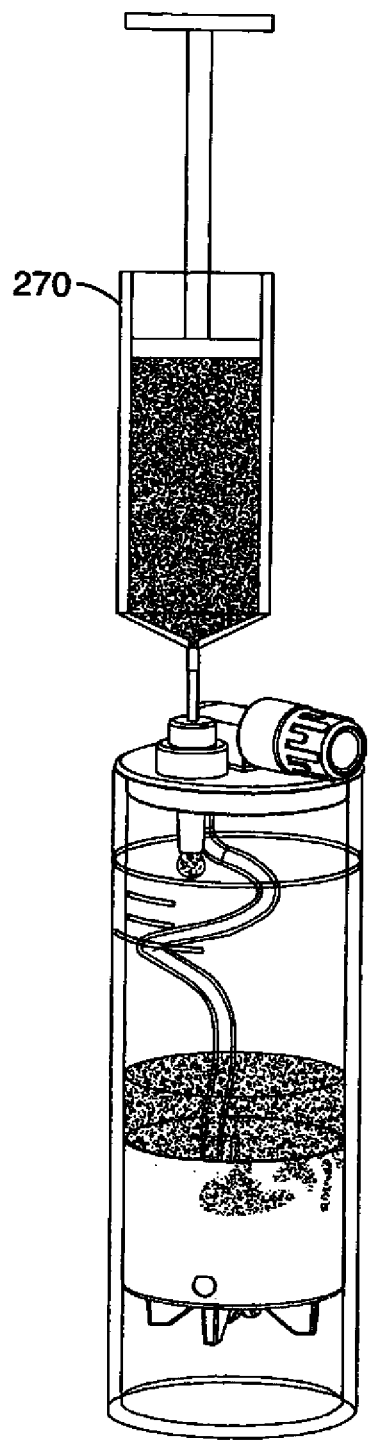
Figure 17:
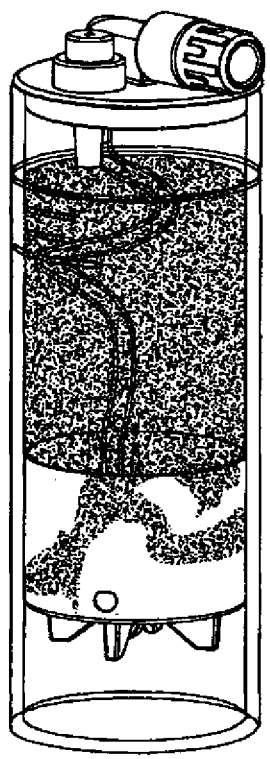
Figure 18:
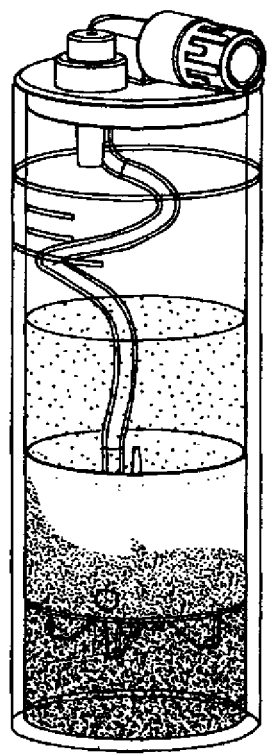
Figure 19:
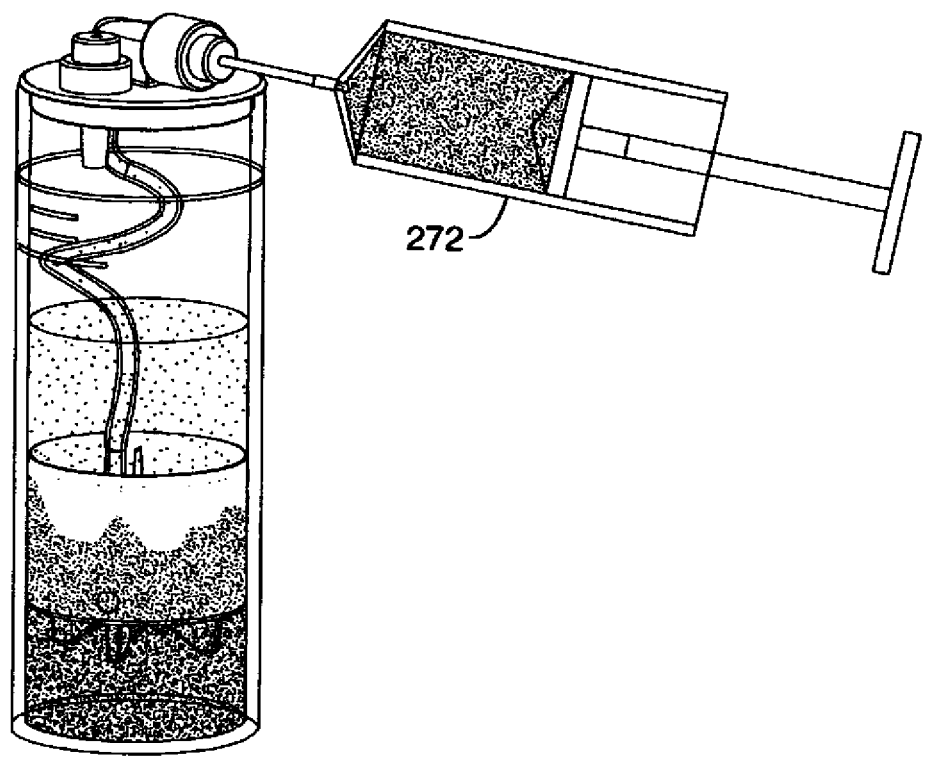
Figure 20:
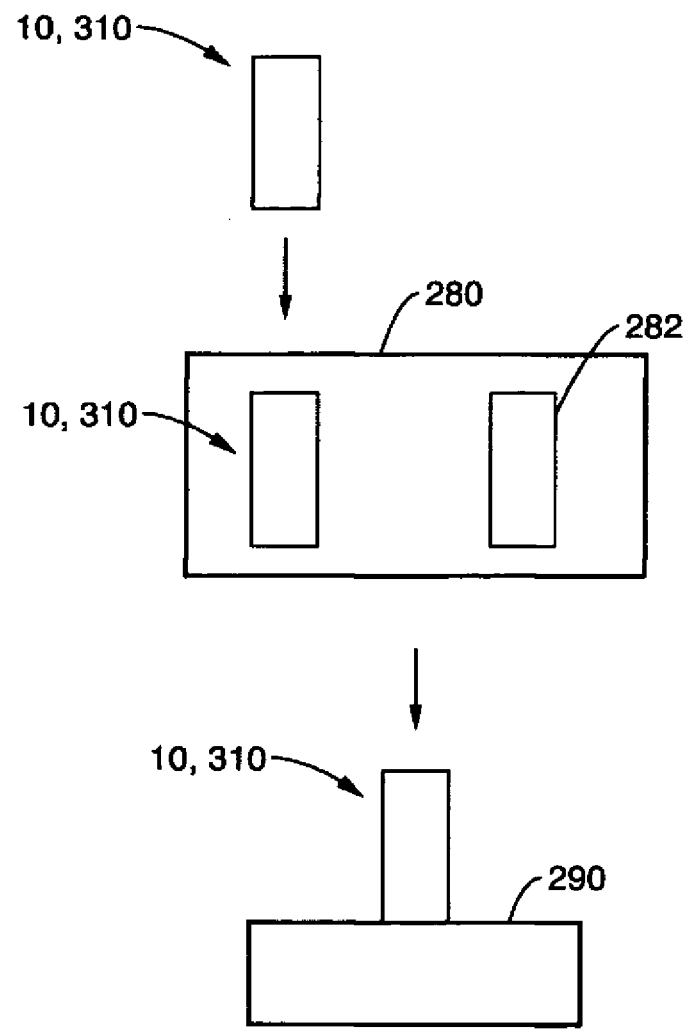
Figure 21:
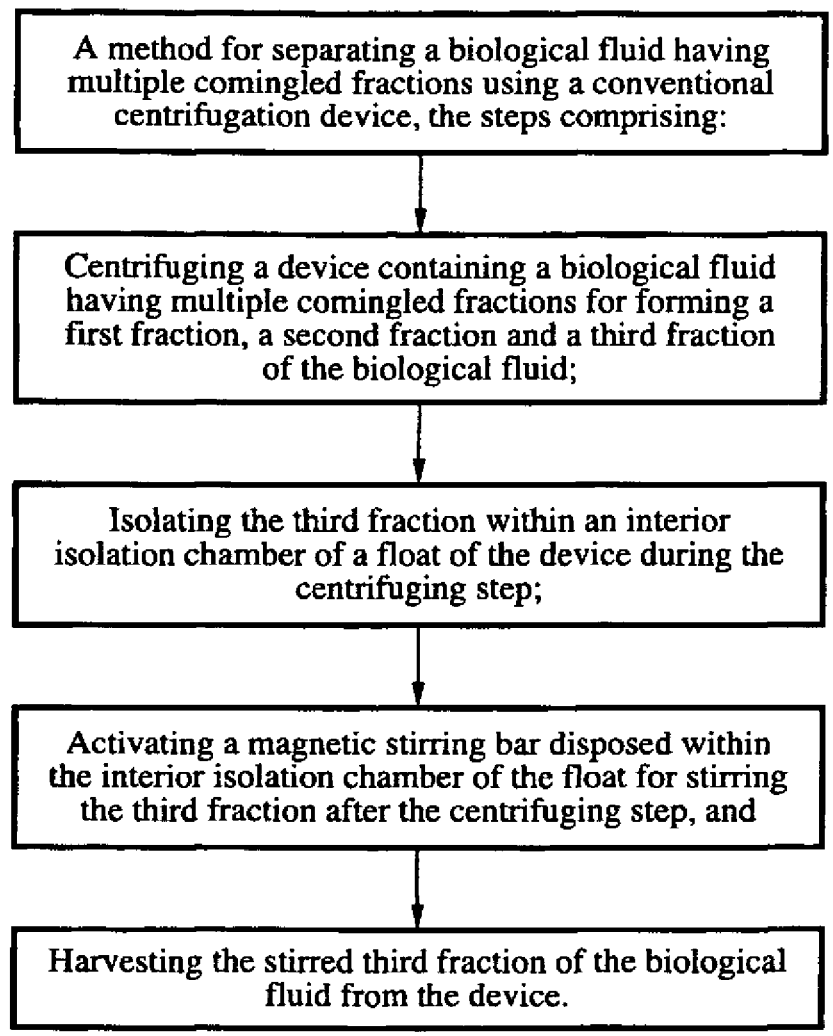
FIG. 21 is a block diagram of an embodiment of a method for utilizing the device.
Figure 22:
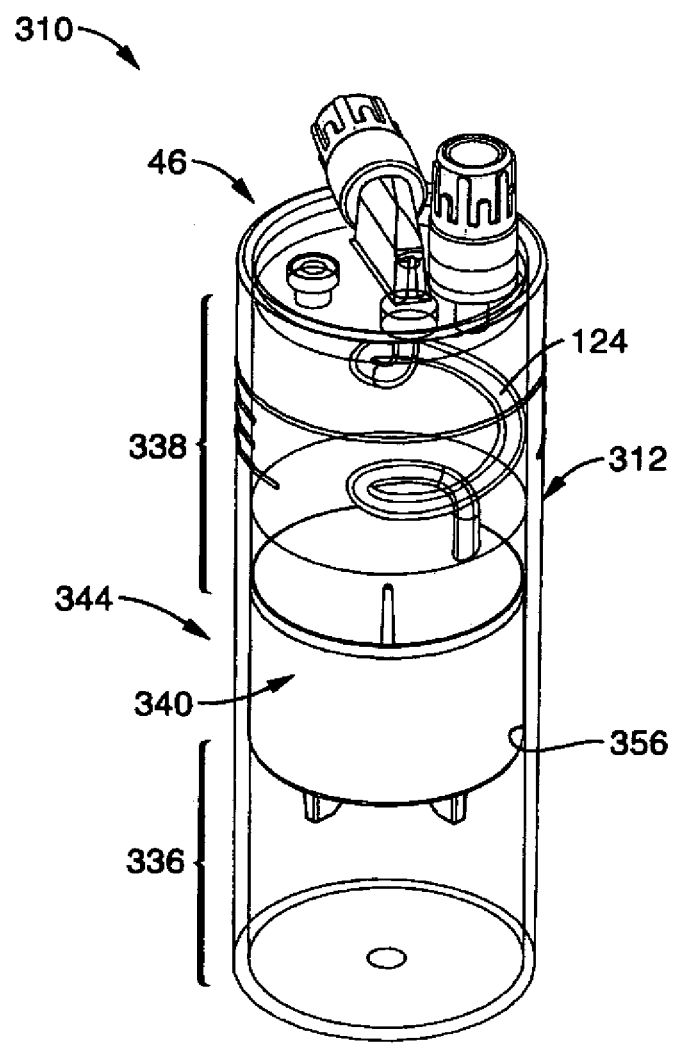
Figure 23:
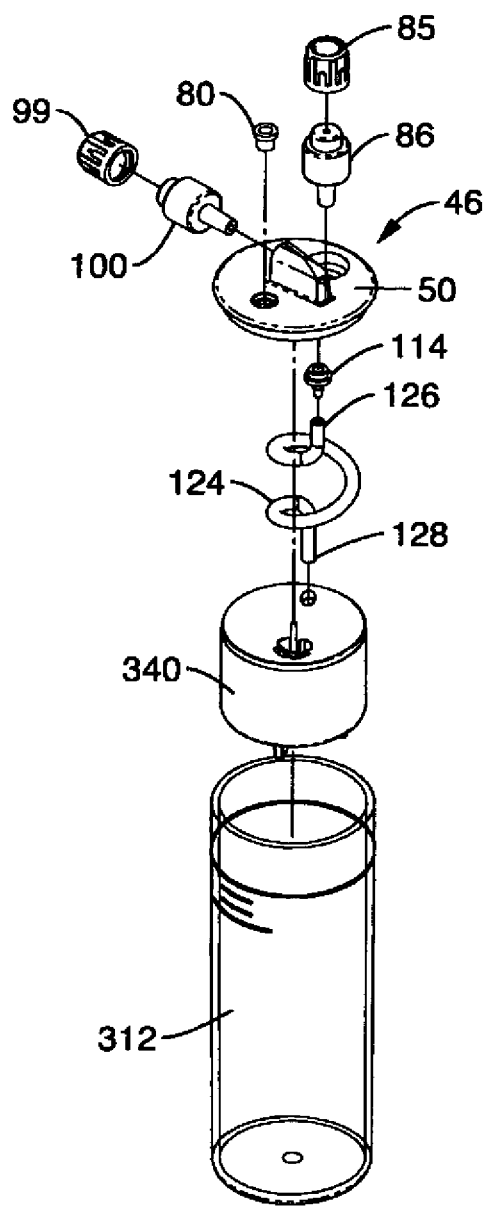
Figure 24:
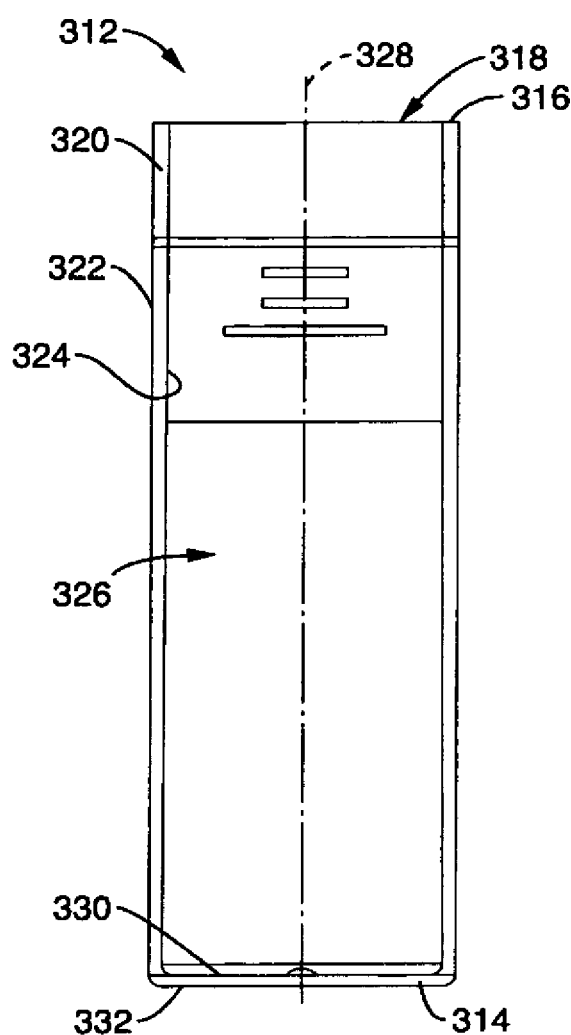
Figure 25:
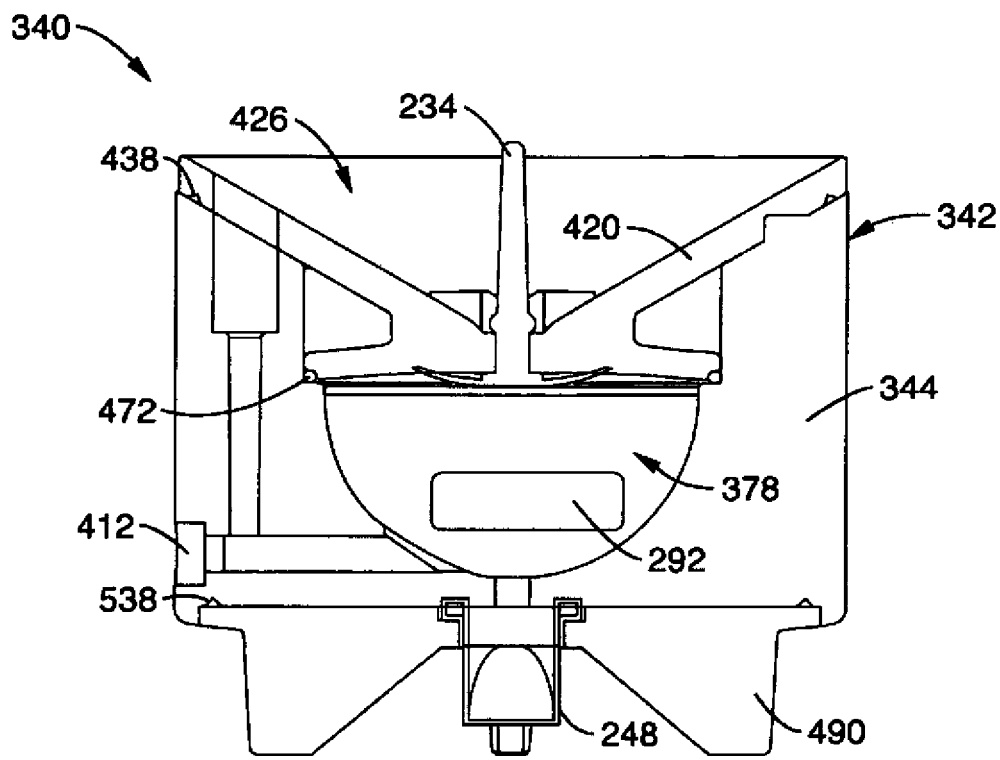
Figure 26:
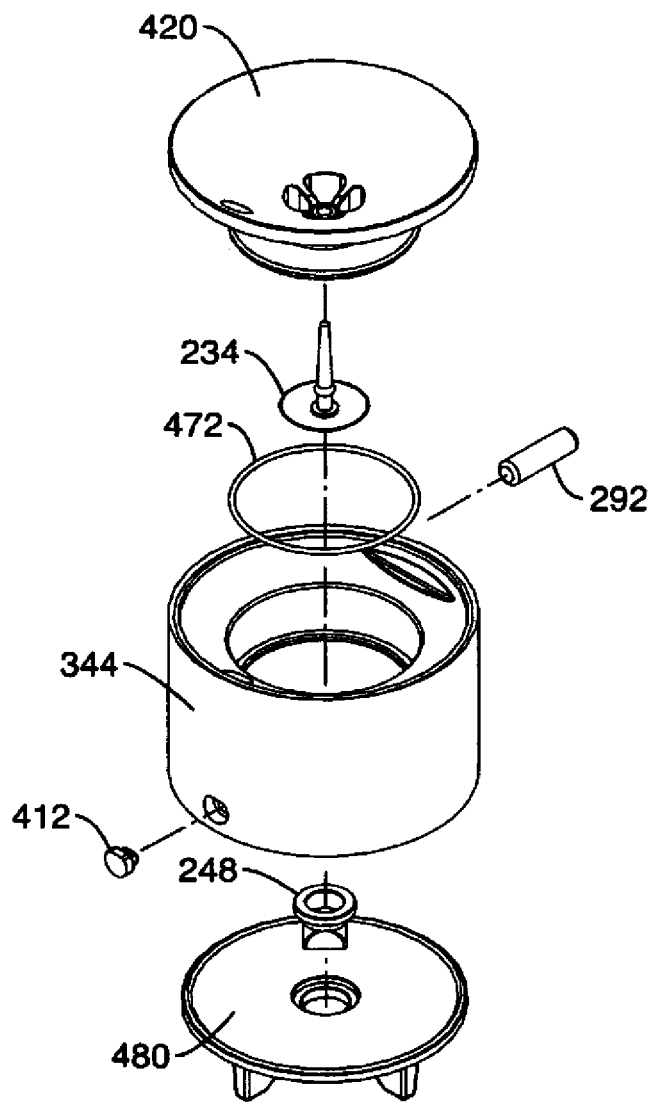
Figure 27:
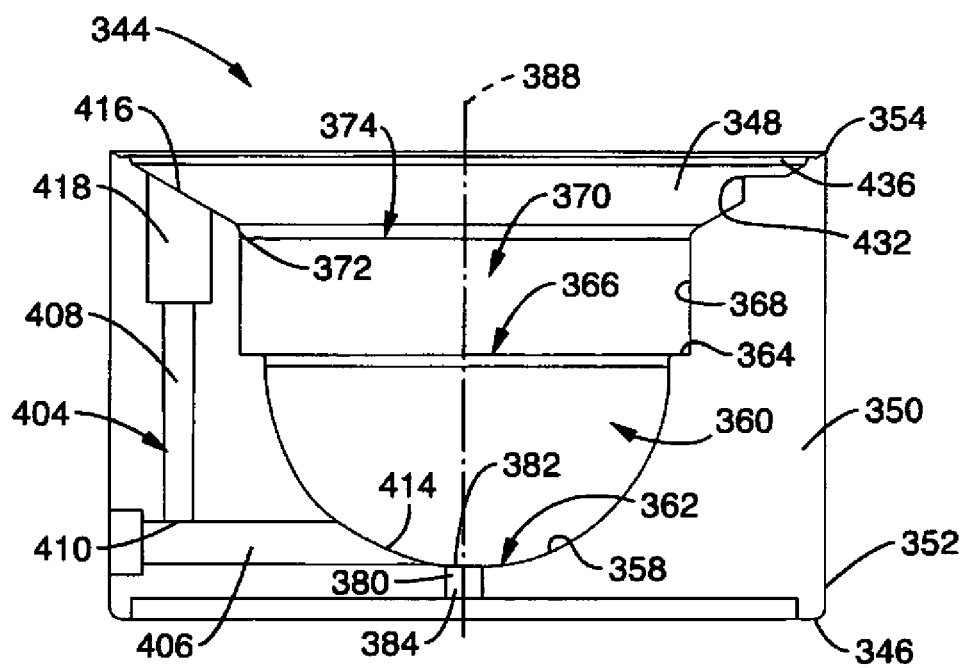
Figure 28:
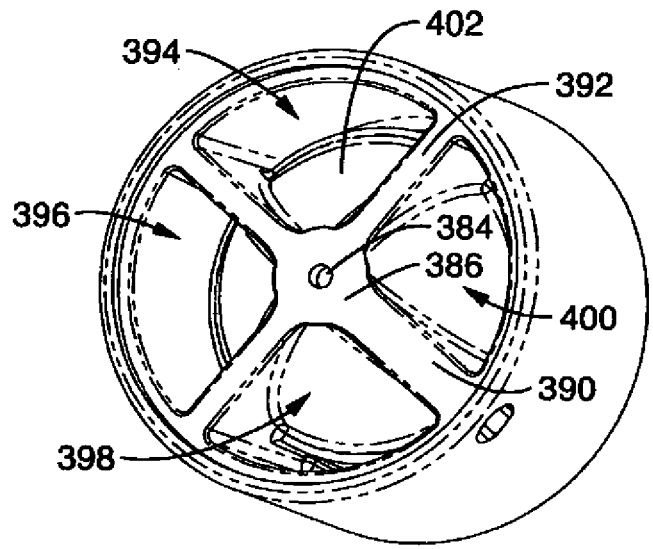
Figure 29:
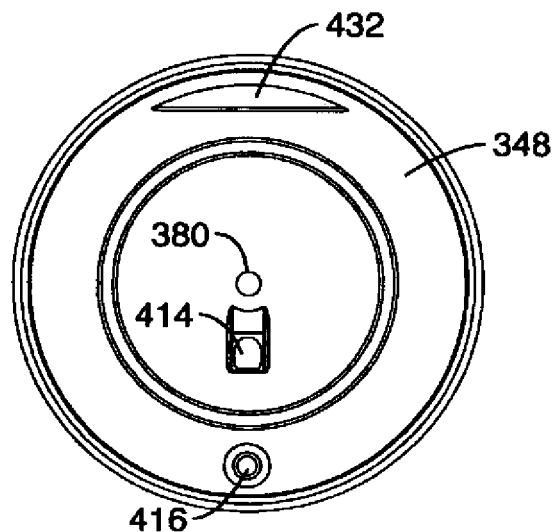
Figure 30:
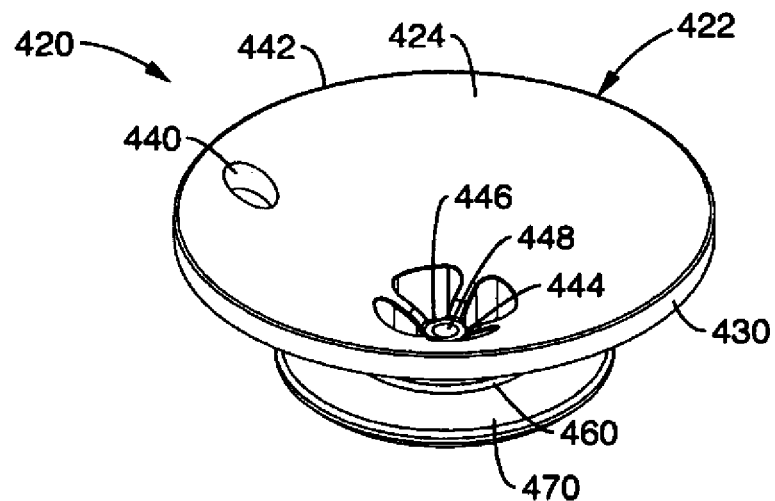
Figure 31:
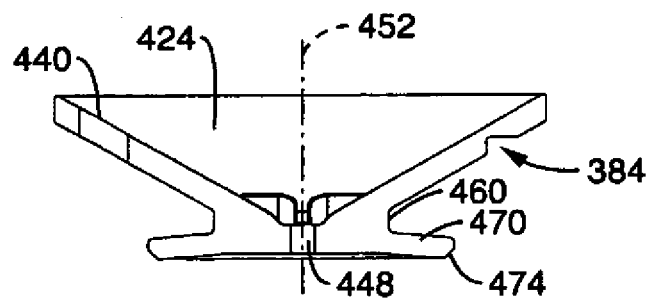
Figure 32:
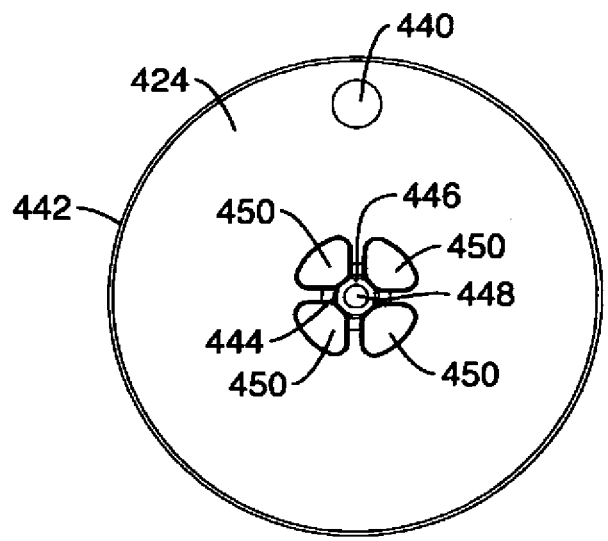
Figure 33:
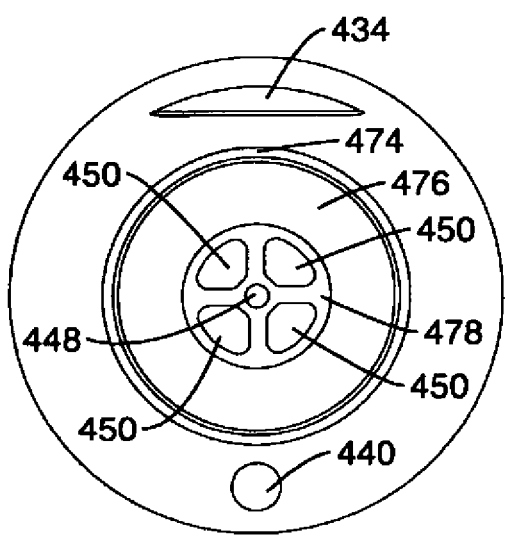
Figure 34:
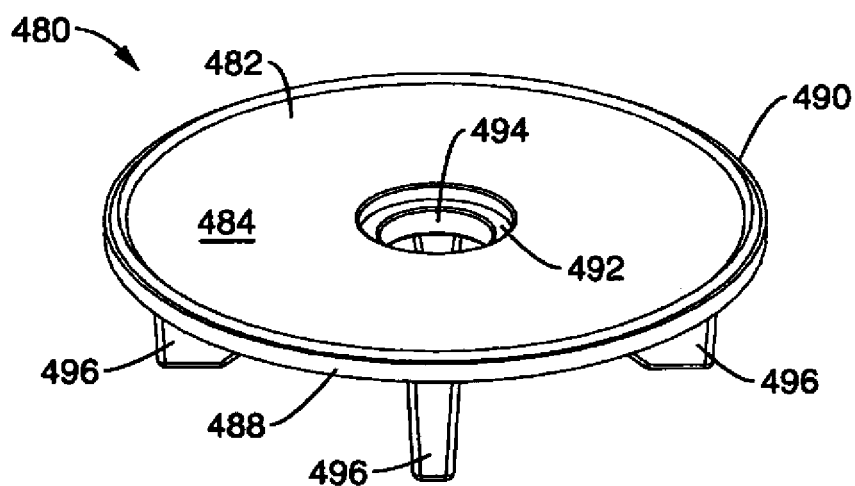
Figure 35:
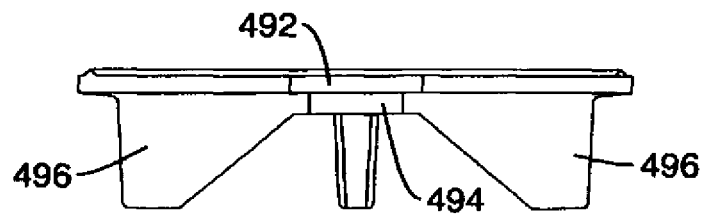
Figure 36:
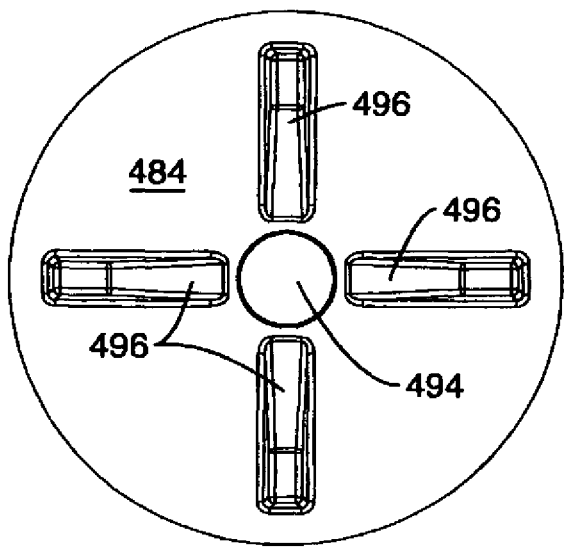
Figure 37:
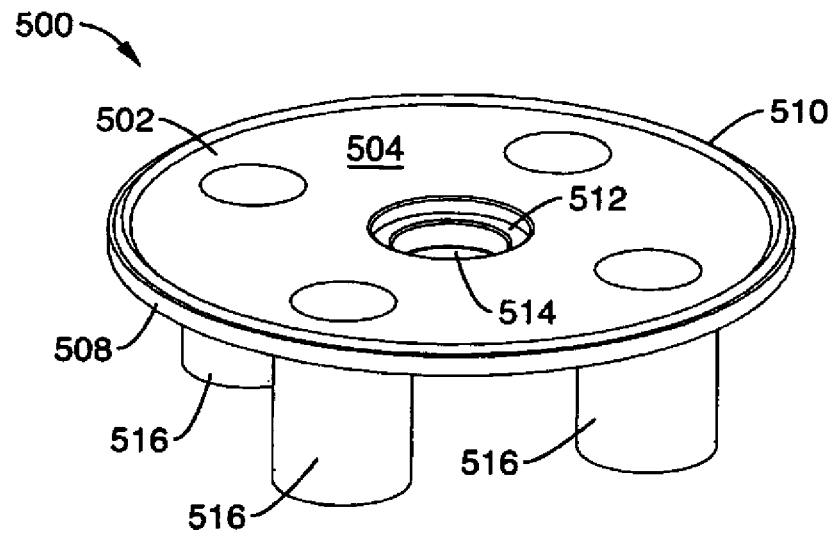
Figure 38:
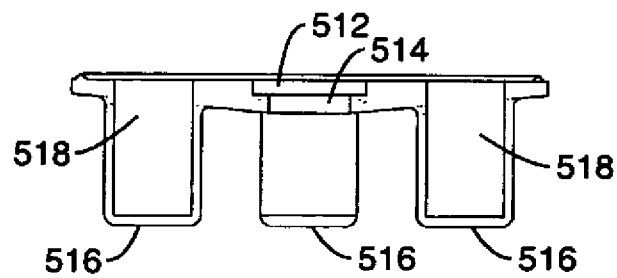
Figure 39:
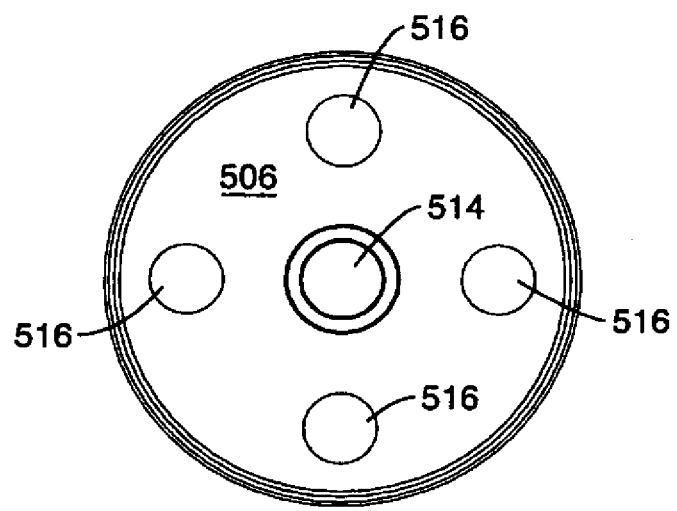
Figure 40:
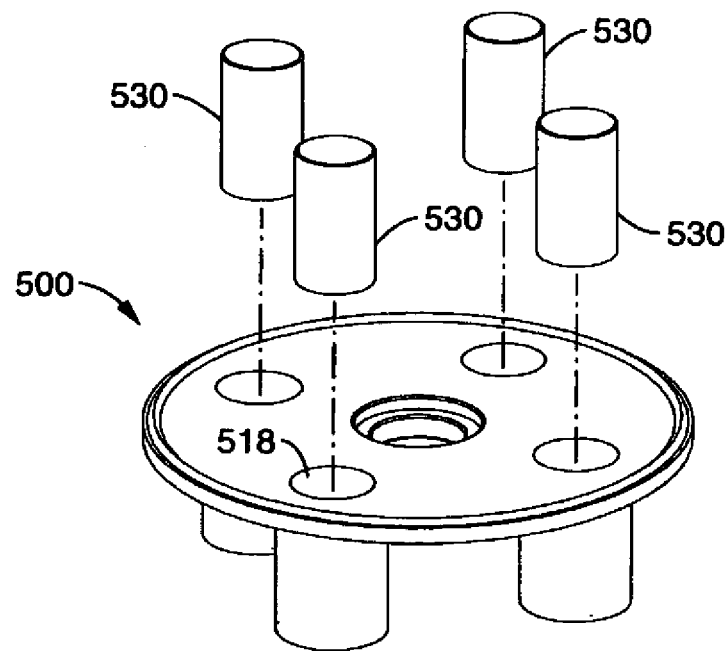
Figure 41:
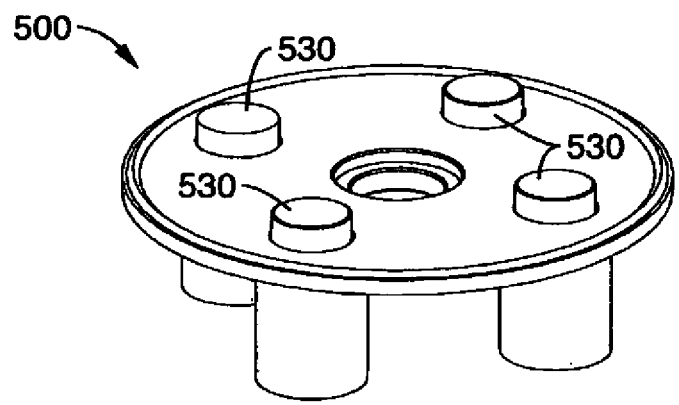
Figure 42:
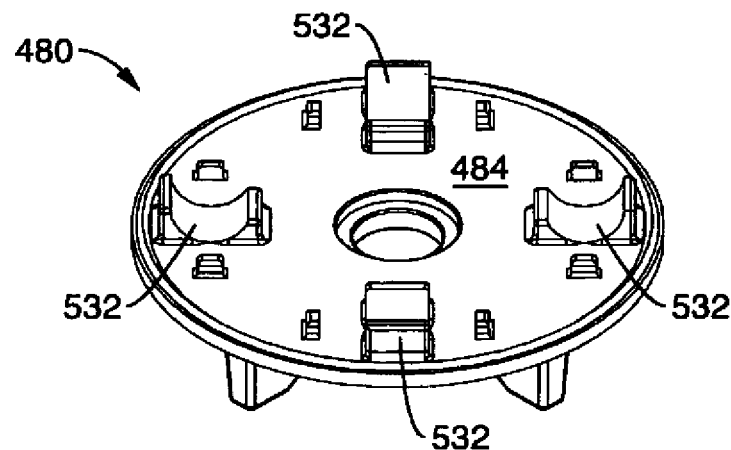
Figure 43:
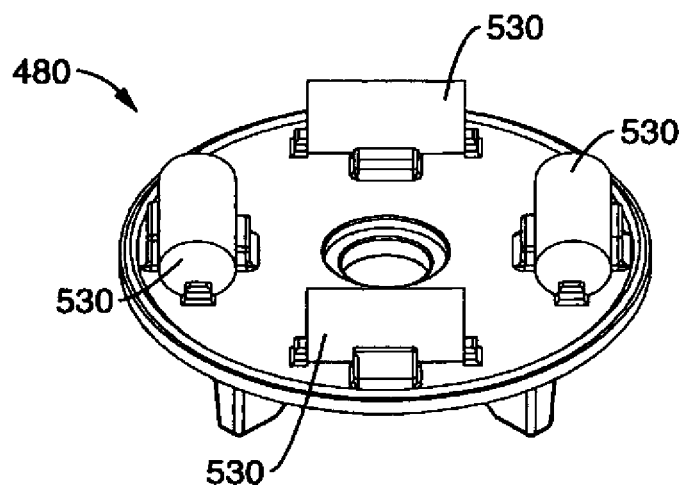
Figure 44:
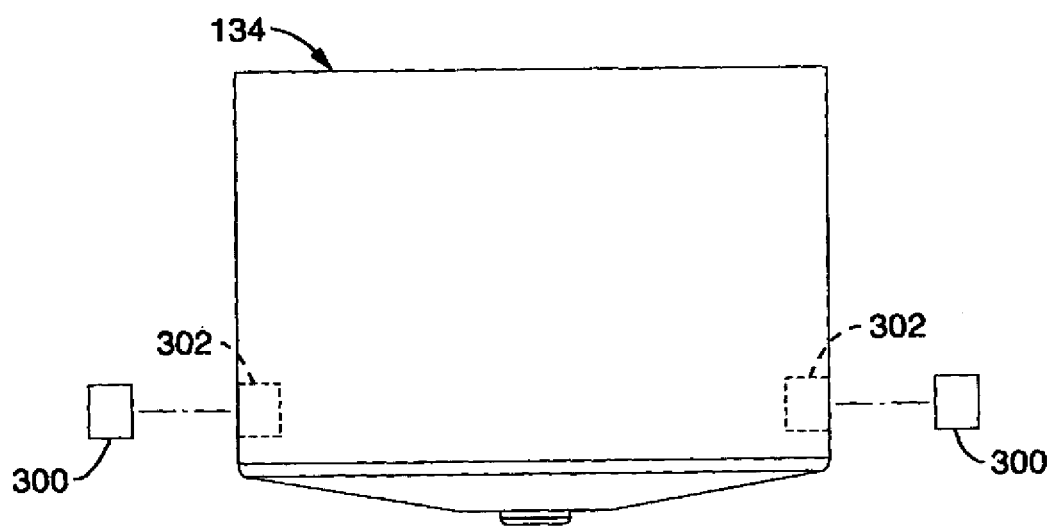

Furthermore, and referring to FIG. 44, cylindrically shaped weights 300 can be received within blind bores 302 for fine tuning or controlling the overall density of the float assembly 130. Thus, one or more weights 300 can be coupled to the float body 134 to provide ballast for the purpose of controlling the overall density of the float assembly 130. In this embodiment, the preferred materials for the weights 300 to adjust the specific gravity of the float assembly 130 are also metal rods such as stainless steel. Again, for applications of the invention to blood and bone marrow processing to harvest buffy coat, it is desirable to have the float assembly 130 be tuned between the density of plasma and packed red cells and specifically a preferred float assembly density is in the range of 1.02 to 1.08 grams/cubic centimeter and most preferentially in the range of 1.03 to 1.07 grams/cubic centimeter. The specific density used can be optimized for the intended therapeutic or diagnostic use in regard to the cell composition for the device to be produced. The heavier weight will cause an increase in red cell content and increased white blood cell (WBC) recovery.

Umbrella Valve 234

Referring to FIGS. 25, 30 through 33, and back to FIG. 14, one embodiment of the float assembly 340 further comprises the first one way valve or check valve in the form of the elastic umbrella valve 234 which is used to selectively open and close the funnel fluid passageways or apertures 450 based on a pressure differential of biological fluid on the umbrella valve 234 thereby controlling fluid flow from the funnel shaped cavity 426 to the inverted dome shaped isolation chamber 378 while precluding fluid from flowing back out of the inverted dome shaped isolation chamber 378 to the funnel shaped cavity 426 via the umbrella valve 234. Thus, the umbrella valve 234 provides a unidirectional flow of biological fluid from the second or upper volume zone 338 above the float to the third volume zone or isolation zone defined by inverted dome shaped isolation chamber 378 as a function of the pressure differential of biological fluid on the umbrella valve 234.

More specifically, and as described above and as illustrated in FIG. 14, one embodiment of the umbrella valve 234 is comprised of the generally circular canopy or dome 236 which, in an unstressed position, extends generally perpendicularly to the centrally located stem 238. The stem 238 includes the bulbous portion 240 beyond which is the tapered shaft portion 242. In one embodiment, the entire umbrella valve 234 is a one piece, integral construction.

Referring to FIGS. 25, 30, 33, and back to FIG. 14, the umbrella valve 234 is mounted to the funnel float cap 420 by securing the stem 238 through the central open ended cylindrical opening 448 disposed through the funnel float cap 420. This is accomplished by sizing the length of stem 238 between the canopy 236 and the bulbous portion 240 greater than the length of the cylindrical opening 448 and sizing the diameter of the bulbous portion greater than the diameter of the cylindrical opening 448 such that when the tapered shaft portion 242 of the stem 238 is inserted into the cylindrical opening 448 from the substantially flat bottom surface 478 of the funnel float cap 420 and pulled or stretched away from the funnel shaped upper surface 424 of the funnel float cap 420 the elastic bulbous portion 240 passes through the central open ended cylindrical opening 448 and resumes its normal shape adjacent the funnel shaped upper surface 424 of the funnel float cap 420 thereby acting as an anchor for holding the umbrella valve 234 in place. After anchoring the umbrella Valve 234 in place, the tapered shaft portion 242 may be trimmed while retaining the bulbous portion 240.

Additionally, the generally circular canopy or dome 236 includes a flat underside contact surface 244 when in the unstressed position. Thus, when the centrally located stem 238 is stretched an axial force is exerted on the canopy or dome 236 such that the underside 244 is drawn into a normal tight, sealing contact against the substantially flat bottom surface 478 of the funnel float cap 420 for sealing the funnel fluid passageways or apertures 450.

With this construction, the elastic umbrella valve 234 provides a one way valve which controls fluid flow into the inverted dome shaped isolation chamber 378 and precludes fluid flow out of the inverted dome shaped isolation chamber 378 via the elastic umbrella valve 234. In particular, the elastic umbrella valve 234 opens under a predetermined pressure differential or cracking pressure or, in other words, when the pressure in the funnel fluid passageways or apertures 450 is greater than below or on an outer surface 246 of the canopy or dome 236 by a predetermined or known cracking pressure of the umbrella valve 234. Hence, when there is a positive pressure differential defined by a pressure at the funnel fluid passageways or apertures 450 being greater than the pressure on the outer surface 246 of the canopy or dome 236 by an amount which is greater than the cracking pressure then the pressure differential causes the flexible canopy or dome 236 to invert or flex downwardly, away from the substantially flat bottom surface 478 of the funnel float cap 420 thereby permitting the biological fluid to pass into the inverted dome shaped isolation chamber 378. After the pressure differential resides to a point less than the cracking or opening pressure, the resilient canopy or dome 236 resumes its sealing position under the funnel fluid passageways or apertures 450 thereby precluding any further biological fluid from entering the inverted dome shaped isolation chamber 378.

Duckbill Valve 248

Referring to FIGS. 25, 27, 34 through 39, and back to FIG. 15, one embodiment of the float assembly 340 further comprises the second one way valve or check valve in the form of an elastic duckbill valve 248 which is used to selectively open and close the exit passageway or aperture 380 extending between the first circular exit port 382 and the second circular exit port 384 based on a pressure differential of biological fluid on the duckbill valve 248 thereby controlling fluid flow from the inverted dome shaped isolation chamber 378 to the first or lower volume zone 336 while precluding fluid from flowing back into the inverted dome shaped isolation chamber 378 from the first or lower volume zone 336 via the duckbill valve 248. Thus, the duckbill valve 248 provides a unidirectional flow of biological fluid from the isolation chamber 378 within the float assembly 340 to the first or lower volume zone 336 as a function of the pressure differential of biological fluid on the duckbill valve 248.

In one embodiment, and as described above and as illustrated in FIG. 15, the duckbill valve 248 is comprised of the open ended hollow cylindrical portion 250 coupled to the exit passageway 170 and transitioning from the radially outwardly projecting annular flange portion 252 to the hollow V-shaped or converging portion 254 which terminates to the elongated outlet slit 256 defined by the pair of resilient sealing lips 258. The resilient sealing lips 258 are formed to move apart to open the slit 256 for fluid to flow in one direction through the fluid passageway axially extending through the duckbill valve 248.

The resilient sealing lips 258 normally maintain the slit 256 in the closed position. When fluid pressure within the hollow V-shaped or converging portion at a location above the sealing lips 258 is greater than a fluid pressure below the resilient sealing lips 258 by a predefined cracking pressure of the duckbill valve 248 then the resilient sealing lips 258 spreading and the slit 256 open thereby permitting fluid to flow downwardly through the exit passageway or aperture 380 and through the axially extending fluid passageway of the duckbill valve 248. The outlet slit 256 closes when the fluid pressure below or on the outer surfaces of the resilient sealing lips 258 is higher than the fluid pressure above the resilient sealing lips 258 by more than the cracking pressure of the duckbill valve 248 thereby preventing the backflow of fluid through the duckbill valve 248. Additionally, if fluid flow stops or reverses direction, the back-pressure exerted by the fluid upon the outer surfaces of the resilient sealing lips 258 forces the lips into sealing engagement against one another, closing outlet slit 256 and preventing fluid backflow.

As assembled, the annular flange portion 252 of the duckbill valve is seated between the bottom surface 386 of the float body 344 and the annular ledge 492 of the bottom float cap 480 or the annular ledge 512 of the bottom float cap 500 such that the cylindrical portion 250 of duckbill valve 248 respectively passes through the centrally located aperture 494 or 514 and such that the hollow V-shaped or converging portion 254 extends respectively below the bottom float cap 480 or 500. In this arrangement, the exit passageway or aperture 380 is in open communication with the axially extending fluid passageway of the duckbill valve 248 and a press type fit or coupling is provide between the bottom surface 386 of the float body 344, the duckbill valve 248, and either the annular ledge 492 of bottom float cap 480 or the annular ledge 512 of bottom float cap 500 for maintaining a seal between the duckbill valve 248 and the float body 344.

Use and Operation

In use and operation, and referring to the drawings, the device 310 follows the use and operation delineated hereinabove for device 10. Initially device 310 receives a multiple component biological fluid sample (e.g., peripheral blood, bone marrow aspirate, blood components, cord blood, apheresis blood products, lipo-aspirate, semen, urine, milk, ascites fluid, exudate or cerebrospinal fluids) by performing the steps of removing the cap 85 from the male luer lock head 88 of the inlet valve 86, coupling a conventional needleless syringe 270 or other dispensing device containing the biological fluid sample to the male luer lock head 88 of the inlet valve 86, injecting or dispensing the biological fluid sample into the device 310 from the conventional syringe 270 or other dispensing device, decoupling the conventional syringe 270 or other dispensing device from the male luer lock head 88 of the inlet valve 86, and reattaching cap 85. When supplying the device 310 with biological fluid, the air filter allows air to escape from the enclosure 334.

The received biological fluid sample fills the second or upper volume zone 338 above the inverted dome shaped isolation chamber 378 including the funnel shaped cavity 426 and flows to the first or lower volume zone 336 below the float assembly 340 via the circumferential gap 356 disposed between the outer circumferential surface 352 of the float sidewall 350 and the inner circumferential surface 324 of the tube 312. The biological fluid sample is initially precluded from entering or passing through the inverted dome shaped isolation chamber 378 by the normally closed umbrella valve 234 and the normally closed duckbill valve 248. Additionally, the spaced apart fins 496 of bottom float cap 480 or the spaced apart cylindrical legs 516 of the bottom float cap 500 provide an initial lift off the float assembly 340 from the interior surface 330 of the closed bottom end 314 of the tube 312 for precluding a vacuum seal from forming therebetween while also protecting the elastic duckbill valve 248 under initial conditions.

Once the biological fluid sample has been received within the enclosure 334 defined by the tube 312 and tube cap 50, the device 310 is placed in a conventional centrifugation device 280 which is operated for one or more predetermined durations at one or more predetermined speeds. In one embodiment, and for a biological fluid sample exemplified by blood, the conventional centrifugation device 280 is operated for about 12 to about 15 minutes at about 3,200 RPM. Of course, one or more time durations and one or more speeds can be empirically determined for a specific biological fluid to be processed by the device 310 and may vary from one biological fluid to another.

Upon initial centrifugation of the device 310, the biological fluid in the funnel shaped cavity 426 increasingly applies a pressure on the umbrella valve 234 which results in a pressure differential on the umbrella valve 234 becoming greater than the cracking pressure of the umbrella valve 234 thereby allowing fluid to flow through one or more of the funnel fluid passageways or apertures 450 and into the inverted dome shaped isolation chamber 378 which begins to fill and apply a second pressure on the duckbill valve 248 which results in a pressure differential on the duckbill valve 248 being greater than the cracking pressure of the duckbill valve 248 thereby allowing biological fluid to initially flow out of the inverted dome shaped isolation chamber 378 via exit passageway or aperture 380. At first, the biological fluid quickly flows through the inverted dome shaped isolation chamber 378 and when the sample is blood the hematocrit is initially not concentrated. With both the umbrella valve 234 and duckbill valve 248 in an open position, the building of the column of biological fluid in the first or lower volume zone 336 or below the float assembly 340 continues. As this column of the biological fluid builds, the device 310 provides a unique circulation process or density feedback process which will be clearly delineated by using peripheral blood as an example of the biological fluid being processed.

Accordingly, and as the biological fluid such as peripheral blood stratify based on density and the components build the column, the cells that are just below the bottom surface 484 of the bottom float cap 480 or the bottom surface 506 of the bottom float cap 500 continue to stratify such that the cell density above the level of the duckbill valve 248 is less than the cell density below the level of the duckbill valve 248 by an amount which provides a pressure differential which is less than the cracking pressure of the duckbill valve 248 thereby resulting in the closure of the duckbill valve 248 such that over time the reds cells accumulate at the bottom section 362 of the inverted dome shaped isolation chamber 378 and become packed and thus, there are packed cells at the bottom section 362 of the chamber which have a greater density than the cells right below the level of the duckbill valve 248 because at the same time that the density of red cells is increasing at the bottom section 362 the density right below the duckbill valve 248 is decreasing because greater density cells are also migrating toward the bottom end 314 of the tube 312. Thus, as this density increases a pressure differential builds to surpass the cracking pressure of the duckbill valve 248 which then opens thereby allowing the red cells to flow through the exit passageway or aperture 380 and displace the biological fluid in the first or lower zone 336 which, in turn, pushes fluid up or causes a surge of fluid up through the circumferential gap 356 between the outer circumferential surface 352 of the float body sidewall 350 and the inner circumferential surface 324 of the tube 312. This upward fluid flow has the effect of carrying the lighter components of the biological fluid including the white blood cells and platelets from the first or lower volume zone 336 of the tube 312 back up to the second or upper volume zone 338 of the tube 312 wherein these lighter components are heavier than the plasma in the second or upper volume zone 338 that they got circulated into so the white blood cells and platelets or buffy coat included therein fall back down through the funnel shaped cavity 426, past the umbrella valve 234, and collect in the inverted dome shaped isolation chamber 378. This cell circulation process or density feedback process continues on towards an equilibrium where the pressure differential or the density differential of the cells above and below duckbill valve 248 is less than the cracking pressure of the duckbill valve 248 resulting in the duckbill valve 248 having a final closure and similarly the density differential of the cells above and below umbrella valve 234 is less than the cracking pressure of the umbrella valve 234 resulting in the umbrella valve 234 having a final closure thereby concluding the unique cell circulation process or density feedback process of the device 310.

Hence, this cell circulation process or density feedback process allows multiple chances at capturing the white cells or other target components of interest in the inverted dome shaped isolation chamber 378 thereby providing higher recovery rates as compared to know prior art devices.

Following the centrifugation step, the device 310 containing the separated and isolated biological fluid components is removed from the centrifugation device 280 and placed on a conventional magnetic stirrer 290 as diagrammatically shown in FIG. 20. The stirrer is then energized for activating or coacting with a magnetic stirring bar 292 located inside the inverted dome shaped isolation chamber 378 for stirring at least one isolated target component within the isolation chamber 378 for increasing a recovery rate of a subsequent harvesting step. In one embodiment, at least the one isolated target component or fraction is stirred for about twenty seconds. Of course, stirring times may vary from one biological fluid to another and a specific stirring time for a specific biological fluid can be empirically determined.

Following the stirring step, the harvesting step of at least the one isolated target component or fraction is performed and is comprised of the steps of removing the cap 99 from the male luer lock head 102 of the extraction valve 100, coupling a conventional needleless syringe 272 or other extraction device to the male luer lock head 102 of the extraction valve 100, aspirating at least the one isolated target component or fraction from the inverted dome shaped isolation chamber 378 by providing a vacuum from the syringe 103 to the extraction passageway or aperture 404 and onto port 414 disposed in the radiused bottom section 362 of the inner hemispherical surface 358 and aspirating at least the one isolated target component or fraction from the inverted dome shaped isolation chamber 378 and through the port 414 and into and through the extraction passageway or aperture 404 disposed in the float body 344, the coiled tube 124, the barb fitting 114, the L-shaped housing passageway 62, the extraction valve 100, and finally into the conventional needleless syringe 272.

After the harvesting step is completed, the conventional needleless syringe 103 is decoupled from the male luer lock head 102 of the extraction valve 100 in preparation for at least one diagnostic or therapeutic application of at least the one target component or fraction. When harvesting at least the one target component or fraction, the air filter allows air into the enclosure 48. Additionally, when the cracking pressure of the umbrella valve is reached during a harvesting step, plasma flows into the inverted dome shaped isolation chamber 378 to displace the removed volume of at least the one target component or fraction.

It should be noted that a counter weight device 282 maybe used in the conventional centrifugation device 280 to offset the weight of the device 310 containing biological fluid as required.

Furthermore, 310 should be assembled in an environment to minimize the risk of particulate matter in the fluid path and when used for clinical applications, the device 310 must be sterilized and the fluid path should be non-pyrogenic.

Moreover, the materials used for the construction of the various embodiments of the device for separating and isolating components of a biological fluid include plastics, rubber, metal and magnet that are biocompatible and substantially free of any cytotoxic leachables. Preferred plastics for the construction of the tube are polystyrene or polycarbonate. Plastics for the construction of the body of the funnel and isolation float include polystyrene or polycarbonate. Preferred materials for the one way valves in the float are silicone rubbers stable to gamma irradiation. The preferred materials for the ballast or weights to adjust the specific gravity of the funnel assembly are metal rods such as stainless steel that are disposed in a location within the funnel and isolation float that does not permit contact with the biological components. Preferred magnetic stirring bars placed into the isolation chamber of the funnel and isolation float are made from a magnetic material such as neodymium magnet. The magnetic stirring bar can be a variety of shapes and sizes but should be selected so as to be compatible with the intended specific gravity of the float and to avoid the possibility of the magnetic stirrer obstructing the flow of liquids in the outlet apertures of the interior chamber of the float. A simple rod magnet having a size that is approximately half of the interior diameter of the interior of the isolation chamber of the float is appropriate.

A preferred method of preparing the sample tube, sample tube cap and funnel and isolation float is by injection molding. Alternatively, the funnel and isolation float can be manufactured by means of tools present in machine shop such as lathes and drills. The coiled tube used to connect the lid to the float is preferably medical grade polyvinylchloride. Because the float must be made with precision, it is preferable to make the device in subcomponents to facilitate precision injection molding and it is preferable the subcomponents be assembled using sonic welding devices or other reliable means.

The above delineation of the embodiments 10 and 310 of the device, including their use and operation, demonstrates the industrial applicability of this invention.

Accordingly, it should be apparent that further numerous structural modifications and adaptations may be resorted to without departing from the scope and fair meaning of the present invention as set forth hereinabove and as described herein below by the claims.

We claim:

1. A device for separating and isolating components of a biological fluid with centrifugation, said device comprising:
   an enclosure comprising an interior circumferential surface defining a chamber for containing a biological fluid having multiple components;
   a float slideably disposed within said enclosure and partitioning said enclosure into a lower volume zone and an upper volume zone;
   said float comprising an interior isolation chamber defining an intermediate volume zone and an exterior circumferential surface circumferentially spaced from said interior circumferential surface of said enclosure for defining a circumferential gap therebetween;
   a first valve means for opening and closing communication of biological fluid from said upper volume zone to said interior isolation chamber within said float; and
   a second valve means for opening and closing communication of biological fluid from said interior isolation chamber within said float to said lower volume zone of said container wherein under centrifugation said first valve means and said second valve means control at least one closed loop circulation of biological fluid into said interior isolation chamber from said upper volume zone, out of said interior isolation chamber into said lower volume zone, out of said lower volume zone and through said circumferential gap to said upper, volume zone, and back into said interior isolation chamber as a function of a first pressure differential of biological fluid on said first valve means and as a function of a second pressure differential of biological fluid on said second valve means for isolating at least one target component of the multiple component biological fluid within said interior isolation chamber of said float.

2. The device of claim 1 wherein said float includes an upper funnel surface for promoting flow of biological fluid into said interior isolation chamber as said function of said first pressure differential of biological fluid on said first valve means.

3. The device of claim 2 wherein said interior isolation chamber is shaped as an inverted dome shaped chamber.

4. The device of claim 3 further comprising means for extracting the at least one target component from said inverted dome shaped chamber by aspirating the at least one target component from a lower arcuate portion of said inverted dome shaped chamber.

5. The device of claim 4 wherein said first valve means comprises an umbrella valve.

6. The device of claim 5 wherein said second valve means comprises a duckbill valve.

7. The device of claim 6 further comprising a standoff means for initially spacing said float from an interior bottom surface of said enclosure.

8. The device of claim 1 wherein said float, said first valve means, and said second valve means have a combined selected density of about 1.02 grams/cubic centimeter to about 1.08 grams/cubic centimeter.

9. The device of claim 1 further comprising a magnetic stirring bar disposed within said interior isolation chamber of said float for stirring at least the one target component of the biological fluid within said interior isolation chamber of said float when magnetically activated.

10. A device for separating and isolating components of a biological fluid with centrifugation, said device comprising:
    a container comprising a closed bottom end, an open top end, and a container sidewall extending between said closed bottom end and said open top end, said sidewall having an inner circumferential surface defining a containing chamber extending along a central longitudinal axis of said container;
    a cap for selectively closing said open top end of said container for defining an enclosure for containing a biological fluid having multiple components;
    a float assembly slideably disposed within said container and partitioning said container into a lower volume zone and an upper volume zone;
    said float assembly comprising:
      a lower cylindrical portion including an inverted hemispherically shaped interior surface surmounted by an interior ceiling surface for defining an inverted domed shaped chamber for isolating a target component of the biological fluid;
      an upper cylindrical portion surmounting said lower cylindrical portion and including a conically shaped upper surface defining a funnel shaped cavity converging towards said lower cylindrical portion of said float for receiving, directing, and promoting biological fluid flow from said upper volume zone toward said inverted domed shaped chamber;
      an open ended entrance passageway disposed within said float for providing open fluid communication between said funnel shaped cavity and said inverted domed shaped chamber;
      an open ended exit passageway disposed within said float for providing open communication between said inverted domed shaped chamber and said lower volume zone;
      a first valve means for selectively opening and closing said open ended entrance passageway as a function of a first pressure differential on said first valve means for controlling fluid flow from said funnel shaped cavity to said inverted dome shaped chamber, and precluding fluid back flow through said first valve means from said inverted dome shaped chamber to said funnel shaped cavity;
      a second valve means for selectively opening and closing said open ended exit passageway as a function of a second pressure differential on said second valve means for controlling fluid flow out of said inverted dome shaped chamber to said lower volume zone of said container and precluding fluid back flow through said second valve means from said lower volume zone to said inverted domed shaped chamber, and wherein under centrifugation said first valve means and said second valve means initially allow components of the biological fluid to flow through said inverted domed shaped chamber and subsequently close to seal said inverted domed shaped chamber as said function of said first pressure differential on said first valve means and as said function of said second pressure differential on said second valve means for isolating the target component of the biological fluid within said inverted domed shaped chamber of said float.

11. The device of claim 10 further comprising a coil of flexible tubing having one end operatively coupled to an extraction valve coupled to said cap and another end operatively coupled to one end of an open ended extraction passageway disposed in said upper cylindrical portion and said lower cylindrical portion of said float assembly and having another end terminating in a bottom area of said inverted hemispherically shaped interior surface of said lower cylindrical portion of said float assembly for extracting the target component of the biological fluid isolated within said inverted domed shaped chamber by applying a vacuum to said extraction valve coupled to said cap.

12. The device of claim 10 further comprising an inlet valve means coupled to said cap and in open communication with said containing chamber for allowing the biological fluid having multiple components to be dispensed into said containing chamber.

13. The device of claim 10 further comprising an air filter means coupled to said cap and in open communication with said containing chamber for allowing air to escape from said containing chamber when dispensing the biological fluid having multiple components into said containing chamber and for allowing air to enter said containing chamber when extracting the target component of the biological fluid isolated within said inverted domed shaped chamber.

14. The device of claim 10 further comprising a standoff means for initially spacing said float from an interior bottom surface of said container for precluding a vacuum seal from forming therebetween.

15. The device of claim 10 wherein said first valve means comprises an umbrella valve.

16. The device of claim 10 wherein said second valve means comprises a duckbill valve.

17. The device of claim 10 wherein said float assembly has a selected density of about 1.02 grams/cubic centimeter to about 1.08 grams/cubic centimeter.

18. The device of claim 10 further comprising a magnetic stirring bar disposed within said inverted domed shaped chamber of said float for stirring the target component of the biological fluid within said inverted domed shaped chamber of said float when magnetically activated.

* * * * *

UNITED STATES PATENT AND TRADEMARK OFFICE
CERTIFICATE OF CORRECTION

PATENT NO. : 8,177,072 B2
APPLICATION NO. : 12/315722
DATED : May 15, 2012
INVENTOR(S) : Chapman et al.

It is certified that error appears in the above-identified patent and that said Letters Patent is hereby corrected as shown below:

On the title page, "34 Drawing Sheets" should read --26 Drawing Sheets--.

On the title page, illustrative figure 1 should be substituted with FIG. 1 on the attached replacement drawing sheets 1-26.

Signed and Sealed this
Twenty-seventh Day of November, 2012

David J. Kappos
*Director of the United States Patent and Trademark Office*